US008962612B2

(12) United States Patent
Hamaguchi et al.

(10) Patent No.: US 8,962,612 B2
(45) Date of Patent: Feb. 24, 2015

(54) TETRAHYDROISOQUINOLINE DERIVATIVE

(71) Applicant: Astellas Pharma Inc, Chuo-ku, Tokyo (JP)

(72) Inventors: Wataru Hamaguchi, Tokyo (JP); Isao Kinoyama, Tokyo (JP); Yohei Koganemaru, Tokyo (JP); Takehiro Miyazaki, Tokyo (JP); Osamu Kaneko, Tokyo (JP); Ryuichi Sekioka, Tokyo (JP); Takuya Washio, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 13/956,924

(22) Filed: Aug. 1, 2013

(65) Prior Publication Data

US 2013/0317010 A1 Nov. 28, 2013

Related U.S. Application Data

(63) Continuation-in-part of application No. PCT/JP2012/052213, filed on Feb. 1, 2012.

(30) Foreign Application Priority Data

Feb. 2, 2011 (JP) .................................. 2011-020453

(51) Int. Cl.

| A61K 31/55 | (2006.01) |
| C07D 209/44 | (2006.01) |
| A61K 31/4035 | (2006.01) |
| A61K 31/472 | (2006.01) |
| A61K 31/4725 | (2006.01) |
| A61K 31/4747 | (2006.01) |
| C07D 217/06 | (2006.01) |
| C07D 217/22 | (2006.01) |
| C07D 217/24 | (2006.01) |
| C07D 221/20 | (2006.01) |
| C07D 223/16 | (2006.01) |
| C07D 401/04 | (2006.01) |

(52) U.S. Cl.
CPC .......... *C07D 209/44* (2013.01); *A61K 31/4035* (2013.01); *A61K 31/472* (2013.01); *A61K 31/4725* (2013.01); *A61K 31/4747* (2013.01); *A61K 31/55* (2013.01); *C07D 217/06* (2013.01); *C07D 217/22* (2013.01); *C07D 217/24* (2013.01); *C07D 221/20* (2013.01); *C07D 223/16* (2013.01); *C07D 401/04* (2013.01)
USPC ......................................................... 514/217

(58) Field of Classification Search
None
See application file for complete search history.

(56) References Cited

U.S. PATENT DOCUMENTS

| 6,916,813 | B2 | 7/2005 | Atwal et al. | |
| 8,183,234 | B2 * | 5/2012 | Lal et al. ................... | 514/211.11 |
| 2004/0039033 | A1 | 2/2004 | Atwal et al. | |
| 2007/0010526 | A1 | 1/2007 | Haeberlein et al. | |
| 2007/0244152 | A1 * | 10/2007 | Lowy ............................ | 514/311 |
| 2010/0324017 | A1 | 12/2010 | Kinoyama et al. | |

FOREIGN PATENT DOCUMENTS

| EP | 0 810 206 | 12/1997 |
| WO | WO 03/037887 | 5/2003 |
| WO | WO 03/050261 | 6/2003 |
| WO | WO 2008/096791 | 8/2008 |
| WO | WO 2009/022633 | 2/2009 |
| WO | WO 2010/090304 | 8/2010 |
| WO | WO 2010/090305 | 8/2010 |
| WO | WO 2011/016504 | 2/2011 |

OTHER PUBLICATIONS

International Search Report from Japanese Patent Office of PCT International Application No. PCT/JP2012/052213, mailed Apr. 24, 2012.

* cited by examiner

*Primary Examiner* — San-Ming Hui
*Assistant Examiner* — Jeanmarie Calvillo
(74) *Attorney, Agent, or Firm* — Finnegan, Henderson, Farabow, Garrett & Dunner, LLP

(57) ABSTRACT

To provide an excellent agent for preventing or treating dementia and schizophrenia based on serotonin 5-$HT_{5A}$ receptor regulating action, it was found that a tetrahydroisoquinoline derivative characterized by a structure in which an acylguanidino group binds to a N atom of a tetrahydroisoquinoline ring or the like, and a cyclic group binds to an unsaturated ring has a potent 5-$HT_{5A}$ receptor regulating action and an excellent pharmacological action based on the regulating action and also discovered that the tetrahydroisoquinoline derivative is useful as an agent for treating or preventing dementia, schizophrenia, and the like, whereby the present invention has been completed.

15 Claims, No Drawings

TETRAHYDROISOQUINOLINE DERIVATIVE

CROSS REFERENCE TO RELATED APPLICATIONS

This application is a continuation-in-part of International Application No. PCT/JP2012/052213 filed on Feb. 1, 2012, which claims the benefit of Japan Patent Application. No. 2011-020453 filed on Feb. 2, 2011. The entire disclosures of International Application No. PCT/JP2012/052213 and Japan Patent Application. No. 2011-020453 are incorporated by reference herein.

TECHNICAL FIELD

The present invention relates to a medicament, particularly, a tetrahydroisoquinoline derivative which has a $5\text{-HT}_{5A}$ receptor regulating action and is useful as an agent for treating or preventing dementia, schizophrenia, and the like.

BACKGROUND ART

In recent years, it has been suggested that a $5\text{-HT}_{5A}$ receptor as one of subtypes of serotonin receptors plays an important role in dementia and schizophrenia. For example, it has been reported that exploratory behavior increases in a $5\text{-HT}_{5A}$ receptor knock-out mouse, and hyperactivity caused by LSD is inhibited in the $5\text{-HT}_{5A}$ receptor knock-out mouse (Neuron, 22, 581-591, 1999). From the results of gene expression analysis, it has been reported that the $5\text{-HT}_{5A}$ receptor is highly expressed in the brain of human beings and rodents, and in the brain, the $5\text{-HT}_{5A}$ receptor is highly expressed in CA1 and CA3 pyramidal cells of the hippocampus involved in memory and in the frontal lobe (cerebral cortex) deeply involved in schizophrenia (Molecular Brain Research, 56, 1-8, 1998). Moreover, it has been reported that the polymorphism of the $5\text{-HT}_{5A}$ receptor gene relates to schizophrenia (Neuroreport 11, 2017-2020, 2000; Mol. Psychiatry 6, 217-219, 2001; J. Psychiatr. Res. 38, 371-376, 2004). Thus, it is suggested that regulation of the function of the $5\text{-HT}_{5A}$ receptor leads to improvement of dementia and schizophrenia. Accordingly, there is a demand for a compound having such a function.

So far, several compounds having affinity with the $5\text{-HT}_{5A}$ receptor have been reported.

For example, it has been reported that a tricyclic compound represented by the following formula (a) binds to the $5\text{-HT}_{5A}$ receptor and is used for treating dementia, schizophrenia, and the like (Patent Document 1).

[Chem. 1]

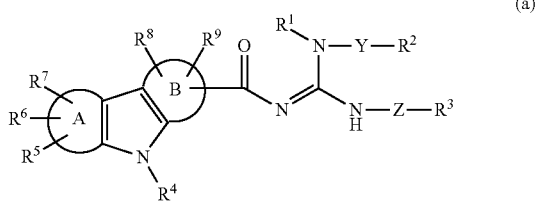

(a)

(In the formula, A represents benzene, thiophene, furan, cyclohexene, or tetrahydropyridine ring, and B represents benzene, cyclohexene, or tetrahydropyridine ring. See the corresponding gazette for more detail.)

The corresponding gazette relates to the tricyclic compound which is different from the tetrahydroisoquinoline derivative of the present invention.

In addition, it has been reported that a bicyclic acylguanidine compound represented by the following formula (b) binds to the $5\text{-HT}_{5A}$ receptor and can be used for treating dementia, schizophrenia, and the like (Patent Document 2).

[Chem. 2]

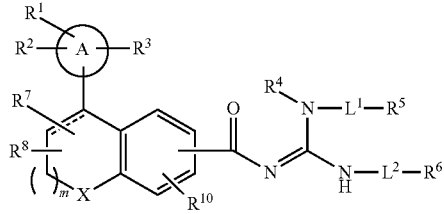

(b)

(In the formula, A represents phenyl or the like; $R^1$, $R^2$, and $R^3$ represent H, lower alkyl, halogen, or the like; $R^7$ and $R^8$ represent H, lower alkyl, or the like; X represents O, S, $CR^{9a}R^{9b}$; $R^{9a}$ and $R^{9b}$ represent H or the like; a dotted line represents a bond or in existence; m represents 0, 1, or 2; $L^1$ and $L^2$ represent a bond or the like; and $R^4$, $R^5$, and $R^6$ represent H or the like, respectively. See the corresponding gazette for more detail.)

The corresponding gazette relates to a compound in which the moiety of a bicyclic ring group is chroman or benzothiophene, which is different from the tetrahydroisoquinoline derivative of the present invention.

Further, Patent Documents 3 and 4 respectively disclose that naphthoyl guanidine compounds which are represented by the following formulae (c) and (d) and have been substituted with a cyclic group bind to the $5\text{-HT}_{5A}$ receptor and are useful for treating dementia, schizophrenia, and the like.

[Chem. 3]

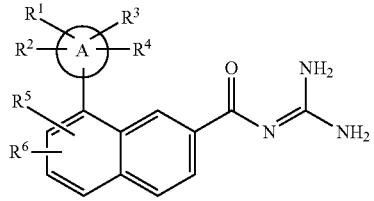

(c)

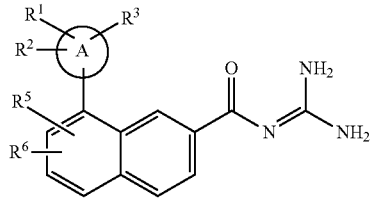

(d)

(In the formula, A represents various cyclic groups including phenyl, pyridyl, and the like. See the corresponding gazette for more detail.)

The corresponding gazette relates to a naphthalene compound which is different from the tetrahydroisoquinoline derivative of the present invention.

In addition, Patent Document 7 discloses that a quinoline or isoquinoline compound which is represented by the following formula (e) and has been substituted with a cyclic group binds to the 5-HT$_{5A}$ receptor and is useful for treating dementia, schizophrenia, and the like.

[Chem. 4]

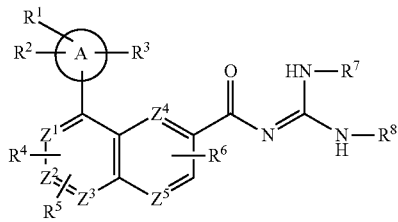

(e)

(In the formula, A represents a cyclic group, and one of $Z^1$, $Z^2$, $Z^3$, $Z^4$, and $Z^5$ represents a nitrogen atom and the others are carbon atoms. See the corresponding gazette for more detail.)

The corresponding gazette relates to a quinoline or isoquinoline compound in which an acylguanidino group binds to a C atom, which is different from the tetrahydroisoquinoline derivative of the present invention.

Moreover, it has been reported that a naphthoyl guanidine compound represented by the following formula (f) is useful as an agent which inhibits Na+/H+ exchange and can be used for treating arrhythmia, angina, and the like (Patent Document 5).

[Chem. 5]

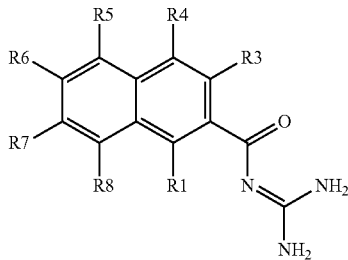

(f)

(In the formula, $R^1$ and $R^3$ to $R^8$ represent various substituents via a linker group such as O, amide; or represent H, alkyl, or the like. See the corresponding gazette for more detail.)

In addition, a tetrahydroisoquinoline compound represented by the following formula (g) has been reported as a regulator for 5-HT$_{1B}$ and 5-HT$_{1D}$ receptors (Patent Document 6).

[Chem. 6]

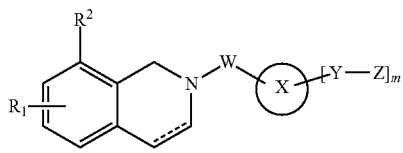

(g)

(In the formula, R$_1$ represents alkyl, halogen, or the like; R$^2$ represents aryl, a hetero ring, or carboxamide; W represents a linker group such as —C(O)— or —C(O)NR$^a$—; and ring X represents aryl which may be substituted or a hetero ring which may be substituted. See the corresponding gazette for more detail.)

The compound disclosed in the corresponding gazette essentially has the ring X, which is different from the tetrahydroisoquinoline derivative of the present invention in which an acylguanidino group binds to a N atom in the corresponding moiety.

So far, as a 5-HT$_{5A}$ receptor regulator, a tetrahydroisoquinoline derivative in which an acylguanidino group binds to a N atom has not been reported.

PRIOR ART DOCUMENT

Patent Document

Patent Document 1: Pamphlet of International Publication WO 2008/096791
Patent Document 2: Pamphlet of International Publication WO 2009/022633
Patent Document 3: Pamphlet of International Publication WO 2010/090304
Patent Document 4: Pamphlet of International Publication WO 2010/090305
Patent Document 5: EP810206
Patent Document 6: Pamphlet of International Publication WO 2003/037887
Patent Document 7: Pamphlet of International Publication WO 2011/016504

SUMMARY OF INVENTION

Problems to be Solved by the Invention

An object of the present invention is to provide an excellent agent for treating or preventing dementia, schizophrenia, and the like based on the 5-HT$_{5A}$ receptor regulating action.

Means for Solving the Problems

The present inventors conducted extensive examination regarding compounds having 5-HT$_{5A}$ receptor regulating action. As a result, they found that a tetrahydroisoquinoline derivative characterized by a structure in which an acylguanidino group binds to a N atom of a tetrahydroisoquinoline ring or the like, and a cyclic group binds to an unsaturated ring has a potent 5-HT$_{5A}$ receptor regulating action and an excellent pharmacological action based on the regulating action, and also discovered that the tetrahydroisoquinoline derivative is useful as an agent for treating or preventing dementia, schizophrenia, and the like, thereby completing the present invention.

The compound of the present invention is a tetrahydroisoquinoline derivative featuring having an acylguanidino group at the N atom, which is structurally different from the compounds disclosed in Patent Documents 1 to 7 described above.

Thus, the present invention relates to a compound of formula (I) and a pharmaceutically acceptable salt thereof.

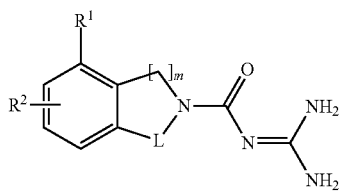

(I)

(symbols in the formula represent the following.

R¹: H, —O-(lower alkyl), —O-(halogeno-lower alkyl), or aryl, heteroaryl, cycloalkyl, or cycloalkenyl which may be respectively substituted with substituent(s) selected from G¹, G¹: halogen, —CN, —OH, —O—(lower alkyl), —O—(halogeno-lower alkyl), lower alkyl, halogeno-lower alkyl, -(lower alkylene)-OH, -(lower alkylene)-O-(lower alkyl), and cycloalkyl, R²: H, lower alkyl, halogeno-lower alkyl, halogen, —CN, —OH, —O-(lower alkyl), —O-(halogeno-lower alkyl), -(lower alkylene)-OH, -(lower alkylene)-O-(lower alkyl), or cycloalkyl, L: —C(R³)(R⁴)—(CH₂)$_n$—, m: 1 or 2, n: 0, 1, or 2, R³ and R⁴: these may be the same as or different from each other and respectively represent H, lower alkyl, halogen, —OH, —O-(lower alkyl); alternatively, R³ and R⁴ may be combined with each other to form —R³—R⁴—, and —R³—R⁴— may form cycloalkylene together with the carbon atom binding thereto, as a lower alkylene having 2 or more carbon atoms.)

Moreover, unless otherwise specified, if symbols in a certain chemical formula in the present specification are also used in another chemical structure, the same symbols have the same meanings.

Effects of the Invention

The compound of formula (I) has such advantages that it has a potent 5-HT$_{5A}$ receptor regulating action and excellent pharmacological action based on the regulating action. The pharmaceutical composition of the present invention is useful for treating or preventing 5-HT$_{5A}$ receptor-related diseases, particularly, dementia, schizophrenia, bipolar disorder, attention deficit hyperactivity disorder, and mood disorder.

EMBODIMENTS FOR CARRYING OUT THE INVENTION

Hereinafter, the present invention will be described in detail.

In the present specification, a "5-HT$_{5A}$ receptor regulator" is a generic term of a compound (5-HT$_{5A}$ antagonist) which inhibits the activation of the 5-HT$_{5A}$ receptor by acting as an antagonist against an endogenous ligand, and a compound (5-HT$_{5A}$ agonist) which activates the 5-HT$_{5A}$ receptor so as to express the action. An embodiment of the "5-HT$_{5A}$ receptor regulator" includes, for example, a 5-HT$_{5A}$ antagonist.

Diseases for which the "5-HT$_{5A}$ receptor regulator" is effective include dementia, schizophrenia, bipolar disorder, attention deficit hyperactivity disorder, and mood disorder. Another embodiment thereof is dementia or schizophrenia, still another embodiment thereof is dementia, and yet another embodiment thereof is schizophrenia.

A "Lower alkyl" refers to a linear or branched alkyl group having 1 to 6 carbon atoms (hereinafter, abbreviated to $C_{1-6}$). Specifically, the lower alkyl is methyl, ethyl, n-propyl, isopropyl, n-butyl, isobutyl, sec-butyl, tert-butyl, n-pentyl, n-hexyl, or the like. Another embodiment thereof is a $C_{1-4}$ alkyl, and still another embodiment thereof is methyl, ethyl, n-propyl, or isopropyl.

A "Lower alkylene" refers to a substituent of a divalent group formed by removing any hydrogen atom from the above lower alkyl. An embodiment thereof is methylene, ethylene, trimethylene, or 1,2-propylene, another embodiment thereof is ethylene, trimethylene, or 1,2-propylene, and still another embodiment thereof is ethylene.

A "Halogen" refers to F, Cl, Br, or I. An embodiment thereof is F or Cl.

A "Halogeno-lower alkyl" refers to a $C_{1-6}$ alkyl group substituted with one or more halogen atoms. An embodiment thereof is a $C_{1-6}$ alkyl group substituted with 1 to 5 halogen atoms, and another embodiment thereof is difluoromethyl or trifluoromethyl.

An "Aryl" refers to a $C_{6-14}$ mono- to tricyclic aromatic hydrocarbon ring group. An embodiment thereof is phenyl or naphthyl, and another embodiment thereof is phenyl.

A "Heteroaryl" refers to a 5- to 13-membered aromatic ring group comprising one or more hetero atoms constituting the ring, wherein the ring may be fused. An embodiment thereof is a monocyclic heteroaryl, another embodiment thereof is a 5- to 8-membered heteroaryl, still another embodiment thereof is pyridyl or pyrimidinyl, and yet another embodiment thereof is pyridyl.

A "Cycloalkyl" refers to a $C_{3-10}$ saturated hydrocarbon ring group, and this group may have a bridge. The cycloalkyl is specifically cyclopropyl, cyclobutyl, cyclopentyl, cyclohexyl, cycloheptyl, cyclooctyl, adamantyl, or the like. Another embodiment thereof is a $C_{3-6}$ cycloalkyl group, still another embodiment thereof is cyclopropyl or cyclobutyl, and yet another embodiment thereof is cyclopropyl.

A "Cycloalkylene" refers to a divalent $C_{3-10}$ saturated hydrocarbon ring group which is formed by removing any two hydrogen atoms from the above cycloalkyl. An example of cycloalkylene that R³ and R⁴ are combined with each other, and —R³—R⁴— form cycloalkylene together with the carbon atom binding thereto, as a lower alkylene having 2 or more carbon atoms, includes cyclopropane-1,1-diyl. Another embodiment thereof is cyclobutane-1,1-diyl.

A "Cycloalkenyl" refers to a $C_{3-10}$ saturated hydrocarbon ring group in which the above cycloalkyl partially has an unsaturated bond. The cycloalkenyl is, for example, cyclohexenyl.

The words "which may be substituted" mean that a group is not substituted or has 1 to 5 substituents. In an embodiment, the words mean that a group has 2 to 3 substituents, in another embodiment, the words mean that a group has 2 substituents, and in still another embodiment, the words mean that a group has 3 substituents. When a group has multiple substituents, the substituents may be the same as or different from each other.

Moreover, the present invention includes the following compounds or a pharmaceutically acceptable salt thereof.

(1) The compound of formula (I), wherein R¹ represents aryl, heteroaryl, or cycloalkyl which may be respectively substituted with substituent(s) selected from G¹, represents phenyl, pyridyl, or cycloalkyl which may be respectively substituted with substituent(s) selected from G¹ in an embodiment, represents phenyl which may be substituted with halogen or —O-(lower alkyl) in another embodiment, represents pyridyl which may be substituted with halogen or —O-(lower alkyl) in still another embodiment, represents phenyl which may be substituted with halogen in yet another embodiment, or represents pyridyl which may be substituted with halogen in another embodiment.

Herein, $R^1$ may be substituted with one or more substituent(s) selected from $G^1$ (2) The compound of formula (I), wherein $G^1$ represents halogen or —O-(lower alkyl), represents F in another embodiment, represents Cl in still another embodiment, or represents methoxy in yet another embodiment.

(3) The compound of formula (I), wherein $R^2$ represents halogen, represents lower alkyl in another embodiment, represents H, F, Cl, or methyl in still another embodiment, represents H in yet another embodiment, represents F in another embodiment, represents Cl in another embodiment, or represents methyl in another embodiment.

(4) The compound of formula (I), wherein m represents 1, or represents 2 in another embodiment.

(5) The compound of formula (I), wherein n represents 0, represents 1 in another embodiment, or represents 2 in still another embodiment.

(6) The compound of formula (I), wherein both $R^3$ and $R^4$ represent H; in an embodiment, one of $R^3$ and $R^4$ represents H, and the other represents halogen; in another embodiment, one of $R^3$ and $R^4$ represents H and the other represents F, Cl, methyl, or methoxy group; in still another embodiment, both $R^3$ and $R^4$ represent methyl; and in yet another embodiment, $R^3$ and $R^4$ are combined with each other to form —$R^3$—$R^4$—, and —$R^3$—$R^4$— forms a combination as ethylene or trimethylene to form cyclopropane-1,1-diyl or cyclobutane-1,1-diyl together with the carbon atom binding thereto.

Further, the present invention also includes compounds that are formed by combining the embodiments of the substituents shown in the above sections (1) to (6). For example, the present invention includes the following compounds or a pharmaceutically acceptable salt thereof.

(7) The compound of formula (I), wherein $R^1$ represents H, —O-(lower alkyl), —O-(halogen-lower alkyl), or aryl, heteroaryl, or cycloalkyl which may be respectively substituted with substituent(s) selected from $G^1$; $G^1$ represents halogen, —CN, —O-(lower alkyl), and lower alkyl; and $R^2$ represents H, lower alkyl, halogen, or cycloalkyl.

(8) The compound of formula (I), wherein $R^1$ represents phenyl, pyridyl, or cycloalkyl which may be respectively substituted with group(s) selected from $G^1$; $R^2$ represents halogen; m represents 1, n represents 1; and both $R^3$ and $R^4$ represent H.

(9) The compound of formula (I), wherein $R^1$ represents phenyl which may be substituted with halogen or —O-(lower alkyl); $R^2$ represents H, F, Cl, or methyl; m represents 1; n represents 1, and both $R^3$ and $R^4$ represent H.

(10) The compound of formula (I), wherein $R^1$ represents pyridyl which may be substituted with halogen or —O-(lower alkyl); $R^2$ represents H, F, Cl, or methyl; m represents 1; n represents 1; and both $R^3$ and $R^4$ represent H.

(11) The compound of formula (I), wherein $R^1$ represents phenyl which may be substituted with halogen or —O-(lower alkyl); $R^2$ represents H, F, Cl, or methyl; m represents 1; n represents 1; and $R^3$ and $R^4$ form cyclopropyl or cyclobutyl together with the carbon atom binding thereto, as a lower alkylene having 2 or more carbon atoms.

(12) A compound selected from the following group of compounds, or a pharmaceutically acceptable salt thereof.
N-(diaminomethylene)-5-fluoro-8-(2,4,6-trifluorophenyl)-3,4-dihydroisoquinoline-2(1H)-carboxamide,
N-(diaminomethylene)-8-(2,6-difluorophenyl)-5-fluoro-3,4-dihydroisoquinoline-2(1H)-carboxamide,
N-(diaminomethylene)-8-(3,5-difluoropyridin-2-yl)-5-fluoro-3,4-dihydroisoquinoline-2(1H)-carboxamide,
N-(diaminomethylene)-8-(3,5-difluoropyridin-2-yl)-5-methyl-3,4-dihydroisoquinoline-2(1H)-carboxamide,
N-(diaminomethylene)-8-(3,5-dichloropyridin-2-yl)-5-fluoro-3,4-dihydroisoquinoline-2(1H)-carboxamide,
N-(diaminomethylene)-5'-fluoro-8'-(2,4,5-trifluorophenyl)-1'H-spiro[cyclopropane-1,4'-isoquinoline]-2'(3'H)-carboxamide,
5-chloro-N-(diaminomethylene)-8-(2,4,6-trifluorophenyl)-3,4-dihydroisoquinoline-2(1H)-carboxamide,
8'-cyclopropyl-N-(diaminomethylene)-5'-fluoro-1'H-spiro[cyclopropane-1,4'-isoquinoline]-2'(3'H)-carboxamide,
N-(diaminomethylene)-5-fluoro-8-(2,4,5-trifluorophenyl)-3,4-dihydroisoquinoline-2(1H)-carboxamide,
N-(diaminomethylene)-8'-(2,6-difluorophenyl)-5'-fluoro-1'H-spiro[cyclopropane-1,4'-isoquinoline]-2'(3'H)-carboxamide,
N-(diaminomethylene)-5'-fluoro-8'-(2,4,6-trifluorophenyl)-1'H-spiro[cyclopropane-1,4'-isoquinoline]-2'(3'H)-carboxamide,
N-(diaminomethylene)-8'-(2,4-difluorophenyl)-5'-fluoro-1'H-spiro[cyclopropane-1,4'-isoquinoline]-2'(3'H)-carboxamide, and
N-(diaminomethylene)-5'-fluoro-8'-(2-fluorophenyl)-1'H-spiro[cyclopropane-1,4'-isoquinoline]-2'(3'H)-carboxamide.

Moreover, the present application further includes the following.

(13) A pharmaceutical composition comprising the compound of formula (I) or a pharmaceutically acceptable salt thereof and a pharmaceutically acceptable excipient.

(14) The pharmaceutical composition according to the section (13), which is a $5-HT_{5A}$ receptor regulator.

(15) The pharmaceutical composition according to the section (14), which is for treating or preventing dementia, schizophrenia, bipolar disorder, attention deficit hyperactivity disorder, or mood disorder.

(16) An agent for treating or preventing dementia, schizophrenia, bipolar disorder, attention deficit hyperactivity disorder, or mood disorder, which comprises the compound of formula (I) or a pharmaceutically acceptable salt thereof as an active ingredient.

(17) Use of the compound of formula (I) or a pharmaceutically acceptable salt thereof for the manufacture of a pharmaceutical composition for treating or preventing dementia, schizophrenia, bipolar disorder, attention deficit hyperactivity disorder, or mood disorder.

(18) Use of the compound of formula (I) or a pharmaceutically acceptable salt thereof for treating or preventing dementia, schizophrenia, bipolar disorder, attention deficit hyperactivity disorder, or mood disorder.

(19) The compound of formula (I) or a pharmaceutically acceptable salt thereof for treating or preventing dementia, schizophrenia, bipolar disorder, attention deficit hyperactivity disorder, or mood disorder.

(20) A method for treating or preventing dementia, schizophrenia, bipolar disorder, attention deficit hyperactivity disorder, or mood disorder, comprising administering a therapeutically effective amount of the compound of formula (I) or a pharmaceutically acceptable salt thereof to a subject. In addition, the "subject" refers to human or other animals that require the prevention or treatment of the above disease. An embodiment of the subject is human who requires the treatment or prevention of the diseases.

The schizophrenia includes positive symptoms, negative symptoms, cognitive disorder, and mood disorder.

The compound of formula (I) includes tautomers, conformational isomers, or optical isomers, in some cases depending on the type of substituents. In the present specification, sometimes the compound is described merely in a single embodiment of those isomers, but the present invention includes those isomers as well as an isolate or mixture of the isomers.

In addition, the present invention also includes pharmaceutically acceptable prodrugs of the compound of formula (I). The pharmaceutically acceptable prodrugs refer to compounds having a group that can be converted into an amino group, OH, $CO_2H$, and the like by solvolysis or under physiological conditions. Examples of groups forming the prodrugs include the groups disclosed in Prog. Med., 5, 2157-2161 (1985) or "Pharmaceutical research and development" (Hirokawa Publishing Company, 1990), Vol. 7, Drug Design, 163-198.

Moreover, the compound represented by the formula (I) may form an acid addition salt or a salt with a base depending on the type of substituents, and the salts are included in the present invention as long as they are pharmaceutically acceptable salts. Specific examples of the salts include acid addition salts with an inorganic acid such as hydrochloric acid, hydrobromic acid, hydriodic acid, sulfuric acid, nitric acid, or phosphoric acid, or with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, or glutamic acid, salts with an inorganic base such as sodium, potassium, magnesium, calcium, or aluminum, or with an organic base such as methylamine, ethylamine, ethanolamine, lysine, or ornithine, and ammonium salts.

Furthermore, the compound of formula (I) and a pharmaceutically acceptable salt thereof includes various hydrates, solvates and crystalline polymorphs. In addition, the compound of formula (I) and a pharmaceutically acceptable salt thereof also includes compounds labeled with various radioactive or non-radioactive isotopes.

(Preparation Process)

The compound of formula (I) and a pharmaceutically acceptable salt thereof can be prepared by applying various known synthetic methods, by utilizing the characteristics based on its basic skeleton or its type of substituents. Depending on the type of functional group, sometimes it is effective as a preparation technique to substitute the functional group with an appropriate protective group (a group that can be easily converted to said functional group) during the raw material to intermediate stage. Examples of such functional groups are amino group, hydroxyl group, carboxyl group, and the like, and examples of the protective groups thereof include the protective groups disclosed in Wuts (P. G. M. Wuts) and Greene (T. W. Greene), "Greene's Protective Groups in Organic Synthesis ($4^{th}$ edition, 2006)". These protective groups can be appropriately selected and used according to the reaction conditions. In this method, the protective group is removed if necessary after it has been introduced and the reaction carried out, in order to produce the desired compound.

In addition, prodrugs of the compound of formula (I) can be prepared by introducing a specific group during the raw material-to-intermediate stage, just like the above protective group, or by further causing a reaction by using the obtained compound of formula (I). The reaction can be performed by applying methods known to a person skilled in the art, such as general esterification, amidation, and dehydration.

Hereinafter, representative preparation processes of the compound of formula (I) will be described. Each preparation process can be performed with reference to the reference document included in the corresponding description. Moreover, the preparation process of the present invention is not limited to the following examples.

(Preparation Method 1)

[Chem. 8]

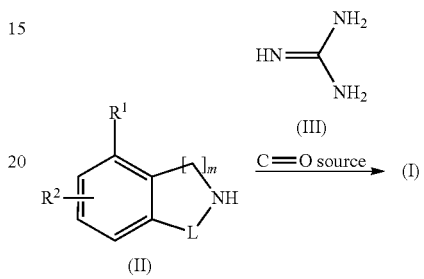

The compound of formula (I) can be prepared by reacting a compound (II) and guanidine (III) or a salt thereof with a C=O source compound.

Herein, the C=O source compound refers to a compound as an activated carbonic acid derivative, which forms the carbonyl moiety of the compound of formula (I). Examples of the C=O source compound include compounds obvious to a person skilled in the art, such as CDI (N,N'-carbonyldiimidazole), triphosgene, ethyl chlorocarbonate, and phenyl chlorocarbonate.

Moreover, as the guanidine (III), for example, guanidine carbonate or guanidine hydrochloride can be used.

The reaction can be carried out by using the compound (II), the guanidine (III), and the C=O source compound in an equivalent amount, or by using an excess amount of the guanidine (III) and the C=O source compound. The reaction can be performed in a solvent inert to the reaction, including aromatic hydrocarbons such as benzene, toluene, and xylene, halogenated hydrocarbons such as dichloromethane, 1,2-dichloroethane, and chloroform, ethers such as diethyl ether, tetrahydrofuran (THF), dioxane, and dimethoxyethane (DME), N,N-dimethylformamide (DMF), dimethyl sulfoxide (DMSO), or N-methylpyrrolidone (NMP), or in a mixture of these, under conditions ranging from cooling to heating, preferably at −20° C. to 80° C.

In addition, sometimes an appropriate base is required for performing the reaction. Examples of the base include organic bases such as triethylamine (TEA), diisopropylethylamine (DIPEA), N-methylmorpholine (NMM), pyridine, and 4-(N,N-dimethylamino)pyridine, and inorganic bases such as sodium methoxide and sodium hydrogen carbonate.

Furthermore, another compound of formula (I) can also be prepared by various transformation of substituents, using the compound of formula (I) as a starting material. Alternatively, from the compounds obtained by the above reaction, various types of pharmaceutically acceptable salts of the compound of formula (I) can also be prepared.

(Starting Material Synthesis 1)

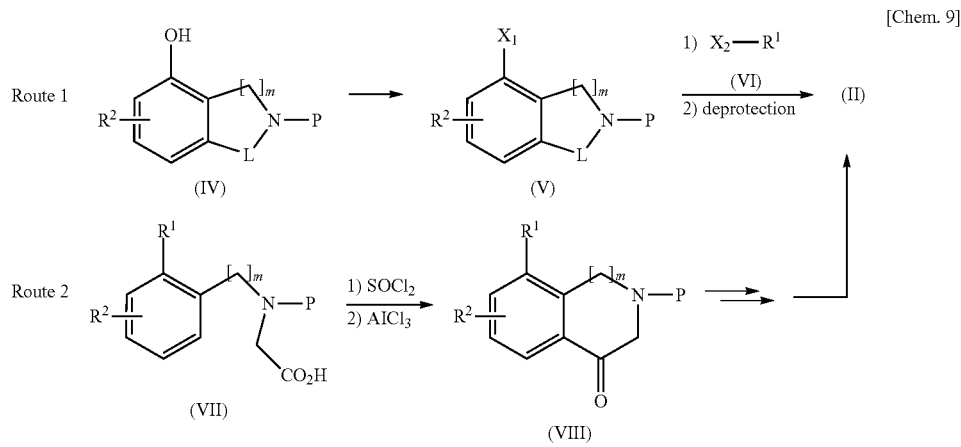

[Chem. 9]

(In the formula, $X^1$ represents trifluoromethanesulfonyloxy, halogen, methanesulfonyloxy, or p-toluenesulfonyloxy, or the like; and $X^2$ represents an active group such as —$B(OH)_2$, —B(OY)OW, or halogen. Herein, Y and W may be the same as or different from each other and represent a lower alkyl, or, Y and W are combined with each other to represent a lower alkylene. Moreover, P represents a protective group such as tert-butoxycarbonyl.)

The compound (II) can be prepared by the preparation process of the Route 1 or Route 2 shown in the above scheme.

In the preparation process of Route 1, compound (II) can be prepared by a coupling reaction of compound (V) and (VI), followed by deprotection. The compound (V) can be prepared by converting hydroxy group of the compound (IV) into an appropriate group $X^1$.

When $X^2$ represents an active group such as —$B(OH)_2$ or —B(OY)OW in the preparation process of Route 1, the compounds (V) and (VI) are used in an equivalent amount, or one of the compounds is used in an excess amount. The mixture of them is stirred generally for 0.1 hours to 5 days under conditions ranging from room temperature to heating under reflux in a solvent inert to the reaction, in the presence of a base and a palladium catalyst, whereby the reaction is performed. It is preferable that the reaction be performed in an inert gas atmosphere. Though not particularly limited, examples of the solvent used herein include aromatic hydrocarbons, ethers, halogenated hydrocarbons, alcohols such as methanol and ethanol, DMF, DMSO, and a mixture thereof. As the base, inorganic bases such as sodium carbonate, potassium carbonate, and sodium hydroxide are preferable. As the palladium catalyst, tetrakis(triphenylphosphine)palladium, dichlorobis(triphenylphosphine)palladium, palladium chloride-1,1'-bis(diphenylphosphino)ferrocene, tris(dibenzylideneacetone)dipalladium, and the like. As a phosphine ligand, tri(tert-butyl)phosphine, tricyclohexylphosphine, a 2-dicyclohexylphosphinobiphenyl derivative and the like can be used.

On the other hand, for $X^2$ represents halogen, compound (VI) is converted to an organolithium compound by using n-butyllithium, lithium diisopropylamide (LDA) or the like, followed by treatment with zinc chloride, to afford an organozinc compound in situ. The compound (II) can be prepared by the reaction of the obtained organozinc compound and compound (V) in a solvent inert to the reaction in the presence of a base and a palladium catalyst. The solvent, base, and palladium catalyst used herein can be the same as those for the reaction where $X^2$ represents an active group such as —$B(OH)_2$ or —B(OY)OW.

The coupling reaction can be performed with reference the following documents.

DOCUMENT

A. de Meijere and F. Diederich, "Metal-Catalyzed Cross-Coupling Reactions", 2nd edition, VCH Publishers Inc., 2004

"The Fifth Series of Experimental Chemistry", Vol. 13, edited by the Chemical Society of Japan, Maruzen, 2005

In the preparation process of Route 2, compound (VIII) is prepared by an intramolecular cyclization reaction of compound (VII), and then the compound (VIII) is subjected to various transformation of the substituents in order to form L of the compound (II), whereby the compound (II) can be prepared (for more detail, see the preparation examples described later).

Compound (VIII) can be prepared by the treatment of compound (VII) with an acid halide or anhydride and a Lewis acid, the reaction of which is the acylation of aromatic ring well known to a person skilled in the art.

(Starting Material Synthesis 2)

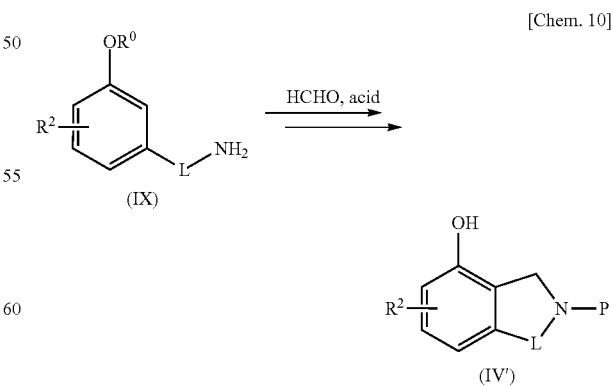

[Chem. 10]

(In the formula, $R^0$ represents a lower alkyl, for example, methyl. P represents a protective group of amino group, for example, t-butoxycarbonyl.)

A compound (IV') can be prepared, for example, in a process in which a compound (IX) is reacted with formaldehyde to form an imine, and an intramolecular cyclization reaction is performed under acidic conditions, followed by protection of the amino group and formation of a phenol.

In addition to the above mentioned intramolecular cyclization, compound (IV') can be prepared by applying various cyclization reaction to compound (VIII), the reaction of which is well known to a person skilled in the art (for more detail, see the preparation examples described later).

The compound of formula (I) prepared in this manner is isolated and purified as a free compound, a pharmaceutically acceptable salt thereof, a hydrate, a solvate, or a crystalline polymorph. A pharmaceutically acceptable salt of the compound of formula (I) can also be prepared by salt-formation reaction, which is a general technological knowledge of a person skilled in the art.

The isolation and purification are performed by applying general chemical operations such as extraction, fractional crystallization, and fractional chromatography.

Various kinds of isomers can be prepared by selecting appropriate raw materials, or can be separated by utilizing difference in physicochemical properties among the isomers. For example, the optical isomers can be isolated by general optical resolution (for example, by fractional crystallization to convert the compound into a diastereomer salt with an optically active base or acid, or by chromatography using a chiral column, or the like) of a racemic mixture. Alternatively, the optical isomers can also be prepared from appropriate starting compounds that are optically active.

EXAMPLES

Hereinafter, the preparation process of the compound of formula (I) will be described as Examples. In addition, the preparation process of compounds used as starting materials will be described as Preparation Examples. Moreover, the preparation process of the compound of formula (I) is not limited only to the preparation processes of specific Examples described below. The compound can also be prepared by a combination of those preparation processes or by a known preparation process. Furthermore, a concentration [M] indicates [mol/L].

Preparation Example 1

In an argon gas atmosphere, tris(dibenzylideneacetone)dipalladium (0) (558 mg) and tri-tert-butylphosphonium tetrafluoroborate (354 mg) were added to a mixed liquid of 4-bromo-1-fluoro-2-methoxybenzene (5.0 g), N-vinylformamide (2.6 g), N,N-dicyclohexylmethylamine (6.67 g), and dioxane (50 mL), followed by stirring for 16 hours at an oil temperature of 60° C. and cooling to room temperature. The reaction liquid was concentrated under reduced pressure, and the residue was purified by silica gel column chromatography (hexane/ethyl acetate), thereby obtaining N-[(E)-2-(4-fluoro-3-methoxyphenyl)vinyl]formamide (1.68 g).

Preparation Example 2

In an argon gas atmosphere, n-butyllithium (1.67 M hexane solution, 4.9 mL) was added to a THF solution (25 mL) of 3,5-dichloropyridine (1.0 g) at −78° C. After stirring for 30 minutes at the same temperature, chloro(trimethyl)silane (1.1 mL) was slowly added thereto, and the temperature was raised to room temperature, followed by stirring for 1 hour. Water and diethyl ether were added to the reaction liquid to perform liquid separation. The organic layer was washed with saturated aqueous sodium bicarbonate and saturated brine, followed by drying and then concentration under reduced pressure. The residue was purified by silica gel column chromatography (hexane/ethyl acetate), thereby obtaining 3,5-dichloro-4-(trimethylsilyl)pyridine (1.3 g).

Preparation Example 3

TEA (0.91 mL) was added to a dichloromethane (10 mL) solution of 5-fluoro-1,2,3,4-tetrahydroisoquinolin-8-ol hydrobromide (407 mg), and methyl chlorocarbonate (0.32 mL) was added thereto under ice cooling, followed by stirring for 1 hour at room temperature. Thereafter, 1 M aqueous sodium hydroxide solution (12 mL) and methanol (26 mL) were further added thereto, followed by stirring for 3 hours. After acidification with 1 M hydrochloric acid, ethyl acetate was added thereto. The organic layer obtained by performing liquid separation was washed with saturated brine, followed by drying and concentration under reduced pressure, thereby obtaining methyl 5-fluoro-8-hydroxy-3,4-dihydroisoquinoline-2(1H)-carboxylate (370 mg).

Preparation Example 4

10% Pd/C (55% water wet, 1.34 g) was added to an ethanol (35 mL) solution of N-[(E)-2-(4-fluoro-3-methoxyphenyl)vinyl]formamide (3.69 g), followed by stirring for 5 hours at room temperature in a hydrogen gas atmosphere. The reaction liquid was filtered through Celite, and the filtrate was concentrated under reduced pressure, thereby obtaining N-[2-(4-fluoro-3-methoxyphenyl)ethyl]formamide (3.05 g).

Preparation Example 5

N-bromosuccinimide (2.74 g) was added to an acetonitrile (55 mL) solution of N-[2-(4-fluoro-3-methoxyphenyl)ethyl]formamide (2.76 g), followed by stirring for 2 hours at room temperature. The reaction liquid was filtered, and the obtained solid was washed with acetonitrile and ethanol and then dried under reduced pressure, thereby obtaining N-[2-(2-bromo-4-fluoro-5-methoxyphenyl)ethyl]formamide (2.18 g).

Preparation Example 6

In an argon gas atmosphere, lithium diisopropylamide (2.0 M THF/heptane/ethyl benzene solution, 0.46 mL) was added to a THF solution (4 mL) of 3-chloro-5-fluoro-4-(trimethylsilyl)pyridine (157 mg) at −78° C., followed by stirring for 20 minutes at the same temperature. Chloro(trimethyl)silane (0.13 mL) was slowly added thereto, and then the temperature was raised to room temperature, followed by stirring for 1 hour. Water and diethyl ether were added to the reaction liquid to perform liquid separation. The organic layer was washed with saturated aqueous sodium bicarbonate and saturated brine, followed by drying and then concentration under reduced pressure. The residue was purified by silica gel column chromatography (hexane/chloroform), thereby obtaining 5-chloro-3-fluoro-2,4-bis(trimethylsilyl)pyridine (154 mg).

Preparation Example 7

DIPEA (0.84 mL) and 20% palladium hydroxide on carbon (280 mg) were added to an ethanol (9 mL) solution of 5-bromo-7-fluoro-8-methoxy-3,4-dihydroisoquinoline (1.26 g), followed by stirring for 3 hours at room temperature in a hydrogen gas atmosphere. The reaction liquid was filtered through Celite, and then the filtrate was concentrated under reduced pressure, thereby obtaining 7-fluoro-8-methoxy-1,2,3,4-tetrahydroisoquinoline (1.05 g).

Preparation Example 8

In an argon gas atmosphere, water (0.2 mL), tripotassium phosphate (560 mg), tricyclohexylphosphine (54 mg), palladium acetate (20 mg), and cyclopropylboronic acid (128 mg) were added to a toluene solution (5 mL) of tert-butyl 5-bromo-8-methoxy-3,4-dihydroisoquinoline-2(1H)-carboxylate (300 mg), followed by stirring for 16 hours at an oil temperature of 110° C. The reaction liquid was allowed to cool to room temperature and then filtered through Celite. Water and ethyl acetate were added to the filtrate to perform liquid separation. The organic layer was washed with saturated brine and dried, followed by concentration under reduced pressure. The residue was purified by silica gel column chromatography (hexane/ethyl acetate), thereby obtaining tert-butyl 5-cyclopropyl-8-methoxy-3,4-dihydroisoquinoline-2(1H)-carboxylate (183 mg).

Preparation Example 9

In an argon gas atmosphere, boron tribromide (1 M dichloromethane solution, 1.2 mL) was added dropwise to a dichloromethane solution (3 mL) of tert-butyl 5-cyclopropyl-8-methoxy-3,4-dihydroisoquinoline-2(1H)-carboxylate (182 mg) under ice cooling, followed by stirring for 1 hour at the same temperature. Water (1 mL) was added thereto, the solvent was evaporated under reduced pressure, and THF (2 mL) was added to the residue. TEA (0.5 mL) and di-tert-butyl dicarbonate (DIBOC, 190 mg) were added thereto under ice cooling, and the temperature was raised to room temperature, followed by stirring for 1.5 hours. The reaction liquid was concentrated under reduced pressure, and the residue was purified by silica gel column chromatography (hexane/ethyl acetate), thereby obtaining tert-butyl 5-cyclopropyl-8-hydroxy-3,4-dihydroisoquinoline-2(1H)-carboxylate (125 mg).

Preparation Example 10

4 M hydrogen chloride/ethyl acetate solution (10 mL) was added to an ethyl acetate solution (10 mL) of tert-butyl 5-chloro-8-(2,6-difluorophenyl)-3,4-dihydroisoquinoline-2(1H)-carboxylate (332 mg), followed by stirring for 15 hours at room temperature. The reaction liquid was concentrated under reduced pressure, thereby obtaining 5-chloro-8-(2,6-difluorophenyl)-1,2,3,4-tetrahydroisoquinoline hydrochloride (274 mg).

Preparation Example 11

In an argon gas atmosphere, tetrakis(triphenylphosphine) palladium (25 mg) and tripotassium phosphate (137 mg) were added to a mixture of tert-butyl 5-chloro-8-{[(trifluoromethyl)sulfonyl]oxy}-3,4-dihydroisoquinoline-2(1H)-carboxylate (90 mg), 3-methoxy-4-(4,4,5,5-tetramethyl-1,3,2-dioxaborolan-2-yl)benzonitrile (84 mg), and DMF (3.5 mL), followed by stirring for 20 hours at an oil temperature of 100° C., and then cooling to room temperature. Ethyl acetate and water were added to the reaction liquid to perform liquid separation. The organic layer was washed with saturated brine and dried, followed by concentration under reduced pressure. The residue was purified by silica gel column chromatography (hexane/ethyl acetate), thereby obtaining tert-butyl 5-chloro-8-(4-cyano-2-methoxyphenyl)-3,4-dihydroisoquinoline-2(1H)-carboxylate (73 mg).

Preparation Example 12

A 50% aqueous sodium hydroxide solution (18 mL) was slowly added to a mixture of (2-fluoro-5-methoxyphenyl)acetonitrile (3.0 g), 1-bromo-2-chloroethane (5.2 g), and benzyltriethylammonium chloride (104 mg) under ice cooling, followed by stirring for 1 day at an oil temperature of 40° C. The reaction liquid was allowed to cool to room temperature, and then ice water and toluene were added thereto to perform liquid separation. The organic layer was washed with saturated brine and then dried, followed by concentration under reduced pressure. The residue was purified by silica gel column chromatography (hexane/ethyl acetate), thereby obtaining 1-(2-fluoro-5-methoxyphenyl)cyclopropanecarbonitrile (3.54 g).

Preparation Example 13

A borane-THF complex (1 M THF solution, 21 mL) was added to a mixture of 1-(2-fluoro-5-methoxyphenyl)cyclopropanecarbonitrile (3.54 g) and THF (70 mL), followed by stirring for 5 hours under heating at an oil temperature of 80° C. After being left to cool to room temperature, the reaction liquid was concentrated under reduced pressure, methanol (30 mL) was added thereto, and the solvent was evaporated under reduced pressure. This operation was further repeated twice. 1 M hydrochloric acid (30 mL) was added to the residue, followed by stirring for 30 minutes under heating at an oil temperature of 60° C. and washing with diethyl ether. 1 M aqueous sodium hydroxide solution was added to the aqueous layer to adjust the pH to about 9, and then extraction was performed with chloroform, followed by concentration under reduced pressure, thereby obtaining 1-[1-(2-fluoro-5-methoxyphenyl)cyclopropyl]methanamine (4.0 g).

Preparation Example 14

Formic acid (1.4 g) was added to a mixture of 1-[1-(2-fluoro-5-methoxyphenyl)cyclopropyl]methanamine (4.0 g) and toluene (39 mL), followed by stirring for 2 days with heating under reflux. After being allowed to cool to room temperature, the reaction liquid was concentrated under reduced pressure, and water and ethyl acetate were added to the residue to perform liquid separation. The organic layer was dried and concentrated under reduced pressure, thereby obtaining N-{[1-(2-fluoro-5-methoxyphenyl)cyclopropyl]methyl}formamide (4.57 g).

Preparation Example 15

Oxalyl chloride (8.5 g) was added to a mixture of N-{[1-(2-fluoro-5-methoxyphenyl)cyclopropyl]methyl}formamide (3.0 g) and dichloromethane (36 mL) under ice cooling, followed by stirring for 1 hours at room temperature. Iron(III) chloride (2.6 g) was added thereto under ice cooling, followed by stirring again for 1 day at room temperature. 1 M hydrochloric acid (100 mL) was added to the reaction liquid, followed by stirring for 30 minutes and filtration. Saturated aqueous sodium bicarbonate was added to the filtrate for neutralization, and chloroform was added thereto to perform liquid separation. The organic layer was concentrated under reduced pressure, methanol (100 mL) and saturated sulfuric acid (5 mL) were added to the residue, followed by stirring for 1 day with heating under reflux and then cooling to room temperature. The reaction liquid was concentrated under reduced pressure, and 1M hydrochloric acid and ethyl acetate were added to the residue to perform liquid separation. A saturated aqueous ammonia solution was added to the aqueous layer, and chloroform was added thereto to perform liquid separation. The organic layer was dried and concentrated under reduced pressure, thereby obtaining 5'-fluoro-8'-methoxy-3'H-spiro[cyclopropane-1,4-isoquinoline] (2.8 g).

Preparation Example 16

In an argon gas atmosphere, bis(dibenzylideneacetone)palladium (52 mg) and tri-tert-butylphosphonium tetrafluoroborate (53 mg) were added to a mixture of methyl 2,6-dichlorophenylacetate (2.00 g), N-vinylformamide (1.32 g), dicyclohexylmethylamine (1.96 g), and N-methylpyrrolidone (10 mL), followed by stirring for 1 day under heating at 135° C. DIPEA (1.18 g) was added to the reaction liquid, followed by stirring again for 1 day at the same temperature. The reaction liquid was cooled to room temperature, and water and ethyl acetate were added thereto to perform liquid separation. The organic layer was concentrated under reduced pressure, and the residue was purified by silica gel column chromatography (hexane/ethyl acetate), thereby obtaining 9-chloro-1,3-dihydro-2H-3-benzazepin-2-one (1.10 g).

Preparation Example 17

10% Pd/C (110 mg) was added to an acetic acid (5 mL) solution of 9-(4-fluorophenyl)-1,3-dihydro-2H-3-benzazepin-2-one (68 mg), followed by stirring overnight at room temperature in a hydrogen gas atmosphere at 3 atm. The reaction liquid was filtered through Celite, and the filtrate was concentrated under reduced pressure. The residue was purified by silica gel column chromatography (chloroform/methanol), thereby obtaining 9-(4-fluorophenyl)-1,3,4,5-tetrahydro-2H-3-benzazepin-2-one (35 mg).

Preparation Example 18

A borane-THF complex (1 M THF solution, 0.56 mL) was added to a mixture of 9-(4-fluorophenyl)-1,3,4,5-tetrahydro-2H-3-benzazepin-2-one (31 mg) and THF (10 mL), followed by heating under reflux for 5 hours. After the reaction liquid was cooled to room temperature, methanol (10 mL) was added thereto, and the reaction liquid was concentrated under reduced pressure. 1 M hydrochloric acid (10 mL) was added to the residue, followed by stirring for 30 minutes under heating at an oil temperature of 60° C. After the reaction liquid was allowed to cool to room temperature, a saturated aqueous ammonia solution and chloroform were added thereto to perform liquid separation. The organic layer was concentrated under reduced pressure, thereby obtaining 6-(4-fluorophenyl)-2,3,4,5-tetrahydro-1H-3-benzazepine (36 mg).

Preparation Example 19

Lithium diisopropylamide (2.0 M THF/heptane/ethyl benzene solution, 16.5 mL) was added to a mixture of (2-fluoro-5-methoxyphenyl)acetonitrile (5.2 g) and THF (100 mL) under cooling at −78° C., followed by stirring for 1 hour. Methyl iodide (4.5 g) was added thereto at the same temperature, and the temperature was raised to room temperature, followed by stirring for 3 days. A saturated aqueous ammonium chloride solution was added thereto for neutralization, and then the reaction liquid was concentrated under reduced pressure. Water and ethyl acetate were added to the residue to perform liquid separation. The organic layer was dried and concentrated under reduced pressure, followed by purification by silica gel column chromatography, thereby obtaining 2-(2-fluoro-5-methoxyphenyl)propanenitrile (4.0 g).

Preparation Example 20

A THF (37 mL) solution of (2-fluoro-5-methoxyphenyl)acetonitrile (5.0 g) was added to a mixture of 55% sodium hydride (3.3 g) and THF (100 mL), followed by stirring for 1 hour at room temperature, and then methyl iodide (9.8 g) was added thereto, followed by stirring for 1 day. Ethyl acetate and water were added to the reaction liquid to perform liquid separation. The organic layer was concentrated under reduced pressure, and the residue was purified by silica gel column chromatography (hexane/ethyl acetate), thereby obtaining 2-(2-fluoro-5-methoxyphenyl)-2-methylpropionitrile (5.0 g).

Preparation Example 21

DIBOC (1.15 g) and TEA (1.60 g) were added to a mixture of 5-fluoro-4,4-dimethyl-1,2,3,4-tetrahydroisoquinolin-8-ol hydrobromide (1.45 g) and THF (50 mL), followed by stirring for 3 days at room temperature. The reaction liquid was concentrated under reduced pressure, and 1 M hydrochloric acid and ethyl acetate were added to the residue to perform liquid separation. The organic layer was concentrated under reduced pressure, and the residue was purified by silica gel column chromatography (hexane/ethyl acetate), thereby obtaining tert-butyl 5-fluoro-8-hydroxy-4,4-dimethyl-3,4-dihyroisoquinoline-2(1H)-carboxylate (764 mg).

Preparation Example 22

55% sodium hydride (12 mg) was added to a mixture of tert-butyl 5-fluoro-8-hydroxy-4,4-dimethyl-3,4-dihyroisoquinoline-2(1H)-carboxylate (70 mg) and N-methylpyrrolidone (1 mL), followed by stirring for 10 minutes at room temperature. Thereafter, 2,2,2-trifluoroethyl 4-methylbenzenesulfonate (72 mg) was added thereto, followed by stirring for 15 minutes at 150° C. under microwave irradiation. The reaction liquid was cooled to room temperature, and water and ethyl acetate were added thereto to perform liquid separation. The organic layer was concentrated under reduced pressure, and the residue was purified by silica gel column chromatography (hexane/ethyl acetate), thereby obtaining tert-butyl 5-fluoro-4,4-dimethyl-8-(2,2,2-trifluoroethoxy)-3,4-dihydroisoquinoline-2(1H)-carboxylate (67 mg).

Preparation Example 23

In an argon gas atmosphere, lithium diisopropylamide (2.0 M THF/heptane/ethyl benzene solution, 0.95 mL) was added to a mixture of 3,5-difluoro-4-(trimethylsilyl)pyridine (340 mg) and THF (2.9 mL) under cooling at −78° C., followed by stirring for 1 hour at the same temperature. Subsequently, zinc(II) chloride (0.5 M THF solution, 3.9 mL) was added thereto under cooling at −78° C., followed by stirring for 0.5 hours at the same temperature, and the temperature was raised to room temperature. A THF (1 mL) solution of methyl 5-fluoro-8-{[(trifluoromethyl)sulfonyl]oxy}-3,4-dihyroisoquinoline-2(1H)-carboxylate (130 mg), and tetrakis (triphenylphosphine)palladium (105 mg) were added to the reaction liquid, followed by stirring for 15 hours under heating at an oil temperature of 60° C. The reaction liquid was cooled to room temperature, and 1 M hydrochloric acid and ethyl acetate were added thereto to perform liquid separation. The organic layer was dried and concentrated under reduced pressure, and the residue was purified by silica gel column chromatography (hexane/ethyl acetate), thereby obtaining methyl 8-[3,5-difluoro-4-(trimethylsilyl)pyridine-2-yl]-5-fluoro-3,4-dihydroisoquinoline-2(1H)-carboxylate (60 mg).

Preparation Example 24

Tetrabutylammonium fluoride (1 M THF solution, 0.23 mL) was added to a mixture of methyl 8-[3,5-difluoro-4-(trimethylsilyl)pyridine-2-yl]-5-fluoro-3,4-dihydroisoquinoline-2(1H)-carboxylate (60 mg) and THF (1.2 mL), followed by stirring overnight at room temperature. Water and ethyl acetate were added to the reaction liquid to perform liquid separation. The organic layer was washed with saturated brine and then concentrated under reduced pressure, and the residue was purified by silica gel column chromatography (hexane/ethyl acetate), thereby obtaining methyl 8-(3,5-difluoropyridin-2-yl)-5-fluoro-3,4-dihydroisoquinoline-2(1H)-carboxylate (37 mg).

Preparation Example 25

A mixture of methyl 8-(3,5-difluoropyridin-2-yl)-5-fluoro-3,4-dihydroisoquinoline-2(1H)-carboxylate (37 mg) and 6 M hydrochloric acid (3.6 mL) was stirred overnight at an oil temperature of 120° C. and then cooled to room temperature. The reaction liquid was concentrated under reduced pressure, and the residue was washed with ethyl acetate, thereby obtaining 8-(3,5-difluoropyridin-2-yl)-5-fluoro-1,2,3,4-tetrahydroisoquinoline hydrochloride (30 mg).

Preparation Example 26

In an argon gas atmosphere, n-butyllithium (2.6 M hexane solution, 0.77 mL) was added to a mixture of 3,5-difluoropyridine (225 mg) and THF (4.2 mL) under cooling at −78° C., followed by stirring for 0.5 hours at the same temperature. Thereafter, zinc(II) chloride (277 mg) was added thereto under cooling at −78° C., followed by stirring for 0.5 hours at the same temperature, and then the temperature was raised to room temperature. An N-methylpyrrolidone (5.6 mL) solution of methyl 5-fluoro-8-{[(trifluoromethyl)sulfonyl]oxy}-3,4-dihydroisoquinoline-2(1H)-carboxylate (140 mg), and tetrakis(trifluorophosphine)palladium (90 mg) were added to the reaction liquid, followed by stirring for 15 hours under heating at an oil temperature of 100° C. After the reaction liquid was cooled to room temperature, 1 M hydrochloric acid and ethyl acetate were added thereto to perform liquid separation. The organic layer was washed with water and then dried, followed by concentration under reduced pressure. The residue was purified by silica gel column chromatography (hexane/ethyl acetate), thereby obtaining methyl 8-(3,5-difluoropyridin-4-yl)-5-fluoro-3,4-dihyroisoquinoline-2(1H)-carboxylate (112 mg).

Preparation Example 27

In an argon gas atmosphere, tetrakis(triphenylphosphine) palladium (76 mg) and TEA (199 mg) were added to a mixture of tert-butyl 8-{[(trifluoromethyl)sulfonyl]oxy}-3,4-dihydroisoquinoline-2(1H)-carboxylate (250 mg), 2,3-difluorophenyl boronic acid (207 mg), and dioxane (12.5 mL), followed by stirring for 12 hours at an oil temperature of 100° C. The reaction liquid was cooled to room temperature and concentrated under reduced pressure. The residue was purified by silica gel column chromatography (hexane/ethyl acetate), thereby obtaining tert-butyl 8-(2,3-difluorophenyl)-3,4-dihydroisoquinoline-2(1H)-carboxylate (223 mg).

Preparation Example 28

Trifluoroacetic acid (0.5 mL) was added to a mixture of tert-butyl 8-(2,3-difluorophenyl)-3,4-dihydroisoquinoline-2(1H)-carboxylate (223 mg) and dichloromethane (5 mL), followed by stirring for 3 hours at room temperature. A saturated aqueous sodium bicarbonate and ethyl acetate were added to the reaction liquid to perform liquid separation. The organic layer was washed with water and saturated brine in this order, and then dried, followed by concentration under reduced pressure, thereby obtaining 8-(2,3-difluorophenyl)-1,2,3,4-tetrahydroisoquinoline (137 mg).

Preparation Example 29

Pivaloyl chloride (2.19 g) was added to a mixture of 2-(3-methoxyphenyl)-2-methylpropane-1-amine (2.17 g), potassium carbonate (3.35 g), benzyl triethylammonium bromide (165 mg), ethyl acetate (10 mL), and water (10 mL) under ice cooling, followed by stirring for 1 hour at room temperature. Ethyl acetate was added to the reaction liquid to perform liquid separation. The organic layer was washed with 1 M hydrochloric acid, saturated aqueous sodium bicarbonate, and saturated brine in this order, and then dried, followed by concentration under reduced pressure, thereby obtaining N-[2-(3-methoxyphenyl)-2-methylpropyl]-2,2-dimethylpropanamide (3.13 g).

Preparation Example 30

In an argon gas atmosphere, a mixture of n-butyllithium (1.65 M hexane solution, 21.6 mL) and diethyl ether (40 mL) was added to a mixture of N-[2-(3-methoxyphenyl)-2-methylpropyl]-2,2-dimethylpropanamide (3.13 g) and diethyl ether (20 mL) under cooling at −78° C., followed by stirring for 2 hours at room temperature. Thereafter, DMF (6.4 mL) was added thereto under cooling at −78° C., followed by stirring for 3 hours at room temperature. 4 M hydrochloric acid (200 mL) was added to the reaction liquid, followed by stirring for 18 hours at room temperature. The aqueous layer was separated, and sodium hydroxide (2.8 g) and ethyl acetate were added thereto to perform liquid separation. The organic layer was washed with saturated brine and then dried, followed by concentration under reduced pressure, thereby obtaining 8-methoxy-4,4-dimethyl-3,4-dihydroisoquinoline (1.3 g).

Preparation Example 31

Sodium borohydride (520 mg) was added to a mixture of 8-methoxy-4,4-dimethyl-3,4-dihydroisoquinoline (1.3 g) and ethanol (13 mL) under ice cooling, followed by stirring for 1 hour at room temperature. Water and chloroform were added to the reaction liquid to perform liquid separation. The organic layer was washed with saturated brine and then dried, followed by concentration under reduced pressure, thereby obtaining 8-methoxy-4,4-dimethyl-1,2,3,4-tetrahydroisoquinoline (1.15 g).

Preparation Example 32

A mixture of 8-methoxy-4,4-dimethyl-1,2,3,4-tetrahydroisoquinoline (1.15 g) and 47% hydrobromic acid (20 mL) was stirred for 7 hours at an oil temperature of 120° C. After being cooled to room temperature, the reaction liquid was concentrated under reduced pressure, thereby obtaining 4,4-dimethyl-1,2,3,4-tetrahydroisoquinolin-8-ol hydrobromide (1.51 g).

Preparation Example 33

A 1 M aqueous sodium hydroxide solution (6.45 mL) and DIBOC (1.54 g) were added to a mixture of 4,4-dimethyl-1,2,3,4-tetrahydroisoquinolin-8-ol hydrobromide (1.51 g), THF (18 mL), and water (6 mL), followed by stirring for 1 day at room temperature. A saturated aqueous ammonium chloride solution and ethyl acetate were added to the reaction mixture to perform liquid separation. The organic layer was dried and then concentrated under reduced pressure, and the residue was purified by silica gel column chromatography (chloroform/ethyl acetate), thereby obtaining tert-butyl 8-hydroxy-4,4-dimethyl-3,4-dihydroisoquinoline-2(1H)-carboxylate (1.35 g).

Preparation Example 34

Trifluoromethanesulfonic anhydride (1.1 mL) was added to a mixture of tert-butyl 8-hydroxy-4,4-dimethyl-3,4-dihydroisoquinoline-2(1H)-carboxylate (1.35 g), TEA (2.2 mL), and dichloromethane (30 mL) under ice cooling, followed by stirring for 5 hours at room temperature. Water and chloroform were added to the reaction liquid to perform liquid separation. The organic layer was dried and then concentrated under reduced pressure, and the residue was purified by silica gel column chromatography (hexane/ethyl acetate), thereby obtaining tert-butyl 4,4-dimethyl-8-{[(trifluoromethyl)sulfonyl]oxy}-3,4-dihydroisoquinoline-2(1H)-carboxylate (1.15 g).

Preparation Example 35

A mixture of 2-(2-fluoro-5-methoxyphenyl)ethanamine (1.48 g), water (1.1 mL), and a 37% aqueous formaldehyde solution (0.85 g) was stirred for 1 hour at an oil temperature of 50° C. Concentrated hydrochloric acid (2.1 mL) was added to the reaction liquid, followed by stirring for 2 hours at an oil temperature of 110° C. After the reaction liquid was cooled to room temperature, a saturated aqueous sodium bicarbonate and chloroform were added thereto to perform liquid separation. The organic layer was dried and then concentrated under reduced pressure, and the residue was purified by NH silica gel column chromatography (chloroform/methanol) then purified by silica gel column chromatography (chloroform/methanol), thereby obtaining 5-fluoro-8-methoxy-1,2,3,4-tetrahydroisoquinoline (353 mg).

Preparation Example 36

In an argon gas atmosphere, tetrakis(triphenylphosphine)palladium (91 mg) and tripotassium phosphate (340 mg) were added to a mixture of tert-butyl 8-{[(trifluoromethyl)sulfonyl]oxy}-3,4-dihydroisoquinoline-2(1H)-carboxylate (300 mg), 2-chloro-6-fluorophenyl boronic acid (280 mg), and DMF (5 mL), followed by stirring for 11 hours at an oil temperature of 100° C. After the reaction liquid was cooled to room temperature, ethyl acetate and a saturated aqueous sodium bicarbonate were added thereto to perform liquid separation. The organic layer was washed with saturated brine and dried, followed by concentration under reduced pressure. The residue was purified by silica gel column chromatography (hexane/ethyl acetate), thereby obtaining tert-butyl 8-(2-chloro-6-fluorophenyl)-3,4-dihydroisoquinoline-2(1H)-carboxylate (145 mg).

Preparation Example 37

In an argon gas atmosphere, tetrakis(triphenylphosphine)palladium (61 mg) and DIPEA (203 mg) were added to a mixture of tert-butyl 8-{[(trifluoromethyl)sulfonyl]oxy}-3,4-dihydroisoquinoline-2(1H)-carboxylate (200 mg), 3-methoxy-4-(4,4,5,5-tetramethyl-1,3,2-dioxaborolan-2-yl)benzonitrile (272 mg), and dioxane (10 mL), followed by stirring for 18 hours at an oil temperature of 100° C. The reaction liquid was cooled to room temperature and then concentrated under reduced pressure, and the residue was purified by silica gel column chromatography (hexane/ethyl acetate), thereby obtaining tert-butyl 8-(4-cyano-2-methoxyphenyl)-3,4-dihydroisoquinoline-2(1H)-carboxylate (70 mg).

Preparation Example 38

A mixture of 8-(2,4,6-trifluorophenyl)isoquinoline (490 mg), platinum oxide (21 mg), ethanol (20 mL), and concentrated hydrochloric acid (2 mL) was stirred for 1 day at room temperature in a hydrogen gas atmosphere at 3 atm. The reaction liquid was filtered through Celite, and the filtrate was concentrated under reduced pressure, thereby obtaining 8-(2,4,6-trifluorophenyl)-1,2,3,4-tetrahydroisoquinoline hydrochloride (549 mg).

Preparation Example 39

In an argon gas atmosphere, tetrakis(triphenylphosphine)palladium (83 mg) and a 2 M aqueous sodium carbonate solution (2.2 mL) were added to a mixture of 8-bromoisoquinoline (300 mg), 2,4-difluorophenylboronic acid (342 mg), 1,2-dimethoxyethane (10 mL), and ethanol (1 mL), followed by stirring for 18 hours at an oil temperature of 100° C. The reaction liquid was cooled to room temperature, and then water and ethyl acetate were added thereto to perform liquid separation. The organic layer was washed with saturated brine and then dried, followed by concentration under reduced pressure. The residue was purified by silica gel column chromatography (hexane/ethyl acetate), thereby obtaining 8-(2,4-difluorophenyl)isoquinoline (312 mg).

Preparation Example 40

Deoxo-Fluor (registered trademark) (157 mg) was added to a mixture of tert-butyl 8-(2,4-difluorophenyl)-4-hydroxy-3,4-dihydroisoquinoline-2(1H)-carboxylate (140 mg) and dichloromethane (5 mL) under ice cooling, followed by stirring for 1 hour at the same temperature. Water and chloroform were added to the reaction liquid to perform liquid separation. The organic layer was concentrated under reduced pressure, and the residue was purified by silica gel column chromatography (hexane/ethyl acetate), thereby obtaining tert-butyl 8-(2,4-difluorophenyl)-4-fluoro-3,4-dihydroisoquinoline-2(1H)-carboxylate (49 mg).

Preparation Example 41

1 M aqueous sodium hydroxide solution (60 mL) was added to a mixture of ethyl N-[(2',4'-difluorobiphenyl-2-yl)

methyl]-N-[(4-methylphenyl)sulfonyl]glycinate (8.10 g), THF (60 mL), and ethanol (30 mL), followed by stirring for 15 hours at room temperature. The reaction liquid was neutralized with 1 M hydrochloric acid, and the generated solid was collected by filtration, thereby obtaining N-[(2',4'-difluorobiphenyl-2-yl)methyl]-N-[(4-methylphenyl)sulfonyl]glycine (7.32 g).

Preparation Example 42

55% sodium hydride (26 mg) was added to a mixture of tert-butyl 8-(2,4-difluorophenyl)-4-hydroxy-3,4-dihyroisoquinoline-2(1H)-carboxylate (192 mg), iodomethane (377 mg), and THF (10 mL) under ice cooling, followed by stirring for 3 hours at room temperature. A saturated aqueous sodium bicarbonate and ethyl acetate were added to the reaction liquid to perform liquid separation. The organic layer was concentrated under reduced pressure, and the residue was purified by silica gel column chromatography (hexane/ethyl acetate), thereby obtaining tert-butyl 8-(2,4-difluorophenyl)-4-methoxy-3,4-dihydroisoquinoline-2(1H)-carboxylate (102 mg).

Preparation Example 43

In an argon gas atmosphere, a mixture of tert-butyl 4-chloro-1,3-dihyrdo-2H-isoindole-2-carboxylate (200 mg), 4-fluorophenylboronic acid (221 mg), palladium(II) acetate (9 mg), dicyclohexyl(2',6'-dimethoxybiphenyl-2-yl)phosphine (32 mg), tripotassium phosphate (335 mg), and toluene (6 mL) was stirred for 20 hours at 100° C. After the reaction liquid was cooled to room temperature, water was added thereto, and the reaction liquid was filtered through Celite to perform liquid separation. The organic layer was dried and then concentrated under reduced pressure, and the residue was purified by silica gel column chromatography (hexane/ethyl acetate), thereby obtaining tert-butyl 4-(4-fluorophenyl)-1,3-dihydro-2H-isoindole-2-carboxylate (128 mg).

Preparation Example 44

A mixture of 8-(2,4-difluorophenyl)-5-fluoro-2-[(4-methylphenyl)sulfonyl]-1,2,3,4-tetrahydroisoquinolin-4-ol (325 mg) and THF (5 mL) was added to a mixture of lithium aluminum hydride (85 mg) and THF (5 mL), followed by stirring for 2 days at an oil temperature of 60° C. The reaction liquid was cooled to room temperature, and then water (0.1 mL), a 2 M aqueous sodium hydroxide solution (0.1 mL), and water (0.3 mL) were added thereto in this order, followed by filtration. The filtrate was concentrated under reduced pressure, thereby obtaining 8-(2,4-difluorophenyl)-5-fluoro-1,2,3,4-tetrahydroisoquinolin-4-ol (209 mg).

Preparation Example 45

Sodium borohydride (127 mg) was added to a mixture of 8-bromo-5-fluoro-2-[(4-methylphenyl)sulfonyl]-2,3-dihydroisoquinolin-4(1H)-one (1.34 g) and methanol (30 mL), followed by stirring for 1 hour at room temperature. Water and ethyl acetate were added to the reaction liquid to perform liquid separation. The organic layer was dried and then concentrated under reduced pressure, and the residue was purified by silica gel column chromatography, thereby obtaining 8-bromo-5-fluoro-2-[(4-methylphenyl)sulfonyl]-1,2,3,4-tetrahydroisoquinolin-4-ol (1.24 g).

Preparation Example 46

Thionyl chloride (3 mL) was added to a mixture of N-(2-bromo-5-fluorobenzyl)-N-[(4-methylphenyl)sulfonyl]glycine (5.39 g) and dichloromethane (60 mL), followed by heating under reflux for 2 hours. After being cooled to room temperature, the reaction liquid was concentrated under reduced pressure. In an argon gas atmosphere, dichloromethane (150 mL) was added to the residue, aluminum chloride (4.5 g) was added thereto under cooling at −78° C., and the temperature was raised to −15° C. over 4 hours, followed by stirring for 12 hours. Subsequently, methanol was added thereto, followed by stirring for 30 minutes at room temperature. Water and chloroform were added to the reaction liquid to perform liquid separation. The organic layer was concentrated under reduced pressure, and the residue was purified by silica gel column chromatography, thereby obtaining 8-bromo-5-fluoro-2-[(4-methylphenyl)sulfonyl]-2,3-dihydroisoquinolin-4(1H)-one (1.34 g).

Preparation Example 47

4-Methylbenzenesulfonyl chloride (5.45 g) was added to a mixture of ethyl N-(2-bromo-5-fluorobenzyl)glycinate (5.58 g), 4-dimethylaminopyridine (117 mg), TEA (5.6 mL), and dichloromethane (140 mL) under ice cooling, followed by stirring for 15 hours at room temperature. Hydrochloric acid and chloroform were added thereto to perform liquid separation. The organic layer was concentrated under reduced pressure, and the residue was purified by silica gel column chromatography (hexane/ethyl acetate), thereby obtaining ethyl N-(2-bromo-5-fluorobenzyl)-N-[(4-methylphenyl)sulfonyl]glycinate (5.85 g).

Preparation Example 48

In an argon gas atmosphere, a mixture of 8-(2,4-difluorophenyl)isoquinolin-4-yl trifluoromethanesulfonate (300 mg), 2,4,6-trivinylcyclotriboroxane-pyridine complex (185 mg), tetrakis(triphenylphosphine)palladium (45 mg), TEA (195 mg), and dioxane (6 mL) was stirred overnight at an oil temperature of 95° C. After being cooled to room temperature, the reaction liquid was concentrated under reduced pressure, and water and ethyl acetate were added to the residue to perform liquid separation. The organic layer was concentrated under reduced pressure, and the residue was purified by silica gel column chromatography, thereby obtaining 8-(2,4-difluorophenyl)-4-biphenylisoquinoline (110 mg).

Preparation Example 49

A mixture of 4-chloro-2',4'-difluorobiphenyl-2-carbaldehyde (4.40 g), glycine ethyl ester hydrochloride (3.16 g), sodium acetate (2.14 g), and dichloromethane (100 mL) was stirred for 1 hour at room temperature. Sodium triacetoxyborohydride (7.38 g) was added to the reaction liquid, followed by stirring for 18 hours at room temperature. Water and chloroform were added to the reaction liquid to perform liquid separation. The organic layer was dried and then concentrated under reduced pressure, the residue was purified by silica gel column chromatography (hexane/ethyl acetate), thereby obtaining ethyl N-[(4-chloro-2',4'-difluorophenyl-2-yl)methyl]glycinate (4.46 g).

Preparation Example 50

In an argon gas atmosphere, a mixture of 8-(2,4-difluorophenyl)isoquinolin-4-yl trifluoromethanesulfonate (281 mg), trimethylboroxine (91 mg), tetrakis(triphenylphosphine)palladium (25 mg), potassium carbonate (500 mg), dioxane (8 mL), and water (2 mL) was stirred for 2 hours at an oil temperature of 110° C. After the reaction liquid was cooled to room temperature, water and ethyl acetate were added thereto to perform liquid separation. The organic layer was washed with saturated brine and then dried, followed by concentration under reduced pressure, and the residue was purified by silica gel column chromatography, thereby obtaining 8-(2,4-difluorophenyl)-4-methylisoquinoline (56 mg).

Preparation Example 51

Pyridine (0.35 mL) and trifluoromethanesulfonic anhydride (0.7 mL) were added to a mixture of 8-(2,4-difluorophenyl)isoquinolin-4-ol (500 mg) and dichloromethane (20 mL), followed by stirring for 5 hours at room temperature. Water and chloroform were added to the reaction liquid to perform liquid separation. The organic layer was washed with saturated brine and then dried, followed by concentration under reduced pressure. The residue was purified by silica gel column chromatography (hexane/chloroform), thereby obtaining 8-(2,4-difluorophenyl)isoquinolin-4-yl trifluoromethanesulfonate (300 mg).

Preparation Example 52

A mixture of 8-(2,4-difluorophenyl)-2-[(4-methylphenyl)sulfonyl]-2,3-dihydroisoquinolin-4(1H)-one (3.00 g), saturated aqueous sodium bicarbonate (200 mL), and ethanol (40 mL) was heated under reflux for 1 day. After the reaction liquid was cooled to room temperature, water and ethyl acetate were added thereto to perform liquid separation. The organic layer was dried and then concentrated under reduced pressure, thereby obtaining 8-(2,4-difluorophenyl)isoquinolin-4-ol (1.43 g).

Preparation Example compounds shown in the tables described later were prepared in the same manner as in the above Preparation Examples, by using each of the corresponding raw materials. In addition, the structural formulas, physicochemical data, and preparation methods of the Preparation Example compounds will be shown in the tables described later.

Example 1

TEA (83 mg) and CDI (100 mg) were added to a mixture of 8-(2,4-difluorophenyl)-4-ethyl-1,2,3,4-tetrahydroisoquinoline hydrochloride (127 mg) and DMF (6 mL), followed by stirring for 30 minutes at an oil temperature of 60° C. After the reaction liquid was cooled to room temperature, guanidine carbonate (185 mg) was added thereto, followed by stirring for 3 hours at an oil temperature of 100° C. After the reaction liquid was cooled to room temperature, water and ethyl acetate were added thereto to perform liquid separation. The organic layer was concentrated under reduced pressure, and the residue was purified by silica gel column chromatography (chloroform/methanol/28% aqueous ammonia). Ethyl acetate and 4 M hydrogen chloride/ethyl acetate solution were added to the purified substance, followed by concentration under reduced pressure, thereby obtaining N-(diaminomethylene)-8-(2,4-difluorophenyl)-4-ethyl-3,4-dihydroisoquinoline-2(1H)-carboxamide hydrochloride (65 mg).

Example 2

CDI (62 mg) and DIPEA (44 mg) were added to a mixture of 8-(2,4-difluorophenyl)-5-methyl-1,2,3,4-tetrahydroisoquinoline hydrochloride (75 mg) and DMF (3 mL), followed by stirring for 30 minutes at an oil temperature of 60° C. After the reaction liquid was cooled to room temperature, guanidine carbonate (115 mg) was added thereto, followed by stirring for 1 hours at an oil temperature of 100° C. After the reaction liquid was cooled room temperature, saturated aqueous sodium bicarbonate and ethyl acetate were added thereto to perform liquid separation. The organic layer was washed with water and saturated brine in this order and then dried, followed by concentration under reduced pressure, and the residue was purified by NH silica gel column chromatography (chloroform/methanol=10:0 to 9:1). Ethanol and fumaric acid were added to the purified substance, and the precipitate was collected by filtration, thereby obtaining N-(diaminomethylene)-8-(2,4-difluorophenyl)-5-methyl-3,4-dihydroisoquinoline-2(1H)-carboxamide fumarate (80 mg).

Example 3

A mixture of tert-butyl 5-chloro-8-(2,4-difluorophenyl)-4-methoxy-3,4-dihydroisoquinoline-2(1H)-carboxyalte (74 mg), ethyl acetate (1.0 mL), and 4 M hydrogen chloride/ethyl acetate solution (1.0 mL) was stirred for 12 hours at room temperature and then concentrated under reduced pressure. DMF (3.5 mL), TEA (0.05 mL), and CDI (44 mg) were added in this order to the residue, followed by stirring for 30 minutes at an oil temperature of 60° C. After the reaction liquid was cooled to room temperature, guanidine carbonate (81 mg) was added thereto, followed by stirring for 3 hours at an oil temperature of 100° C. After the reaction liquid was cooled to room temperature, water and ethyl acetate were added thereto to perform liquid separation. The organic layer was concentrated under reduced pressure, and the residue was purified by silica gel column chromatography (chloroform/methanol/28% aqueous ammonia). Ethanol and fumaric acid were added to the purified substance, and the precipitate was collected by filtration, thereby obtaining 5-chloro-N-(diaminomethylene)-8-(2,4-difluorophenyl)-4-methoxy-3,4-dihydroisoquinoline-2(1H)-carboxamide fumarate (58 mg).

Example 4

CDI (35 mg) and DIPEA (28 mg) were added to a mixture of 8-(5-chloro-3-fluoropyridin-2-yl)-5-fluoro-1,2,3,4-tetrahydroisoquinoline hydrochloride (46 mg) and DMF (2.5 mL), followed by stirring for 30 minutes at an oil temperature of 60° C. After the reaction liquid was cooled to room temperature, guanidine carbonate (65 mg) was added thereto, followed by stirring for 2 hours at an oil temperature of 100° C. After the reaction liquid was cooled to room temperature, saturated aqueous sodium bicarbonate and ethyl acetate were added thereto to perform liquid separation. The organic layer was washed with water and saturated brine in this order and then dried, followed by concentration under reduced pressure, and the residue was purified by NH silica gel column chromatography (chloroform/methanol=10:0 to 9:1), thereby obtaining 8-(5-chloro-3-fluoropyridin-2-yl)-N-(diaminomethylene)-5-fluoro-3,4-dihydroisoquinoline-2(1H)-carboxamide (36 mg).

Example 5

A mixture of guanidine hydrochloride (319 mg), sodium methoxide (180 mg), and methanol (10 mL) was stirred for 1 hour at room temperature and then concentrated under reduced pressure. A mixture of 8-(2,4,6-trifluorophenyl)-1,2,3,4-tetrahydroisoquinoline hydrochloride (200 mg), CDI (119 mg), and N-methylpyrrolidone (10 mL), which had been stirred under heating at an oil temperature of 60° C., was added to the obtained residue, followed by stirring for 30 minutes at an oil temperature of 100° C. After the reaction liquid was cooled to room temperature, ethyl acetate and water were added thereto to perform liquid separation. The organic layer was washed with saturated brine and then dried, followed by concentration under reduced pressure, and the residue was purified by NH silica gel column chromatography (chloroform/methanol=10:0 to 9:1). Ethanol and fumaric acid were added to the purified substance, and the precipitate was collected by filtration, thereby obtaining N-(diaminomethylene)-8-(2,4,6-trifluorophenyl)-3,4-dihydroisoquinoline-2(1H)-carboxamide fumarate (174 mg).

Example 6

A mixture of guanidine hydrochloride (274 mg), sodium methoxide (155 mg), and methanol (10 mL) was stirred for 1 hour at room temperature and then concentrated under reduced pressure. A mixture of 8-(2-chlorophenyl)-1,2,3,4-tetrahydroisoquinoline (140 mg), CDI (102 mg), and DMF (10 mL), which had been separately stirred for 1 hour at room temperature, was added to the obtained residue, followed by stirring for 5 hours at an oil temperature of 100° C. After the reaction liquid was cooled to room temperature, water and ethyl acetate were added thereto to perform liquid separation. The organic layer was concentrated under reduced pressure, and the residue was purified by silica gel column chromatography (chloroform/methanol=10/1). 4 M hydrogen chloride/ethyl acetate solution was added to the purified substance to form a salt, thereby obtaining 8-(2-chlorophenyl)-N-(diaminomethylene)-3,4-dihydroisoquinoline-2(1H)-carboxamide hydrochloride (71 mg).

Example compounds shown in the tables described later were prepared in the same manner as in the above Examples, by using each of the corresponding starting materials. In addition, the structural formulas, physicochemical data, and preparation methods of the Example compounds will be shown in the tables described later.

The following abbreviations are used in the following tables.

PEx: Preparation Example number, Ex: Example number, Str: structural formula, Dat: physicochemical data (ESI+: ESI-MS[M+H]$^+$ or ESI-MS[M]$^+$; FAB+: FAB-MS[M+H]$^+$ or FAB-MS[M]$^+$; EI+: EI[M]$^+$; APCI/ESI+: APCI/ESI-MS [M+H]$^+$ or APCI/ESI-MS[M]$^+$ (APCI/ESI means that APCI and ESI are measured simultaneously); (M+Na): observed value of a peak to which Na+ has been added; (M-Boc): observed value of a peak where a Boc group was eliminated; NMR: δ (ppm) of a peak by $^1$HNMR in CDCl$_3$ or DMSO-d$_6$), "–": not measured, Me: methyl, Et: ethyl, cPr: cyclopropyl, tBu: tert-butyl, Ph: phenyl, Tf: trifluoromethanesulfonyl, Ts: p-toluenesulfonyl, Boc: tert-butoxycarbonyl, Fum: fumaric acid, DMSO: dimethyl sulfoxide, Syn: preparation process (a number indicates that the compound has been prepared using the corresponding starting material, in the same manner as in the compound that has the number as the Preparation Example number or the Example number. For example, "P2" indicates that a compound has been prepared in the same manner as in the compound of Preparation Example 2, and "2" indicates that a compound has been prepared in the same manner as in the compound of Example 2.)

TABLE 1

| PEx | Str |
|---|---|
| 1 | 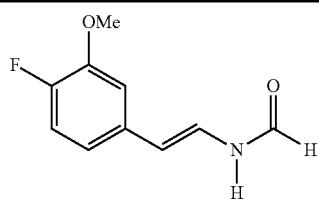 |
| 2 | 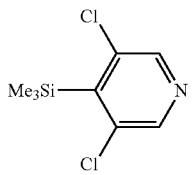 [SMILES: C[Si](C)(C)c1c(Cl)cncc1Cl] |
| 3 | 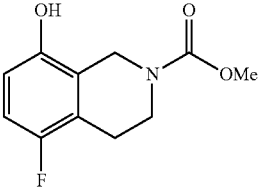 [SMILES: COC(=O)N1CCc2c(F)ccc(O)c2C1] |
| 4 | 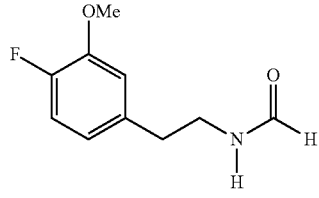 [SMILES: COc1cc(CCNC=O)ccc1F] |
| 5 | 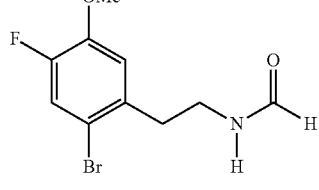 |
| 6 | 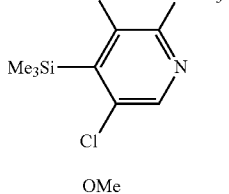 |
| 7 | 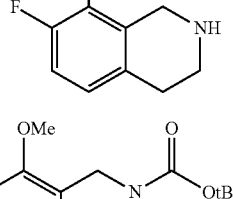 |
| 8 | 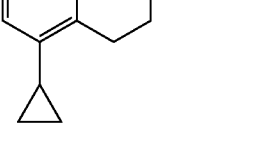 |

TABLE 1-continued
| PEx | Str |
|---|---|
| 9 | 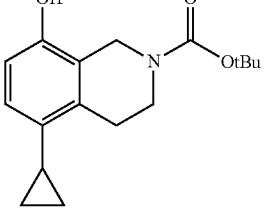 |
| 10 | 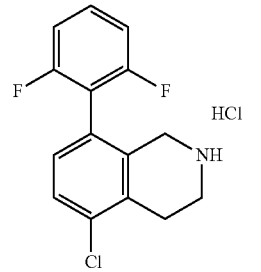 [SMILES: Fc1cccc(F)c1-c1ccc(Cl)c2c1CNCC2 ; Cl] |
| 11 | 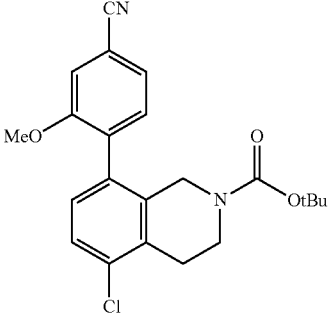 [SMILES: COc1cc(C#N)ccc1-c1ccc(Cl)c2c1CN(C(=O)OC(C)(C)C)CC2] |
| 12 | 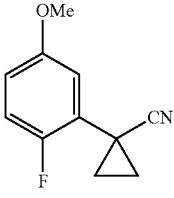 |
TABLE 2
| PEx | Str |
|---|---|
| 13 | 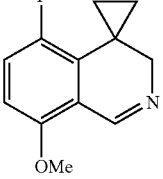 |
| 14 | 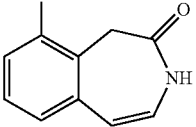 |
TABLE 2-continued
| PEx | Str |
|---|---|
| 15 | 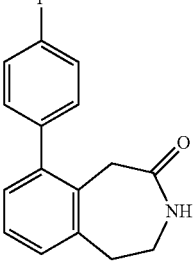 |
| 16 | 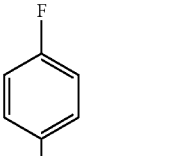 |
| 17 | 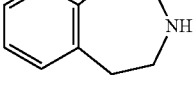 |
| 18 | 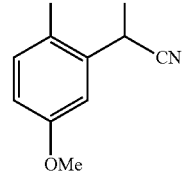 |
| 19 | 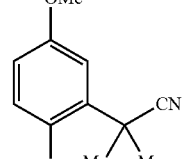 |
| 20 | 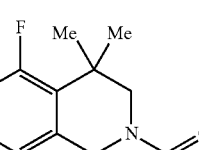 |
| 21 | 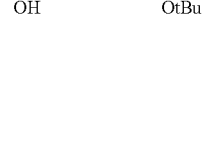 |

TABLE 2-continued
| PEx | Str |
|---|---|
| 22 | 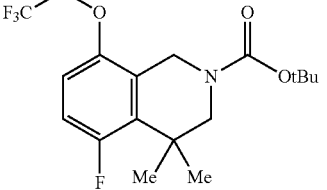 |
| 23 | 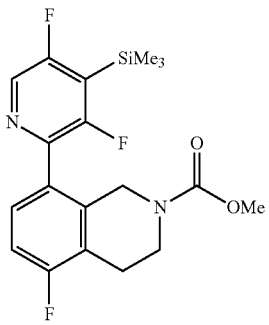 [SMILES: COC(=O)N1CCc2c(F)ccc(-c3ncc(F)c([Si](C)(C)C)c3F)c2C1] |
| 24 | 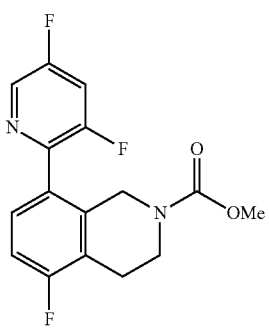 [SMILES: COC(=O)N1CCc2c(F)ccc(-c3ncc(F)cc3F)c2C1] |
TABLE 3
| PEx | Str |
|---|---|
| 25 | 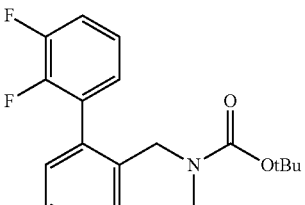 |
| 26 | 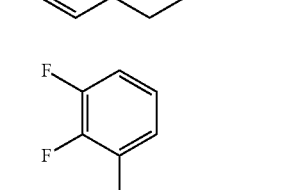 |
TABLE 3-continued
| PEx | Str |
|---|---|
| 27 | 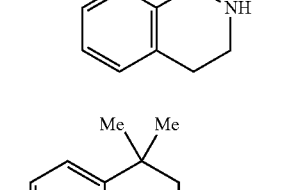 |
| 28 | 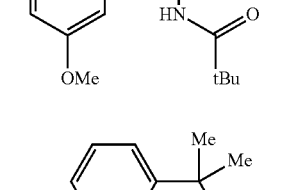 |
| 29 | 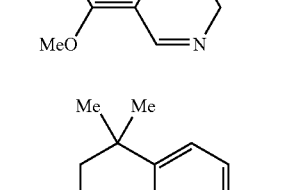 |
| 30 | 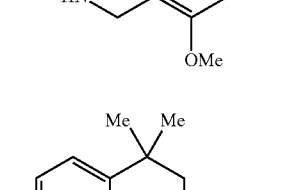 |
| 31 | 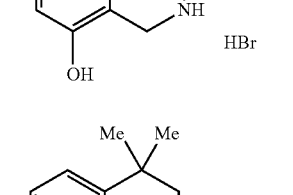 |
| 32 | 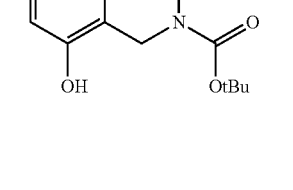 |
| 33 | 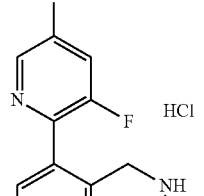 |

TABLE 3-continued

| PEx | Str |
|---|---|
| 34 | 8-OTf-4,4-dimethyl-N-Boc-1,2,3,4-tetrahydroisoquinoline |
| 35 | 8-OMe-5-F-1,2,3,4-tetrahydroisoquinoline (NH) |
| 36 | 8-(2-F-6-Cl-phenyl)-N-Boc-1,2,3,4-tetrahydroisoquinoline |

TABLE 4

| PEx | Str |
|---|---|
| 37 | 8-(4-CN-2-MeO-phenyl)-N-Boc-1,2,3,4-tetrahydroisoquinoline |
| 38 | 8-(3,4,5-triF-phenyl)-1,2,3,4-tetrahydroisoquinoline · HCl |
| 39 | 8-(2,4-diF-phenyl)-isoquinoline |

TABLE 4-continued

| PEx | Str |
|---|---|
| 40 | 8-(2,4-diF-phenyl)-4-F-N-Boc-1,2,3,4-tetrahydroisoquinoline |
| 41 | N-Ts-N-[(2'-(2,4-diF-phenyl)phenyl)methyl]glycine |
| 42 | 8-(2,4-diF-phenyl)-4-OMe-N-Boc-1,2,3,4-tetrahydroisoquinoline |
| 43 | 4-(4-F-phenyl)-N-Boc-isoindoline |
| 44 | 8-(2,4-diF-phenyl)-5-F-4-OH-1,2,3,4-tetrahydroisoquinoline (NH) |

TABLE 4-continued
| PEx | Str |
|---|---|
| 45 | 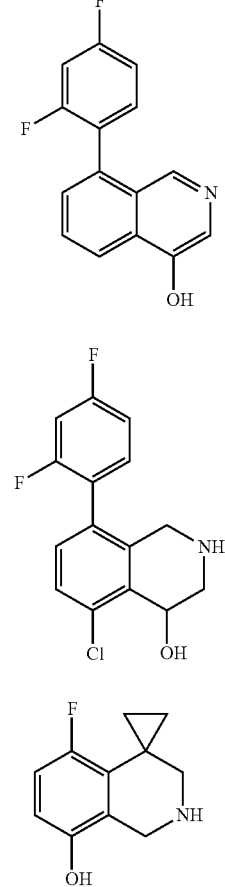 |
| 46 | |
TABLE 5
| PEx | Str |
|---|---|
| 47 | |
| 48 | |
| 49 | |
| 50 | |
| 51 | |
| 52 | |
| 53 | |
| 54 | |

TABLE 5-continued

| PEx | Str |
|---|---|
| 55 | 5-fluoro-4,4-dimethyl-1,2,3,4-tetrahydroisoquinolin-8-ol |
| 56 | 5'-fluoro-8'-hydroxy-spiro[cyclobutane-1,4'(1'H)-isoquinoline], 2',3'-dihydro |

TABLE 6

| PEx | Str |
|---|---|
| 57 | 2-(2-fluoro-5-methoxyphenyl)propan-1-amine |
| 58 | 2-(2-fluoro-5-methoxyphenyl)-2-methylpropan-1-amine |
| 59 | [1-(2-fluoro-5-methoxyphenyl)cyclobutyl]methanamine |
| 61 | 5-bromo-7-fluoro-8-methoxy-3,4-dihydroisoquinoline |
| 62 | 5-fluoro-8-methoxy-4-methyl-3,4-dihydroisoquinoline |

TABLE 6-continued

| PEx | Str |
|---|---|
| 63 | 5-fluoro-8-methoxy-4,4-dimethyl-3,4-dihydroisoquinoline |
| 64 | 5'-fluoro-8'-methoxy-spiro[cyclobutane-1,4'(3'H)-isoquinoline] |
| 65 | tert-butyl 5-fluoro-8-hydroxy-3,4-dihydroisoquinoline-2(1H)-carboxylate |
| 66 | tert-butyl 5-chloro-8-hydroxy-3,4-dihydroisoquinoline-2(1H)-carboxylate |
| 67 | tert-butyl 8-hydroxy-5-methyl-3,4-dihydroisoquinoline-2(1H)-carboxylate |
| 68 | tert-butyl 5-fluoro-8-hydroxy-4-methyl-3,4-dihydroisoquinoline-2(1H)-carboxylate |

TABLE 7

| PEx | Str |
|---|---|
| 69 | 5-chloro-1,2,3,4-tetrahydroisoquinolin-8-yl trifluoromethanesulfonate hydrochloride |

TABLE 7-continued

| PEx | Str |
|---|---|
| 70 | 8-OH, 5-F spiro-cyclopropyl tetrahydroisoquinoline N-Boc |
| 71 | 8-(2,4-difluorophenyl)-4-OH tetrahydroisoquinoline N-Boc |
| 72 | 8-(2,4-difluorophenyl)-5-F-4-OH tetrahydroisoquinoline N-Boc |
| 73 | 8-(2,4-difluorophenyl)-5-Cl-4-OH tetrahydroisoquinoline N-Boc |
| 74 | 8-OMe, 5-Br tetrahydroisoquinoline N-Boc |
| 75 | 8-OH, 5-F spiro-cyclobutyl tetrahydroisoquinoline N-Boc |
| 76 | 8-OH, 5-Me tetrahydroisoquinoline N-CO$_2$Me |
| 77 | 8-OTf, 5-Cl tetrahydroisoquinoline N-CO$_2$Me |
| 78 | 8-OH, 7-F tetrahydroisoquinoline N-CO$_2$Me |
| 79 | 8-OTf tetrahydroisoquinoline N-CO$_2$Me |
| 80 | 5-F, 8-OH tetrahydroisoquinoline·HBr |

TABLE 8

| PEx | Str |
|---|---|
| 81 | 8-OH, 5-Cl tetrahydroisoquinoline·HBr |
| 82 | 8-OH, 5-Me tetrahydroisoquinoline·HBr |

TABLE 8-continued

| PEx | Str |
|---|---|
| 83 | 7-fluoro-1,2,3,4-tetrahydroisoquinolin-8-ol · HBr |
| 84 | 5-fluoro-4-methyl-1,2,3,4-tetrahydroisoquinolin-8-ol · HBr |
| 85 | 8-(2,4-difluorophenyl)-1,2,3,4-tetrahydroisoquinolin-4-ol |
| 86 | 5-fluoro-8-methoxy-spiro[cyclopropane-1,4'-tetrahydroisoquinoline] |
| 87 | 8-(2,6-difluorophenyl)-1,2,3,4-tetrahydroisoquinoline |
| 88 | 5-fluoro-8-methoxy-4,4-dimethyl-1,2,3,4-tetrahydroisoquinoline |
| 89 | 5-fluoro-8-methoxy-spiro[cyclobutane-1,4'-tetrahydroisoquinoline] |

TABLE 8-continued

| PEx | Str |
|---|---|
| 90 | 5-fluoro-8-methoxy-4-methyl-1,2,3,4-tetrahydroisoquinoline |
| 91 | N-Boc 5-fluoro-8-OTf-spiro[cyclopropane-1,4'-tetrahydroisoquinoline] |
| 92 | 1-(2-fluoro-5-methoxyphenyl)cyclobutane-1-carbonitrile |
| 93 | 9-(4-fluorophenyl)-1,3,4,5-tetrahydro-2H-benzo[c]azepin-2-one |
| 94 | 5-chloro-8-methoxy-1,2,3,4-tetrahydroisoquinoline |

TABLE 9

| PEx | Str |
|---|---|
| 95 | 5-bromo-8-methoxy-1,2,3,4-tetrahydroisoquinoline |

TABLE 9-continued

| PEx | Str |
|---|---|
| 96 | 2,4-difluorobiphenyl-2'-ylmethyl glycine ethyl ester (NHCH2CO2Et linker) |
| 97 | 4-(3,5-difluorophenyl)-2-Boc-isoindoline |
| 98 | methyl 8-(3,5-difluoropyridin-2-yl)-5-methyl-3,4-dihydroisoquinoline-2(1H)-carboxylate |
| 99 | methyl 8-(3,5-dichloropyridin-2-yl)-5-fluoro-3,4-dihydroisoquinoline-2(1H)-carboxylate |
| 100 | methyl 8-(3,5-difluoropyridin-2-yl)-5-chloro-3,4-dihydroisoquinoline-2(1H)-carboxylate |
| 101 | methyl 8-(5-chloro-3-fluoropyridin-2-yl)-5-fluoro-3,4-dihydroisoquinoline-2(1H)-carboxylate |
| 102 | 2-Boc-8-OTf-5-fluoro-1,2,3,4-tetrahydroisoquinoline |
| 103 | 2-Boc-8-OTf-5-chloro-1,2,3,4-tetrahydroisoquinoline |
| 104 | methyl 8-OTf-5-fluoro-3,4-dihydroisoquinoline-2(1H)-carboxylate |

TABLE 10

| PEx | Str |
|---|---|
| 105 | 2-Boc-8-OTf-5-methyl-1,2,3,4-tetrahydroisoquinoline |
| 106 | methyl 8-OTf-5-methyl-3,4-dihydroisoquinoline-2(1H)-carboxylate |

TABLE 10-continued

| PEx | Str |
|---|---|
| 107 | 7-fluoro-8-OTf-3,4-dihydroisoquinoline-2(1H)-carboxylic acid methyl ester |
| 108 | 8-OTf-5-fluoro-4-methyl-3,4-dihydroisoquinoline-2(1H)-carboxylic acid tert-butyl ester (Boc) |
| 109 | 8-OTf-5-cyclopropyl-3,4-dihydroisoquinoline-2(1H)-carboxylic acid tert-butyl ester (Boc) |
| 110 | 8-OTf-5-fluoro-4,4-dimethyl-3,4-dihydroisoquinoline-2(1H)-carboxylic acid tert-butyl ester (Boc) |
| 112 | 8-OTf-5-fluoro-spiro[cyclobutane-1,4'-isoquinoline]-2'(1'H)-carboxylic acid tert-butyl ester (Boc) |
| 113 | 2',4'-difluoro-5-chloro-biphenyl-2-carbaldehyde |
| 114 | 8-(2,2,2-trifluoroethoxy)-5-fluoro-spiro[cyclopropane-1,4'-isoquinoline]-2'(1'H)-carboxylic acid tert-butyl ester (Boc) |

TABLE 10-continued

| PEx | Str |
|---|---|
| 115 | 3-fluoro-4-trimethylsilyl-5-chloropyridine |

TABLE 11

| PEx | Str |
|---|---|
| 116 | N-[2-(5-methoxy-2-fluorophenyl)propyl]formamide |
| 117 | N-[2-(5-methoxy-2-fluorophenyl)-2-methylpropyl]formamide |
| 118 | N-{[1-(2-fluoro-5-methoxyphenyl)cyclobutyl]methyl}formamide |
| 120 | 8-(2,4-difluorophenyl)-5-fluoro-spiro[cyclopropane-1,4'-isoquinoline] HCl |
| 121 | 8-(2-fluorophenyl)-5-fluoro-spiro[cyclopropane-1,4'-isoquinoline] HCl |

TABLE 11-continued
| PEx | Str |
|---|---|
| 122 | 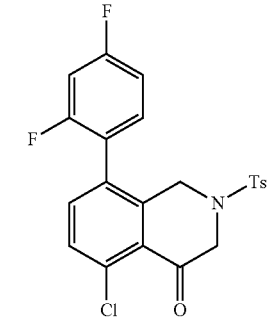 |
| 123 | |
| 124 | |
| 125 | |
| 126 | |
TABLE 12
| PEx | Str |
|---|---|
| 127 | 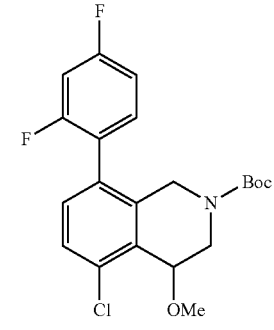 [SMILES: COC1CN(C(=O)OC(C)(C)C)Cc2c(-c3ccc(F)cc3F)cccc21] |
| 128 | |
| 129 | |
| 130 | |
| 131 | |

TABLE 12-continued
| PEx | Str |
|---|---|
| 132 | 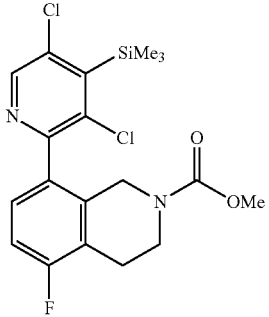 [SMILES: COC(=O)N1CCc2c(F)ccc(-c3ncc(Cl)c([Si](C)(C)C)c3Cl)c2C1] |
| 133 | 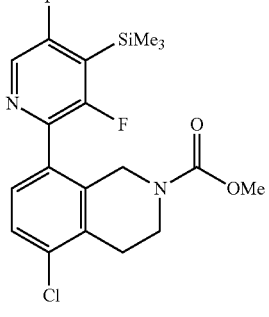 |
| 134 | 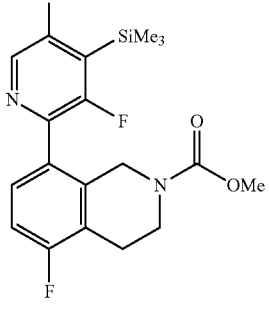 |
| 135 | 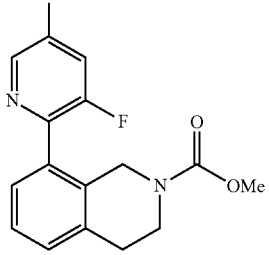 |
| 136 | 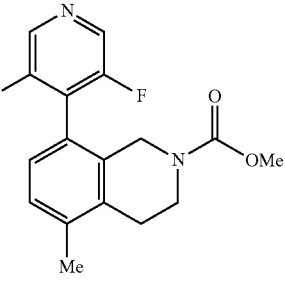 |
TABLE 13
| PEx | Str |
|---|---|
| 137 | 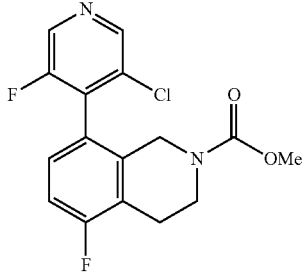 |
| 138 | 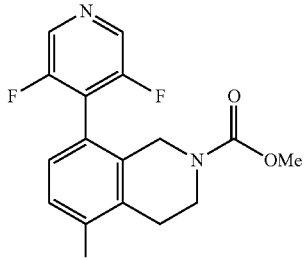 |
| 139 |  |
| 140 | 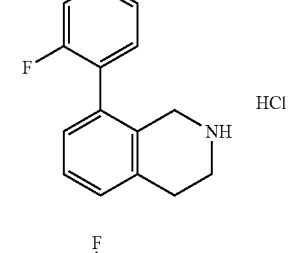 |
| 141 | 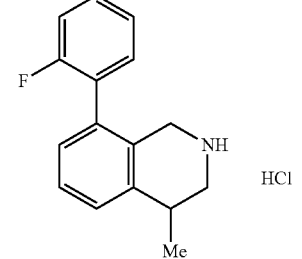 |

TABLE 13-continued
| PEx | Str |
|---|---|
| 142 | 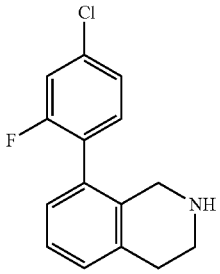 |
| 143 | 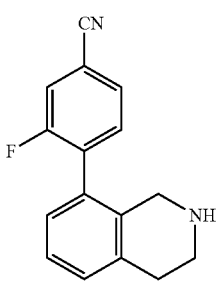 |
| 144 | 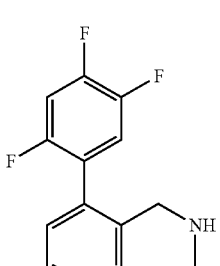 |
| 145 | 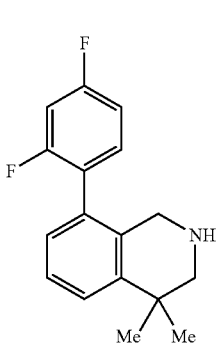 |
| 146 | 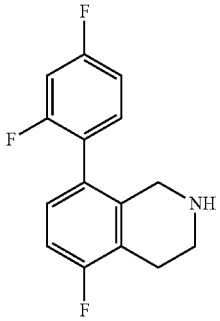 |
TABLE 14
| PEx | Str |
|---|---|
| 147 | 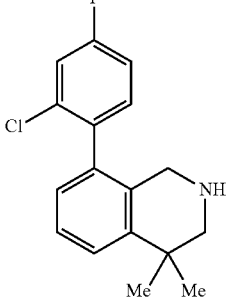 |
| 148 | 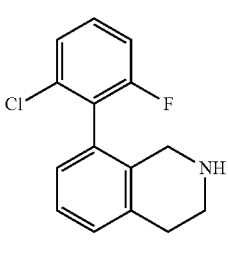 [SMILES: Fc1cccc(Cl)c1-c1cccc2c1CNCC2] |
| 149 | 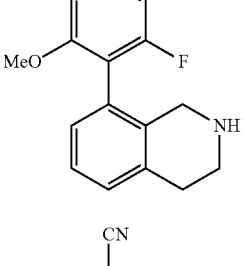 |
| 150 | 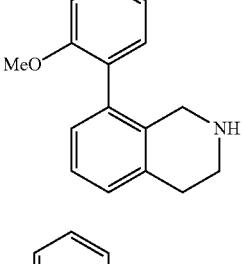 |
| 151 | 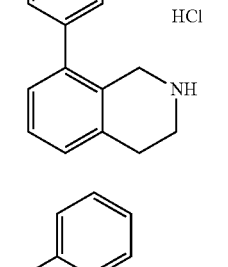 |
| 152 | 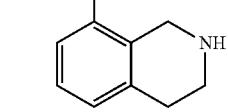 |

TABLE 14-continued

| PEx | Str |
|---|---|
| 153 | 8-(3-fluoropyridin-4-yl)-1,2,3,4-tetrahydroisoquinoline |
| 154 | 5-chloro-8-(2,4,6-trifluorophenyl)-1,2,3,4-tetrahydroisoquinoline HCl |
| 155 | 5-chloro-8-(2-chlorophenyl)-1,2,3,4-tetrahydroisoquinoline HCl |
| 156 | 8-(2,4-difluorophenyl)-4-fluoro-1,2,3,4-tetrahydroisoquinoline HCl |
| 157 | 5-chloro-8-(4-cyano-2-methoxyphenyl)-1,2,3,4-tetrahydroisoquinoline HCl |

TABLE 14-continued

| PEx | Str |
|---|---|
| 158 | 5-chloro-8-(2-fluoro-6-methoxyphenyl)-1,2,3,4-tetrahydroisoquinoline HCl |

TABLE 15

| PEx | Str |
|---|---|
| 159 | 8-(2,4-difluorophenyl)-4-methoxy-1,2,3,4-tetrahydroisoquinoline HCl |
| 160 | 5-chloro-8-(3-fluoropyridin-4-yl)-1,2,3,4-tetrahydroisoquinoline HCl |
| 161 | 5-chloro-8-(2,6-difluoro-4-methoxyphenyl)-1,2,3,4-tetrahydroisoquinoline HCl |

TABLE 15-continued
| PEx | Str |
|---|---|
| 162 | 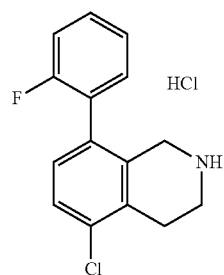 |
| 163 | 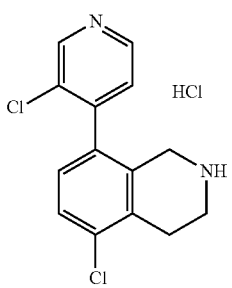 [SMILES: Clc1cnccc1-c1ccc(Cl)c2c1CNCC2 ; Cl] |
| 164 | 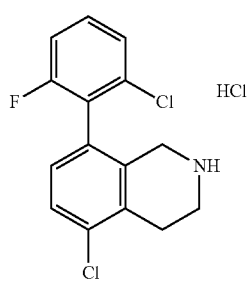 [SMILES: Fc1cccc(Cl)c1-c1ccc(Cl)c2c1CNCC2 ; Cl] |
| 165 | 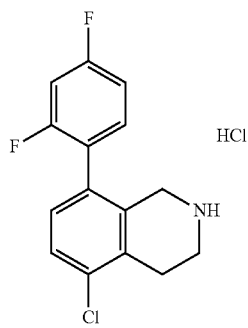 |
| 166 | 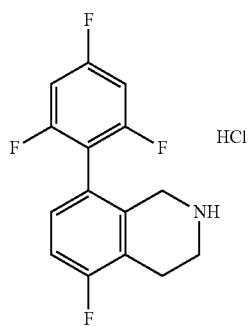 [SMILES: Fc1cc(F)c(-c2ccc(F)c3c2CNCC3)c(F)c1 ; Cl] |
TABLE 15-continued
| PEx | Str |
|---|---|
| 167 | 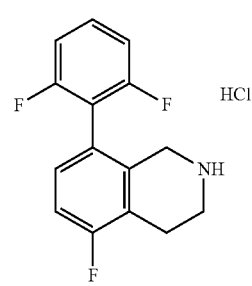 |
| 168 | 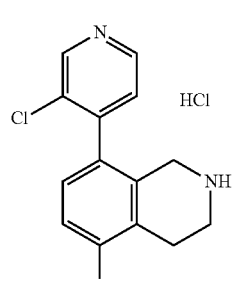 |
TABLE 16
| PEx | Str |
|---|---|
| 169 | 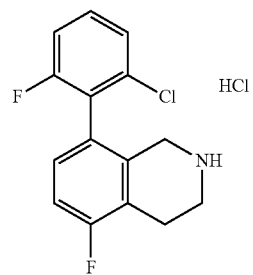 |
| 170 | 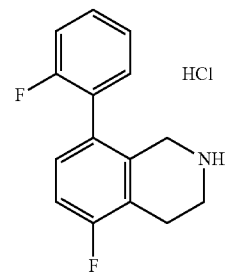 |
| 171 | 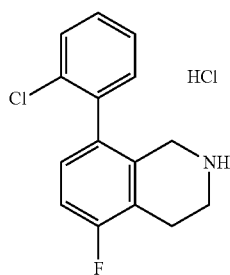 [SMILES: Fc1ccc(-c2ccccc2Cl)c2c1CCNC2 ; Cl] |

TABLE 16-continued
| PEx | Str |
|---|---|
| 172 | 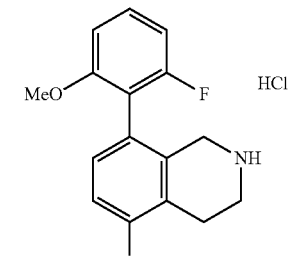 |
| 173 | 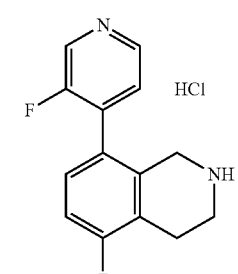 |
| 174 | 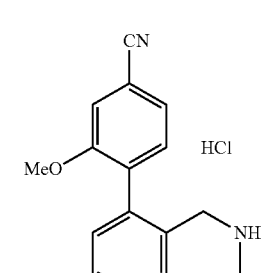 |
| 175 | 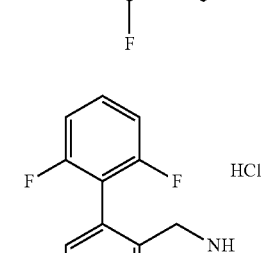 |
| 176 | 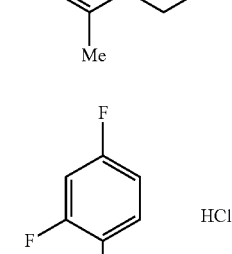 |
| 177 | 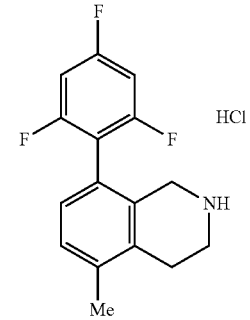 [SMILES: Cc1ccc(-c2c(F)cc(F)cc2F)c2c1CCNC2 ; Cl] |
| 178 | 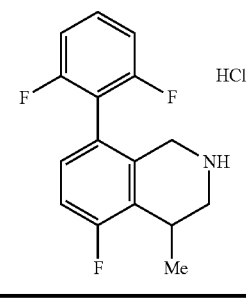 |
TABLE 17
| PEx | Str |
|---|---|
| 179 | 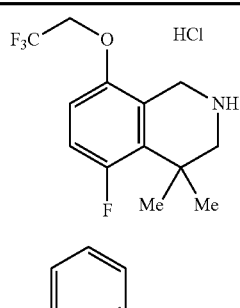 |
| 180 | 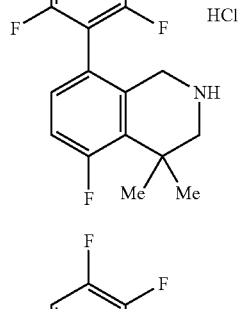 |
| 181 | 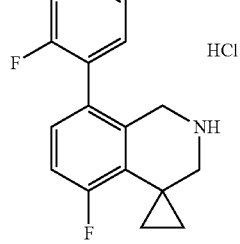 |

TABLE 17-continued
| PEx | Str |
|---|---|
| 182 | 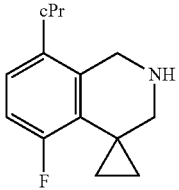 HCl |
| 183 | 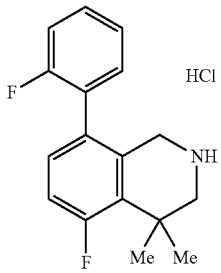 HCl |
| 184 | 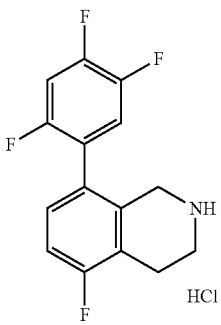 [SMILES: Fc1cc(F)c(-c2ccc(F)c3c2CNCC3)cc1F ; Cl] HCl |
| 185 | 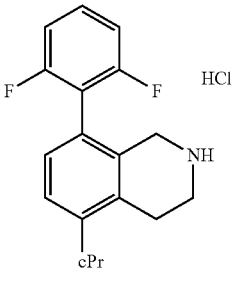 HCl |
| 186 | 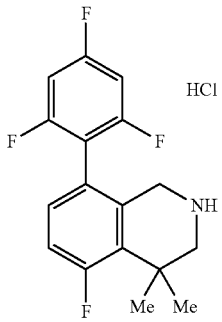 HCl |
TABLE 17-continued
| PEx | Str |
|---|---|
| 187 | 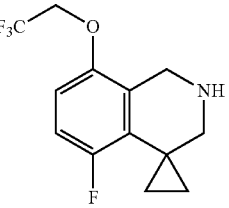 HCl |
| 188 |  HCl |
TABLE 18
| PEx | Str |
|---|---|
| 189 | 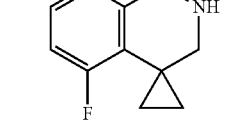 HCl |
| 190 |  HCl |
| 191 | 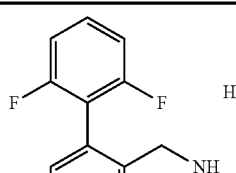 HCl |

TABLE 18-continued
| PEx | Str |
|---|---|
| 192 | 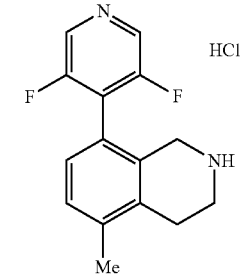 [SMILES: Cc1ccc(-c2c(F)cncc2F)c2c1CCNC2 ; Cl] |
| 193 | |
| 194 | |
| 195 | |
| 196 | |
TABLE 18-continued
| PEx | Str |
|---|---|
| 197 | 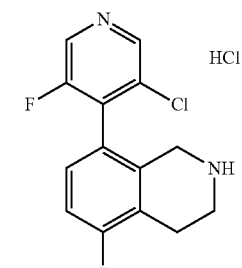 |
| 198 | |
TABLE 19
| PEx | Str |
|---|---|
| 199 | 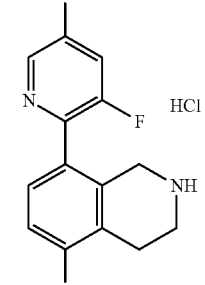 |
| 200 | 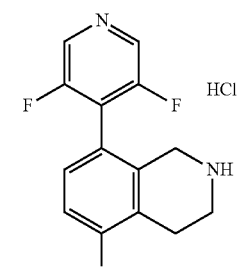 |

TABLE 19-continued
| PEx | Str |
|---|---|
| 201 | 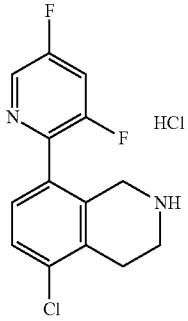 HCl |
| 202 | 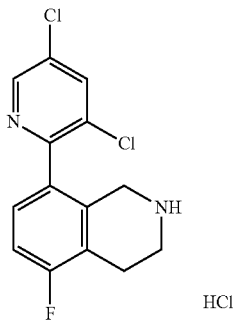 [SMILES: Fc1ccc(-c2ncc(Cl)cc2Cl)c2c1CCNC2 ; Cl] HCl |
| 203 | 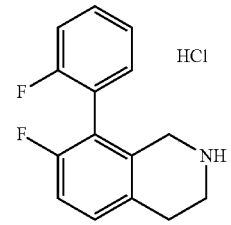 [SMILES: Fc1ccccc1-c1c(F)ccc2c1CNCC2 ; Cl] HCl |
| 204 | 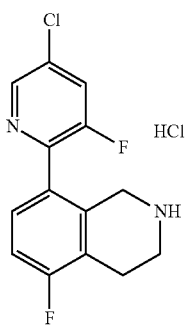 [SMILES: Fc1cc(Cl)cnc1-c1ccc(F)c2c1CNCC2 ; Cl] HCl |
| 205 | 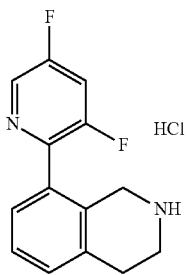 HCl |
| 206 | 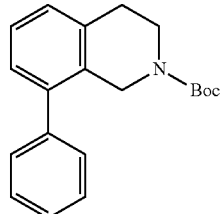 |
| 207 | 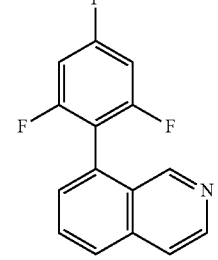 |
| 208 | 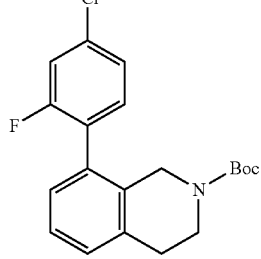 |
TABLE 20
| PEx | Str |
|---|---|
| 209 | 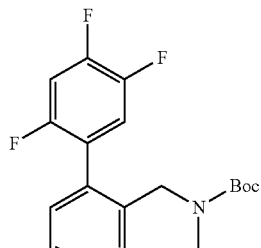 |
| 210 | 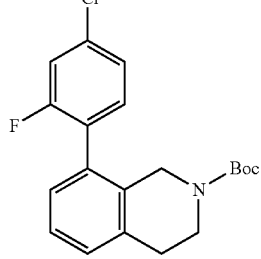 |

TABLE 20-continued
| PEx | Str |
|---|---|
| 211 | 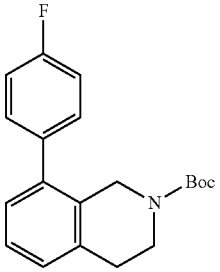 [SMILES: CC(C)(C)OC(=O)N1CCc2cccc(-c3ccc(F)cc3)c2C1] |
| 212 | 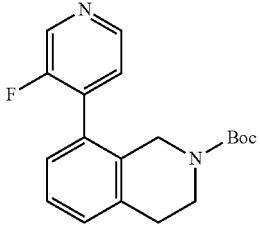 |
| 213 | 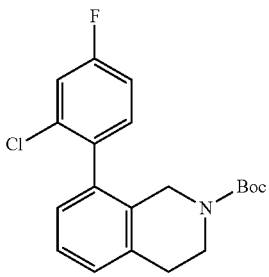 [SMILES: CC(C)(C)OC(=O)N1CCc2cccc(-c3ccc(F)cc3Cl)c2C1] |
| 214 | 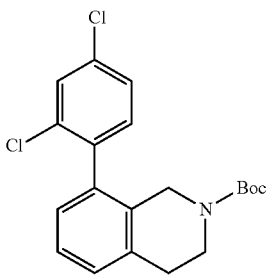 |
| 215 | 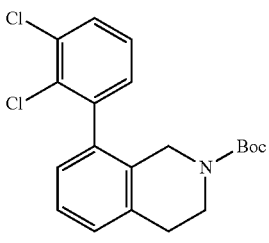 [SMILES: CC(C)(C)OC(=O)N1CCc2cccc(-c3cccc(Cl)c3Cl)c2C1] |
TABLE 20-continued
| PEx | Str |
|---|---|
| 216 | 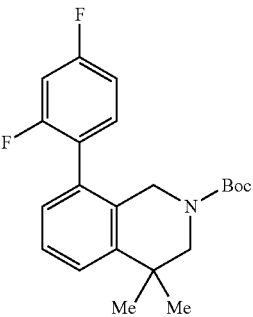 [SMILES: CC(C)(C)OC(=O)N1Cc2c(-c3ccc(F)cc3F)cccc2C(C)(C)C1] |
| 217 | 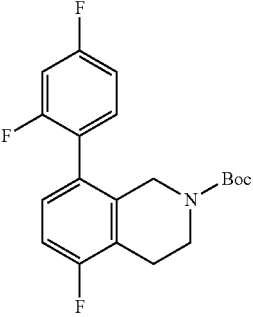 [SMILES: CC(C)(C)OC(=O)N1CCc2c(F)ccc(-c3ccc(F)cc3F)c2C1] |
| 218 | 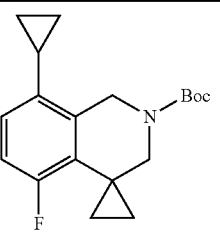 |
TABLE 21
| PEx | Str |
|---|---|
| 219 | 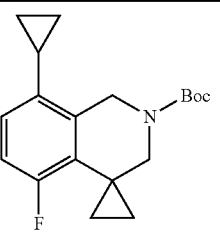 |

TABLE 21-continued
| PEx | Str |
|---|---|
| 220 | 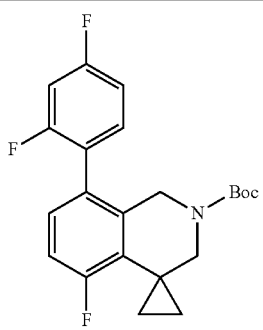 [SMILES: CC(C)(C)OC(=O)N1Cc2c(-c3ccc(F)cc3F)ccc(F)c2C2(CC2)C1] |
| 221 | 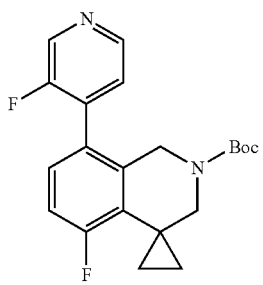 [SMILES: CC(C)(C)OC(=O)N1Cc2c(-c3ccncc3F)ccc(F)c2C2(CC2)C1] |
| 222 | 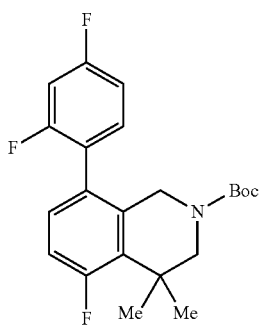 [SMILES: CC(C)(C)OC(=O)N1Cc2c(-c3ccc(F)cc3F)ccc(F)c2C(C)(C)C1] |
| 223 | 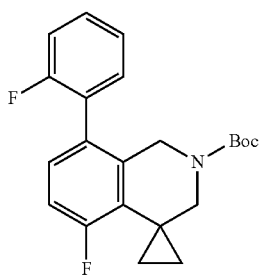 [SMILES: CC(C)(C)OC(=O)N1Cc2c(-c3ccccc3F)ccc(F)c2C2(CC2)C1] |
| 224 | 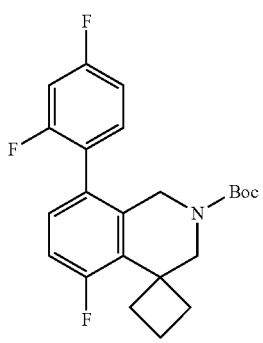 |
TABLE 21-continued
| PEx | Str |
|---|---|
| 225 | 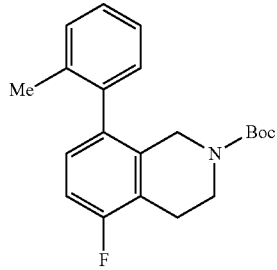 [SMILES: Cc1ccccc1-c1ccc(F)c2c1CN(C(=O)OC(C)(C)C)CC2] |
| 226 | 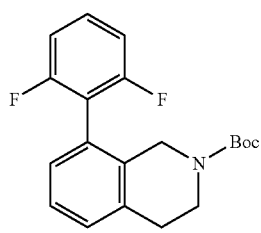 [SMILES: CC(C)(C)OC(=O)N1CCc2cccc(-c3c(F)cccc3F)c2C1] |
| 227 | 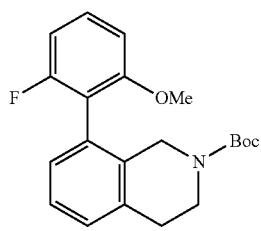 [SMILES: COc1cccc(F)c1-c1cccc2c1CN(C(=O)OC(C)(C)C)CC2] |
| 228 | 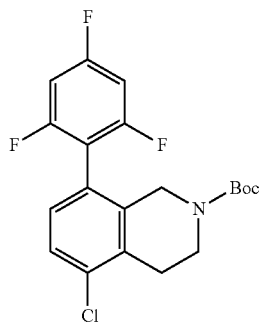 [SMILES: CC(C)(C)OC(=O)N1CCc2c(Cl)ccc(-c3c(F)cc(F)cc3F)c2C1] |
TABLE 22
| PEx | Str |
|---|---|
| 229 | 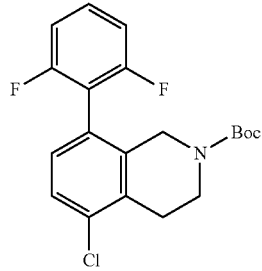 [SMILES: CC(C)(C)OC(=O)N1CCc2c(Cl)ccc(-c3c(F)cccc3F)c2C1] |

TABLE 22-continued
| PEx | Str |
|---|---|
| 230 | 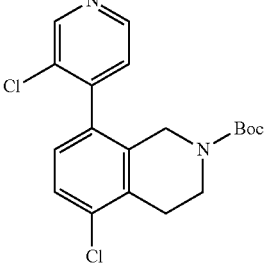 |
| 231 | 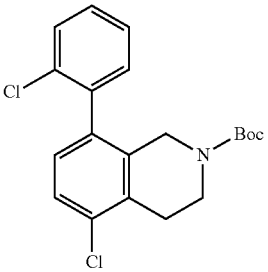 [SMILES: CC(C)(C)OC(=O)N1CCc2c(Cl)ccc(-c3ccccc3Cl)c2C1] |
| 232 | 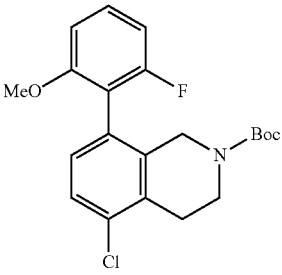 [SMILES: COc1cccc(F)c1-c1ccc(Cl)c2c1CN(C(=O)OC(C)(C)C)CC2] |
| 233 | 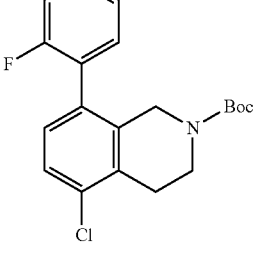 |
| 234 | 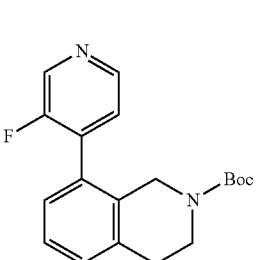 |
| 235 | 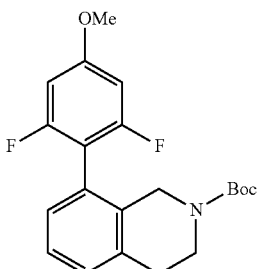 |
| 236 | 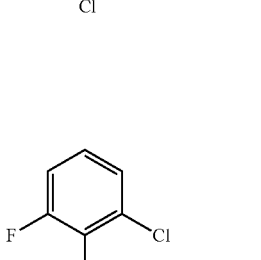 |
| 237 | 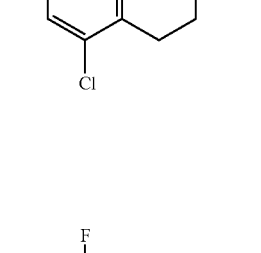 |
| 238 | 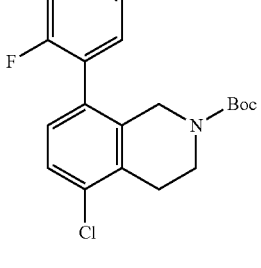 |

TABLE 23

| PEx | Str |
|---|---|
| 239 | 3-chloro-4-pyridyl, 5-fluoro, 8-position of N-Boc tetrahydroisoquinoline |
| 240 | 2-chloro-6-fluorophenyl, 5-fluoro, 8-position of N-Boc tetrahydroisoquinoline |
| 241 | 2-fluorophenyl, 5-fluoro, 8-position of N-Boc tetrahydroisoquinoline |
| 242 | 2-chlorophenyl, 5-fluoro, 8-position of N-Boc tetrahydroisoquinoline |
| 243 | 2-methoxy-6-fluorophenyl, 5-fluoro, 8-position of N-Boc tetrahydroisoquinoline |

TABLE 23-continued

| PEx | Str |
|---|---|
| 244 | 3-fluoro-4-pyridyl, 5-fluoro, 8-position of N-Boc tetrahydroisoquinoline |
| 245 | 2,6-difluorophenyl, 5-fluoro, 8-position of N-Boc tetrahydroisoquinoline |
| 246 | 2,6-difluorophenyl, 5-methyl, 8-position of N-Boc tetrahydroisoquinoline |
| 247 | 2,4,6-trifluorophenyl, 5-methyl, 8-position of N-Boc tetrahydroisoquinoline |
| 248 | 2,4-difluorophenyl, 5-methyl, 8-position of N-Boc tetrahydroisoquinoline |

TABLE 24

| PEx | Str |
|---|---|
| 249 | 8-(2-fluorophenyl)-7-fluoro-3,4-dihydroisoquinoline-2(1H)-carboxylic acid methyl ester |
| 250 | 8-(2,6-difluorophenyl)-5-fluoro-4-methyl-3,4-dihydroisoquinoline-2(1H)-carboxylic acid tert-butyl ester |
| 251 | 8-(2,6-difluorophenyl)-5-fluoro-4,4-dimethyl-3,4-dihydroisoquinoline-2(1H)-carboxylic acid tert-butyl ester |
| 252 | 8-(2,4,5-trifluorophenyl)-5-fluoro-spiro[cyclopropane-1,4'-isoquinoline]-2'(1'H)-carboxylic acid tert-butyl ester |
| 253 | 8-(2,4,5-trifluorophenyl)-5-fluoro-3,4-dihydroisoquinoline-2(1H)-carboxylic acid tert-butyl ester |

TABLE 24-continued

| PEx | Str |
|---|---|
| 254 | 8-(2,6-difluorophenyl)-5-fluoro-spiro[cyclopropane-1,4'-isoquinoline]-2'(1'H)-carboxylic acid tert-butyl ester |
| 255 | 8-(2,4,6-trifluorophenyl)-5-fluoro-4,4-dimethyl-3,4-dihydroisoquinoline-2(1H)-carboxylic acid tert-butyl ester |
| 256 | 8-(2,4,6-trifluorophenyl)-5-fluoro-spiro[cyclopropane-1,4'-isoquinoline]-2'(1'H)-carboxylic acid tert-butyl ester |
| 257 | 8-(2-fluorophenyl)-5-fluoro-4,4-dimethyl-3,4-dihydroisoquinoline-2(1H)-carboxylic acid tert-butyl ester |
| 258 | 8-(2,6-difluorophenyl)-5-fluoro-spiro[cyclobutane-1,4'-isoquinoline]-2'(1'H)-carboxylic acid tert-butyl ester |

TABLE 25

| PEx | Str |
|---|---|
| 259 | 8-(2,6-difluorophenyl)-5-cyclopropyl-3,4-dihydroisoquinoline-2(1H)-carboxylic acid tert-butyl ester |
| 260 | 8-(4-cyano-2-fluorophenyl)-3,4-dihydroisoquinoline-2(1H)-carboxylic acid tert-butyl ester |
| 261 | 8-(4-cyano-2-methoxyphenyl)-5-fluoro-3,4-dihydroisoquinoline-2(1H)-carboxylic acid tert-butyl ester |
| 262 | 8-(2,4-difluorophenyl)-5-fluoro-4-hydroxy-2-tosyl-1,2,3,4-tetrahydroisoquinoline |

TABLE 26

| PEx | Syn | Dat |
|---|---|---|
| 1 | P1 | APCI/ESI+: 196 |
| 2 | P2 | APCI/ESI+: 220, 222 |
| 3 | P3 | APCI/ESI+: 226 |
| 4 | P4 | APCI+: 198 |
| 5 | P5 | APCI/ESI+: 276, 278 |
| 6 | P6 | NMR-CDCl$_3$: 0.34 (9H, d, J = 1.2 Hz), 0.45 (9H, d, J = 2.1 Hz), 8.49 (1H, d, J = 2.1 Hz) |
| 7 | P7 | APCI/ESI+: 182 |
| 8 | P8 | NMR-CDCl$_3$: 0.52-0.57 (2H, m), 0.83-0.89 (2H, m), 1.50 (9H, s), 1.71-1.79 (1H, m), 2.93 (2H, t, J = 5.8 Hz), 3.67 (2H, t, J = 5.8 Hz), 3.80 (3H, s), 4.49 (2H, brs), 6.63 (1H, d, J = 8.4 Hz), 6.91 (1H, d, J = 8.4 Hz) |
| 9 | P9 | NMR-CDCl$_3$: 0.51-0.56 (2H, m), 0.82-0.88 (2H, m), 1.50 (9H, s), 1.69-1.77 (1H, m), 2.92 (2H, t, J = 5.3 Hz), 3.68 (2H, t, J = 5.3 Hz), 4.54 (2H, brs), 6.54 (1H, d, J = 8.2 Hz), 6.81 (1H, d, J = 8.2 Hz) |
| 10 | P10 | APCI/ESI+: 280 |
| 11 | P11 | ESI+: 399, 401 |
| 12 | P12 | NMR-CDCl$_3$: 1.38-1.41 (2H, m), 1.66-1.69 (2H, m), 3.78 (3H, s), 6.79-6.85 (2H, m), 7.00 (1H, t, J = 9 Hz) |
| 13 | P13 | ESI+: 196 |
| 14 | P14 | ESI+: 224 |
| 15 | P15 | ESI+: 206 |
| 16 | P16 | ESI+: 194 |
| 17 | P17 | ESI+: 256 |
| 18 | P18 | ESI+: 242 |
| 19 | P19 | EI: 179 |
| 20 | P20 | EI: 193 |
| 21 | P21 | ESI+: 296 |
| 22 | P22 | ESI+: 378 |
| 23 | P23 | ESI+: 395 |

TABLE 27

| PEx | Syn | Dat |
|---|---|---|
| 24 | P24 | ESI+: 323 |
| 25 | P25 | ESI+: 265 |
| 26 | P26 | ESI+: 323 |
| 27 | P27 | FAB+: 346 |
| 28 | P28 | ESI+: 246 |
| 29 | P29 | EI: 263 |
| 30 | P30 | ESI+: 190 |
| 31 | P31 | ESI+: 192 |
| 32 | P32 | ESI+: 178 |
| 33 | P33 | FAB−: 276 |
| 34 | P34 | FAB+: 410 |
| 35 | P35 | APCI/ESI+: 182 |
| 36 | P36 | ESI+: 362, 364 |
| 37 | P37 | ESI+: 387 (M + Na) |
| 38 | P38 | APCI/ESI+: 264 |
| 39 | P39 | ESI+: 242 |
| 40 | P40 | ESI+: 386 (M + Na) |
| 41 | P41 | ESI+: 432 |
| 42 | P42 | ESI+: 376 |
| 43 | P43 | ESI+: 336 (M + Na) |
| 44 | P44 | APCI/ESI+: 280 |
| 45 | P45 | ESI+: 400, 402 |
| 46 | P46 | APCI/ESI+: 398, 400 |
| 47 | P47 | ESI+: 444, 446 |
| 48 | P48 | ESI+: 268 |
| 49 | P49 | APCI/ESI+: 340 |
| 50 | P50 | ESI+: 256 |
| 51 | P51 | ESI+: 390 |
| 52 | P52 | ESI+: 258 |
| 53 | P44 | ESI+: 296 |

TABLE 28

| PEx | Syn | Dat |
|---|---|---|
| 54 | P9 | — |
| 55 | P9 | — |
| 56 | P9 | — |
| 57 | P13 | ESI+: 184 |
| 58 | P13 | ESI+: 198 |
| 59 | P13 | ESI+: 210 |
| 61 | P15 | APCI/ESI+: 258, 260 |
| 62 | P15 | ESI+: 194 |
| 63 | P15 | ESI+: 208 |

TABLE 28-continued

| PEx | Syn | Dat |
|---|---|---|
| 64 | P15 | ESI+: 220 |
| 65 | P33 | FAB+: 268 |
| 66 | P33 | ESI+: 284 |
| 67 | P33 | ESI+: 264 |
| 68 | P33 | ESI+: 304 (M + Na) |
| 69 | P10 | ESI+: 316, 318 |
| 70 | P33 | ESI+: 294 |
| 71 | P21 | ESI+: 362 |
| 72 | P21 | ESI+: 380 |
| 73 | P21 | ESI+: 396 |
| 74 | P21 | ESI+: 242, 244 (M − Boc) |
| 75 | P21 | ESI+: 308 |
| 76 | P3 | ESI+: 222 |
| 77 | P3 | NMR-CDCl$_3$: 2.88-2.92 (2H, m), 3.69-3.77 (5H, m), 4.68 (2H, brs), 7.15 (1H, d, J = 8.8 Hz), 7.35 (1H, d, J = 8.8 Hz) |
| 78 | P3 | APCI/ESI+: 226 |
| 79 | P3 | APCI/ESI+: 340 |
| 80 | P32 | APCI/ESI+: 168 |
| 81 | P32 | ESI+: 184 |
| 82 | P32 | ESI+: 164 |

TABLE 29

| PEx | Syn | Dat |
|---|---|---|
| 83 | P32 | APCI/ESI+: 168 |
| 84 | P32 | ESI+: 182 |
| 85 | P44 | APCI/ESI+: 262 |
| 86 | P31 | ESI+: 208 |
| 87 | P28 | ESI+: 246 |
| 88 | P31 | NMR-CDCl$_3$: 1.33 (3H, s), 1.34 (3H, s), 2.79 (2H, s), 3.77 (3H, s), 3.88 (2H, s), 6.57-6.60 (1H, m), 6.79-6.85 (1H, m) |
| 89 | P31 | — |
| 90 | P31 | ESI+: 196 |
| 91 | P34 | ESI+: 426 |
| 92 | P20 | EI: 205 |
| 93 | P43 | ESI+: 254 |
| 94 | P35 | NMR-CDCl$_3$: 2.72-2.75 (2H, m), 3.08-3.12 (2H, m), 3.81 (3H, s), 3.92 (2H, s), 6.62 (1H, d, J = 8.8 Hz), 7.17 (1H, d, J = 8.8 Hz) |
| 95 | P35 | APCI/ESI+: 244 |
| 96 | P49 | ESI+: 306 |
| 97 | P43 | ESI+: 388 (M + Na) |
| 98 | P24 | APCI/ESI+: 319 |
| 99 | P24 | APCI/ESI+: 355, 357 |
| 100 | P24 | ESI+: 339 |
| 101 | P24 | APCI/ESI+: 339 |
| 102 | P34 | FAB+: 400 |
| 103 | P34 | ESI+: 416, 418 |
| 104 | P34 | ESI+: 358 |
| 105 | P34 | ESI+: 396 |
| 106 | P34 | ESI+: 354 |
| 107 | P34 | APCI/ESI+: 358 |
| 108 | P34 | ESI+: 414 |
| 109 | P34 | APCI/ESI+: 322 (M − Boc) |
| 110 | P34 | ESI+: 428 |

TABLE 30

| PEx | Syn | Dat |
|---|---|---|
| 111 | P34 | ESI+: 426 |
| 112 | P34 | ESI+: 440 |
| 113 | P39 | EI: 252 |
| 114 | P22 | ESI+: 376 |
| 115 | P2 | APCI/ESI+: 204 |
| 116 | P14 | ESI+: 212 |
| 117 | P14 | ESI+: 226 |
| 118 | P14 | ESI+: 238 |
| 120 | P10 | ESI+: 290 |
| 121 | P10 | ESI+: 272 |

TABLE 30-continued

| PEx | Syn | Dat |
|---|---|---|
| 122 | P47 | ESI+: 460 |
| 123 | P47 | ESI+: 494 |
| 124 | P40 | FAB+: 382 |
| 125 | P40 | FAB+: 398 |
| 126 | P46 | APCI/ESI+: 414 |
| 127 | P46 | ESI+: 448 |
| 128 | P42 | ESI+: 410 |
| 129 | P41 | ESI+: 416, 418 |
| 130 | P41 | ESI+: 466 |
| 131 | P23 | APCI/ESI+: 391 |
| 132 | P23 | APCI/ESI+: 427, 429 |
| 133 | P23 | ESI+: 411 |
| 134 | P23 | APCI/ESI+: 411 |
| 135 | P23 | APCI/ESI+: 305 |
| 136 | P26 | ESI+: 319 |
| 137 | P26 | ESI+: 339, 341 |
| 138 | P26 | ESI+: 339 |
| 139 | P38 | ESI+: 246 |
| 140 | P38 | APCI/ESI+: 260 |
| 141 | P38 | ESI+: 274 |
| 142 | P28 | APCI/ESI+: 262 |

TABLE 31

| PEx | Syn | Dat |
|---|---|---|
| 143 | P28 | APCI/ESI+: 253 |
| 144 | P28 | ESI+: 264 |
| 145 | P28 | — |
| 146 | P28 | ESI+: 264 |
| 147 | P28 | — |
| 148 | P28 | ESI+: 262 |
| 149 | P28 | ESI+: 258 |
| 150 | P28 | ESI+: 265 |
| 151 | P10 | APCI/ESI+: 210 |
| 152 | P10 | APCI/ESI+: 244 |
| 153 | P10 | APCI/ESI+: 229 |
| 154 | P10 | ESI+: 298, 300 |
| 155 | P10 | APCI/ESI+: 278, 280 |
| 156 | P10 | ESI+: 264 |
| 157 | P10 | ESI+: 299, 301 |
| 158 | P10 | ESI+: 292, 294 |
| 159 | P10 | ESI+: 276 |
| 160 | P10 | ESI+: 263, 265 |
| 161 | P10 | ESI+: 310, 312 |
| 162 | P10 | APCI/ESI+: 262, 264 |
| 163 | P10 | ESI+: 279, 281 |
| 164 | P10 | APCI/ESI+: 296, 298 |
| 165 | P10 | APCI/ESI+: 280, 282 |
| 166 | P10 | ESI+: 282 |
| 167 | P10 | EI: 263 |
| 168 | P10 | FAB+: 263, 265 |
| 169 | P10 | ESI+: 280, 282 |
| 170 | P10 | ESI+: 246 |
| 171 | P10 | ESI+: 262, 264 |
| 172 | P10 | ESI+: 276 |
| 173 | P10 | ESI+: 247 |
| 174 | P10 | ESI+: 283 |
| 175 | P10 | ESI+: 260 |

TABLE 32

| PEx | Syn | Dat |
|---|---|---|
| 176 | P10 | ESI+: 260 |
| 177 | P10 | ESI+: 278 |
| 178 | P10 | ESI+: 278 |
| 179 | P10 | APCI/ESI+: 278 |
| 180 | P10 | ESI+: 292 |
| 181 | P10 | ESI+: 308 |
| 182 | P10 | ESI+: 218 |
| 183 | P10 | ESI+: 274 |
| 184 | P10 | ESI+: 282 |

TABLE 32-continued

| PEx | Syn | Dat |
| --- | --- | --- |
| 185 | P10 | — |
| 186 | P10 | |
| 187 | P10 | APCI/ESI+: 276 |
| 188 | P10 | ESI+: 308 |
| 189 | P10 | |
| 190 | P10 | ESI+: 273 |
| 191 | P10 | ESI+: 304 |
| 192 | P10 | ESI+: 282 |
| 193 | P10 | ESI+: 292 |
| 194 | P10 | ESI+: 304 |
| 195 | P10 | APCI/ESI+: 242 |
| 196 | P25 | ESI+: 265 |
| 197 | P25 | ESI+: 261 |
| 198 | P25 | ESI+: 281, 283 |
| 199 | P25 | APCI/ESI+: 261 |
| 200 | P25 | ESI+: 281, 283 |
| 201 | P25 | — |
| 202 | P25 | APCI/ESI+: 297, 299 |

TABLE 33

| PEx | Syn | Dat |
| --- | --- | --- |
| 203 | P25 | APCI/ESI+: 246 |
| 204 | P25 | APCI/ESI+: 281, 283 |
| 205 | P25 | ESI+: 247 |
| 206 | P27 | APCI/ESI+: 210 (M − Boc) |
| 207 | P27 | APCI/ESI+: 260 |
| 208 | P27 | FAB+: 344 |
| 209 | P27 | ESI+: 361 |
| 210 | P27 | FAB+: 364 |
| 211 | P27 | APCI/ESI+: 228 (M − Boc) |
| 212 | P27 | APCI/ESI+: 229 (M − Boc) |
| 213 | P27 | APCI/ESI+: 262 (M − Boc) |
| 214 | P27 | APCI/ESI+: 278, 280 (M − Boc) |
| 215 | P27 | APCI/ESI+: 278, 280, 282 (M − Boc) |
| 216 | P27 | FAB+: 374 |
| 217 | P27 | FAB+: 364 |
| 218 | P27 | ESI+: 390 |
| 219 | P27 | ESI+: 318 |
| 220 | P27 | ESI+: 390 |
| 221 | P27 | ESI+: 373 |
| 222 | P27 | ESI+: 392 |
| 223 | P27 | ESI+: 372 |
| 224 | P27 | ESI+: 404 |
| 225 | P27 | ESI+: 364 (M + Na) |
| 226 | P36 | ESI+: 346 |
| 227 | P36 | ESI+: 358 |
| 228 | P36 | FAB+: 398 |
| 229 | P36 | — |
| 230 | P36 | ESI+: 379, 381 |
| 231 | P36 | ESI+: 378, 380 |
| 232 | P36 | ESI+: 392, 394 |
| 233 | P36 | ESI+: 362 |
| 234 | P36 | ESI+: 363, 365 |
| 235 | P36 | ESI+: 410 |

TABLE 34

| PEx | Syn | Dat |
| --- | --- | --- |
| 236 | P36 | ESI+: 396, 398 |
| 237 | P36 | ESI+: 380, 382 |
| 238 | P36 | ESI+: 382 |
| 239 | P36 | ESI+: 363, 365 |
| 240 | P36 | FAB+: 380 |
| 241 | P36 | ESI+: 346 |
| 242 | P36 | ESI+: 362 |
| 243 | P36 | ESI+: 376 |
| 244 | P36 | ESI+: 347 |
| 245 | P36 | ESI+: 264 (M − Boc) |
| 246 | P36 | ESI+: 360 |
| 247 | P36 | ESI+: 378 |

TABLE 34-continued

| PEx | Syn | Dat |
| --- | --- | --- |
| 248 | P36 | ESI+: 360 |
| 249 | P36 | NMR-CDCl$_3$: 2.82-2.90 (2H, m), 3.65-3.75 (2H, m), 3.76 (3H, s), 4.64 (2H, brs), 7.13-7.25 (4H, m), 7.32-7.39 (2H, m) |
| 250 | P36 | ESI+: 378 |
| 251 | P36 | ESI+: 392 |
| 252 | P27 | ESI+: 408 |
| 253 | P27 | FAB+: 382 |
| 254 | P36 | ESI+: 390 |
| 255 | P36 | ESI+: 432 (M + Na) |
| 256 | P36 | ESI+: 408 |
| 257 | P36 | ESI+: 374 |
| 258 | P36 | ESI+: 404 |
| 259 | P36 | APCI/ESI+: 286 (M − Boc) |
| 260 | P37 | ESI+: 353 |
| 261 | P11 | ESI+: 383 |
| 262 | P39 | ESI+: 434 |

TABLE 35

| Ex | Str |
| --- | --- |
| 1 | 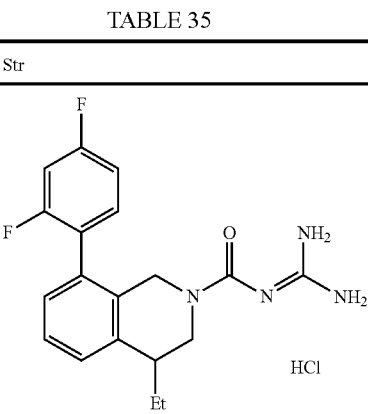 HCl |
| 2 | Fum |
| 3 | 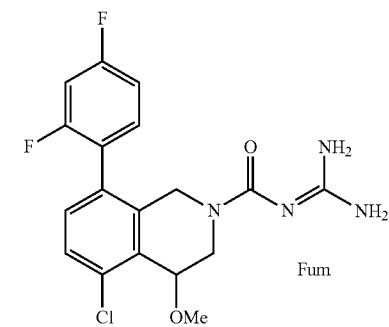 [SMILES: COC1CN(C(=O)N=C(N)N)Cc2c(-c3ccc(F)cc3F)ccc(Cl)c21 ; "Fum"] Fum |

TABLE 35-continued

| Ex | Str |
|----|-----|
| 4 | 5-chloro-3-fluoropyridin-2-yl / 5-fluoro tetrahydroisoquinoline guanidine urea |
| 5 | 2,4,6-trifluorophenyl tetrahydroisoquinoline guanidine urea, Fum |
| 6 | 2-chlorophenyl tetrahydroisoquinoline guanidine urea, HCl |
| 7 | 2,3-difluorophenyl tetrahydroisoquinoline guanidine urea, Fum |
| 8 | 2,4,5-trifluorophenyl tetrahydroisoquinoline guanidine urea, Fum |
| 9 | 3-fluoropyridin-4-yl tetrahydroisoquinoline guanidine urea, Fum |

TABLE 35-continued

| Ex | Str |
|----|-----|
| 10 | 2-chloro-4-fluorophenyl tetrahydroisoquinoline guanidine urea, Fum |

TABLE 36

| Ex | Str |
|----|-----|
| 11 | 2,3-dichlorophenyl tetrahydroisoquinoline guanidine urea, Fum |
| 12 | 2,4-dichlorophenyl tetrahydroisoquinoline guanidine urea, Fum |
| 13 | 8-phenyl tetrahydroisoquinoline guanidine urea, HCl |
| 14 | 2,4-difluorophenyl 4,4-dimethyl tetrahydroisoquinoline guanidine urea, Fum |

TABLE 36-continued

| Ex | Str |
|---|---|
| 15 | 8-(4-fluorophenyl)-3,4-dihydroisoquinoline-2(1H)-carboxyguanidine, Fum |
| 16 | 8-(2,4-difluorophenyl)-5-fluoro-3,4-dihydroisoquinoline-2(1H)-carboxyguanidine, Fum |
| 17 | 8-(2-chloro-4-fluorophenyl)-4,4-dimethyl-3,4-dihydroisoquinoline-2(1H)-carboxyguanidine, 0.5 Fum |
| 18 | 8-(2-chloro-6-fluorophenyl)-3,4-dihydroisoquinoline-2(1H)-carboxyguanidine, Fum |
| 19 | 8-(2,6-difluorophenyl)-3,4-dihydroisoquinoline-2(1H)-carboxyguanidine, Fum |

TABLE 36-continued

| Ex | Str |
|---|---|
| 20 | 8-(4-cyano-2-methoxyphenyl)-3,4-dihydroisoquinoline-2(1H)-carboxyguanidine, Fum |

TABLE 37

| Ex | Str |
|---|---|
| 21 | 8-(2-fluoro-6-methoxyphenyl)-3,4-dihydroisoquinoline-2(1H)-carboxyguanidine, Fum |
| 22 | 5-chloro-8-(2,6-difluorophenyl)-3,4-dihydroisoquinoline-2(1H)-carboxyguanidine, Fum |
| 23 | 5-chloro-8-(2,4,6-trifluorophenyl)-3,4-dihydroisoquinoline-2(1H)-carboxyguanidine, Fum |
| 24 | 5-chloro-8-(2-chlorophenyl)-3,4-dihydroisoquinoline-2(1H)-carboxyguanidine, Fum |

TABLE 37-continued

| Ex | Str |
|---|---|
| 25 | (3-chloropyridin-4-yl / 5-chloro tetrahydroisoquinoline carbonyl guanidine) Fum |
| 26 | (2,4,6-trifluorophenyl / 5-fluoro tetrahydroisoquinoline carbonyl guanidine) Fum |
| 27 | (2-fluorophenyl / 5-chloro tetrahydroisoquinoline carbonyl guanidine) Fum |
| 28 | (2,6-difluorophenyl / 5-fluoro tetrahydroisoquinoline carbonyl guanidine) Fum |
| 29 | (2-fluoro-6-methoxyphenyl / 5-chloro tetrahydroisoquinoline carbonyl guanidine) Fum |
| 30 | (4-cyano-2-methoxyphenyl / 5-chloro tetrahydroisoquinoline carbonyl guanidine) 0.5 Fum |

TABLE 38

| Ex | Str |
|---|---|
| 31 | (3-chloropyridin-4-yl / 5-fluoro tetrahydroisoquinoline carbonyl guanidine) Fum |
| 32 | (2-chloro-6-fluorophenyl / 5-fluoro tetrahydroisoquinoline carbonyl guanidine) Fum |
| 33 | (2-fluorophenyl / 5-fluoro tetrahydroisoquinoline carbonyl guanidine) Fum |
| 34 | (2-chlorophenyl / 5-fluoro tetrahydroisoquinoline carbonyl guanidine) Fum |

TABLE 38-continued
| Ex | Str |
|---|---|
| 35 | 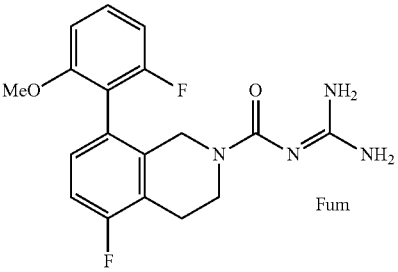 Fum |
| 36 | 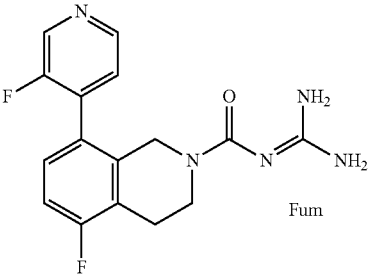 Fum |
| 37 | 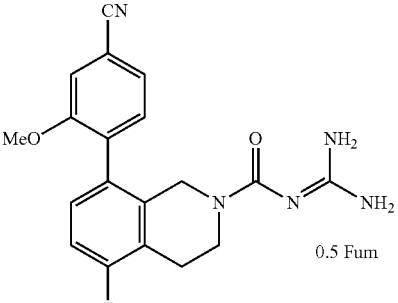 0.5 Fum |
| 38 | 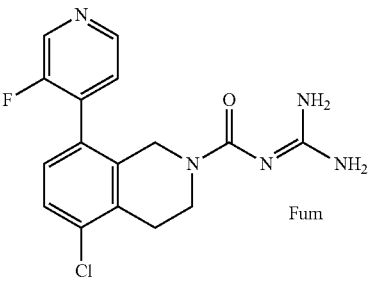 Fum |
| 39 | 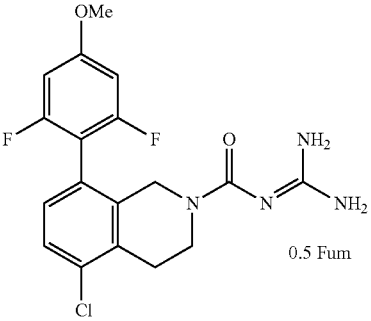 0.5 Fum |
TABLE 38-continued
| Ex | Str |
|---|---|
| 40 | 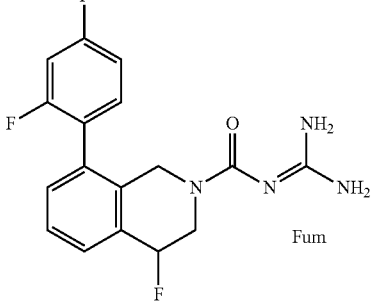 Fum |
TABLE 39
| Ex | Str |
|---|---|
| 41 | 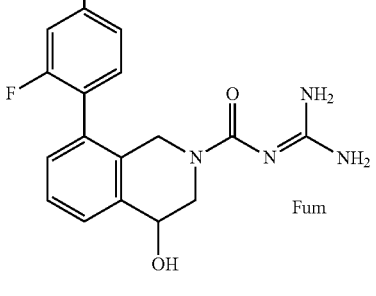 Fum |
| 42 | 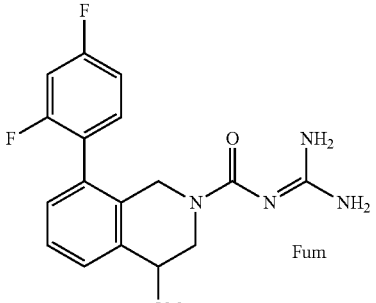 Fum |
| 43 | 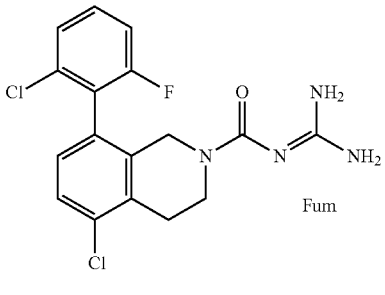 Fum |

TABLE 39-continued
| Ex | Str |
|---|---|
| 44 | 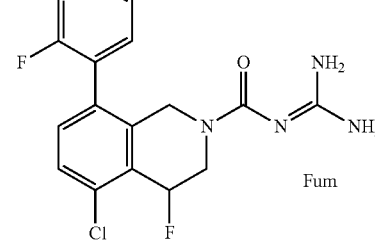 Fum |
| 45 | Fum |
| 46 | HCl |
| 47 | Fum |
| 48 | Fum |
TABLE 39-continued
| Ex | Str |
|---|---|
| 49 | 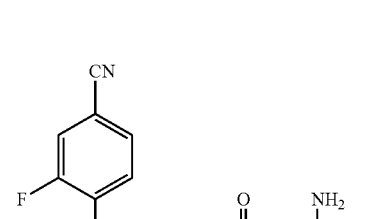 Fum |
| 50 | Fum |
TABLE 40
| Ex | Str |
|---|---|
| 51 | 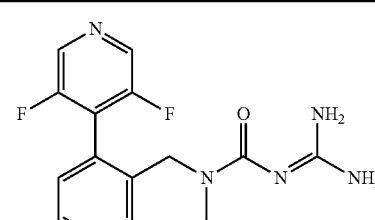 Fum |
| 52 | 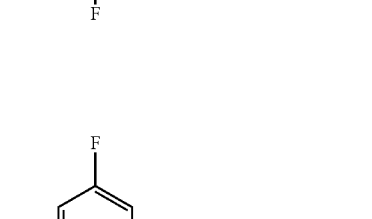 Fum |

TABLE 40-continued
| Ex | Str |
|---|---|
| 53 | 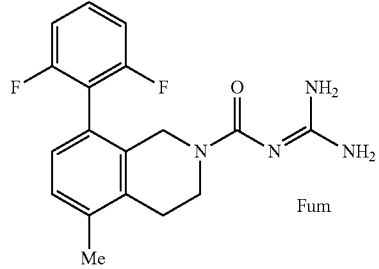 [SMILES: Cc1ccc(-c2c(F)cccc2F)c2c1CCN(C(=O)N=C(N)N)C2 ; "Fum"] Fum |
| 54 | 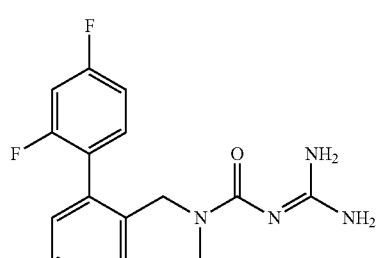 Fum |
| 55 | 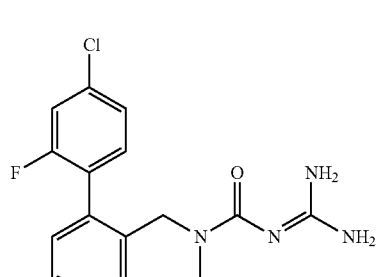 Fum |
| 56 | 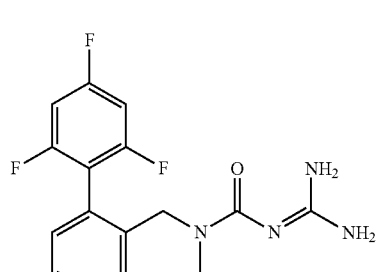 Fum |
| 57 | 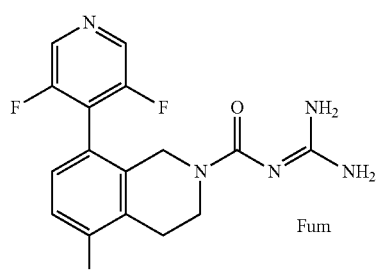 Fum |
| 58 | 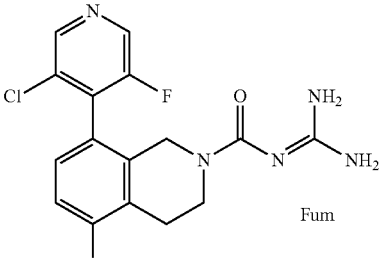 Fum |
| 59 | 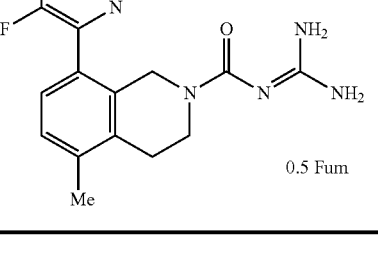 0.5 Fum |
| 60 | 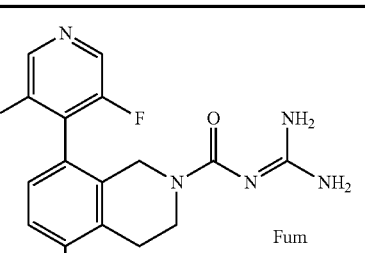 0.5 Fum |
TABLE 41
| Ex | Str |
|---|---|
| 61 | 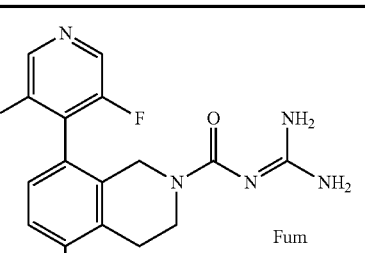 Fum |

TABLE 41-continued
| Ex | Str |
|---|---|
| 62 | 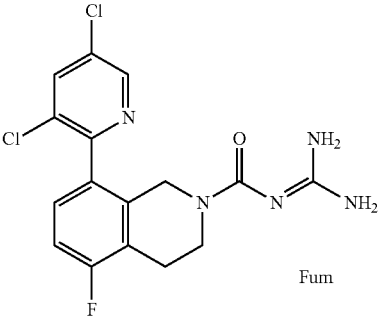 [SMILES: NC(N)=NC(=O)N1CCc2c(F)ccc(-c3ncc(Cl)cc3Cl)c2C1 ; "Fum"] Fum |
| 63 | 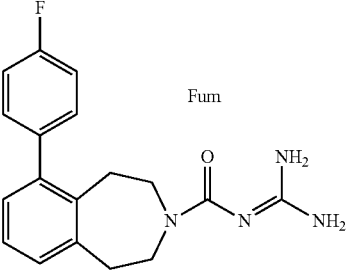 [SMILES: NC(N)=NC(=O)N1CCc2cccc(-c3ccc(F)cc3)c2CC1 ; "Fum"] Fum |
| 64 | 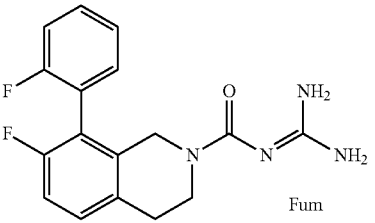 Fum |
| 65 | 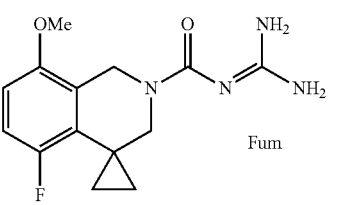 [SMILES: COc1ccc(F)c2c1CN(C(=O)N=C(N)N)CC21CC1 ; "Fum"] Fum |
| 66 | 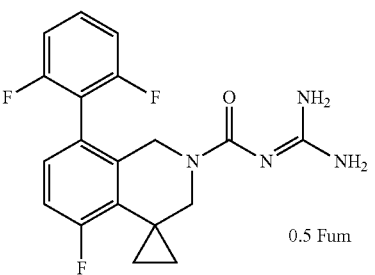 [SMILES: NC(N)=NC(=O)N1Cc2c(-c3c(F)cccc3F)ccc(F)c2C2(CC2)C1 ; "0.5 Fum"] 0.5 Fum |
| 67 | 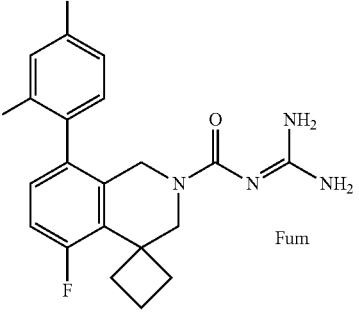 Fum |
| 68 | 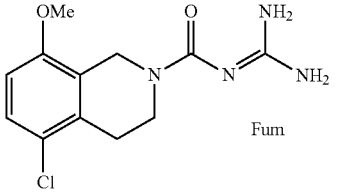 [SMILES: COc1ccc(Cl)c2c1CN(C(=O)N=C(N)N)CC2 ; "Fum"] Fum |
| 69 | 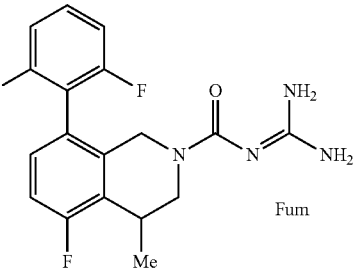 Fum |
| 70 | 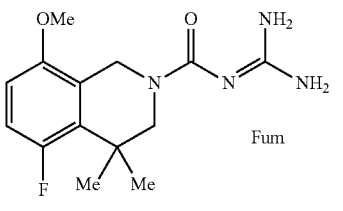 [SMILES: COc1ccc(F)c2c1CN(C(=O)N=C(N)N)CC2(C)C ; "Fum"] Fum |
TABLE 42
| Ex | Str |
|---|---|
| 71 | 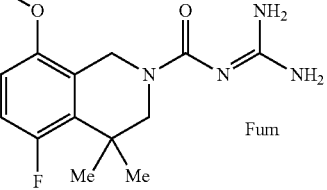 Fum |

TABLE 42-continued
| Ex | Str |
|----|-----|
| 72 | 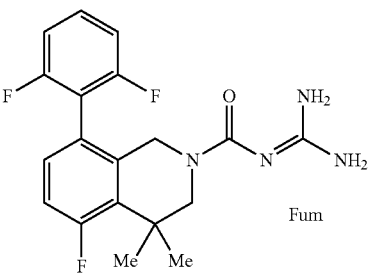 [SMILES: CC1(C)CN(C(=O)N=C(N)N)Cc2c(-c3c(F)cccc3F)ccc(F)c21 ; "Fum"] Fum |
| 73 | 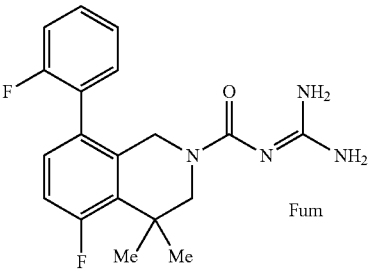 [SMILES: CC1(C)CN(C(=O)N=C(N)N)Cc2c(-c3ccccc3F)ccc(F)c21 ; "Fum"] Fum |
| 74 | 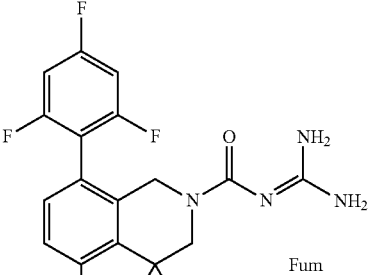 Fum |
| 75 | 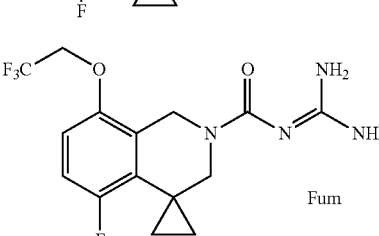 Fum |
| 76 | 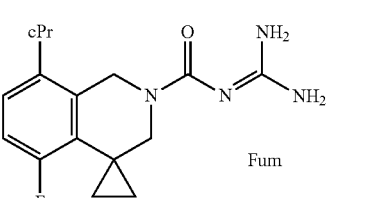 Fum |
| 77 | 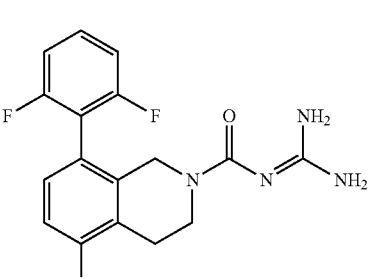 |
TABLE 42-continued
| Ex | Str |
|----|-----|
| 78 | 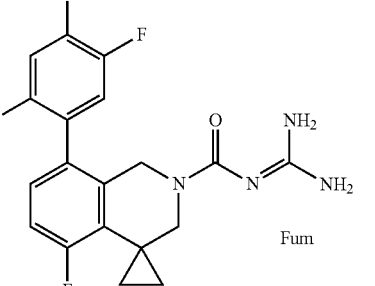 Fum |
| 79 | 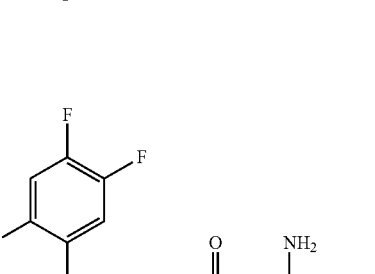 Fum |
| 80 | 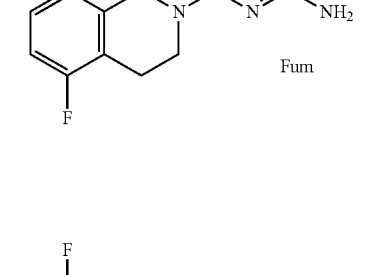 Fum |
TABLE 43
| Ex | Str |
|----|-----|
| 81 | 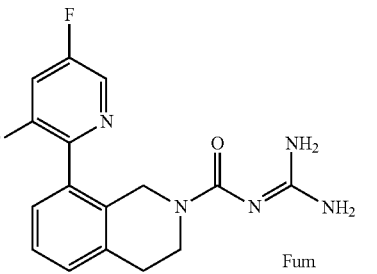 Fum |

TABLE 43-continued

| Ex | Str |
|---|---|
| 82 | 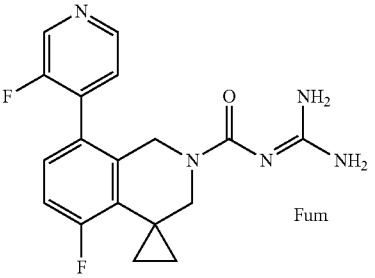 [SMILES: NC(N)=NC(=O)N1Cc2c(-c3ccncc3F)ccc(F)c2C2(CC2)C1 ; "Fum"] Fum |
| 83 | 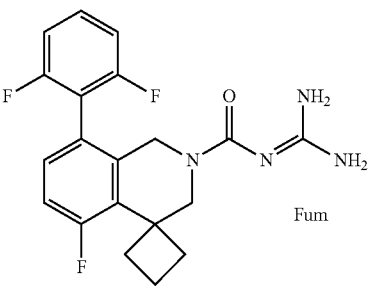 [SMILES: NC(N)=NC(=O)N1Cc2c(-c3c(F)cccc3F)ccc(F)c2C2(CCC2)C1 ; "Fum"] Fum |
| 84 | 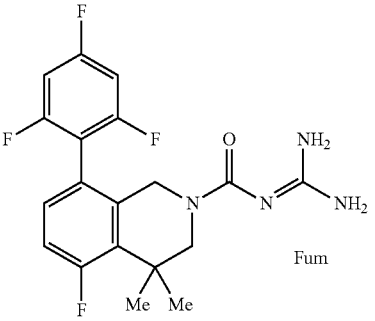 [SMILES: CC1(C)CN(C(=O)N=C(N)N)Cc2c(-c3c(F)cc(F)cc3F)ccc(F)c21 ; "Fum"] Fum |
| 85 | 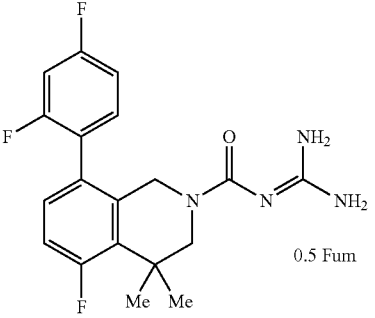 [SMILES: CC1(C)CN(C(=O)N=C(N)N)Cc2c(-c3ccc(F)cc3F)ccc(F)c21 ; "0.5 Fum"] 0.5 Fum |
| 86 | 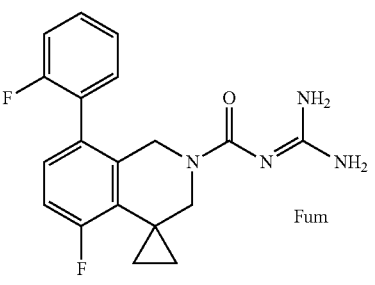 [SMILES: NC(N)=NC(=O)N1Cc2c(-c3ccccc3F)ccc(F)c2C2(CC2)C1 ; "Fum"] Fum |
| 87 | 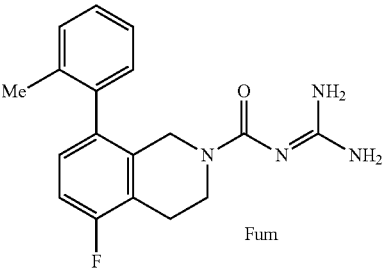 Fum |

TABLE 44

| Ex | Syn | Dat |
|---|---|---|
| 1 | 1 | ESI+: 359 |
| 2 | 2 | ESI+: 345 |
| 3 | 3 | ESI+: 395 |
| 4 | 4 | ESI+: 366, 368; NMR-DMSO-$d_6$: 2.79 (2H, brs), 3.79 (2H, brs), 4.49 (2H, brs), 7.19 (1H, t, J = 8.8 Hz), 7.27-7.31 (1H, m), 8.27 (1H, dd, J = 9.6, 2.0 Hz), 8.65 (1H, dd, J = 2.0, 0.9 Hz) |
| 5 | 5 | ESI+: 349 |
| 6 | 6 | ESI+: 329 |
| 7 | 2 | ESI+: 331 |
| 8 | 2 | ESI+: 349; NMR-DMSO-$d_6$: 2.87 (2H, t, J = 5.8 Hz), 3.73 (2H, brs), 4.36 (2H, brs), 6.56 (2H, s), 7.06-7.11 (1H, m), 7.25-7.30 (2H, m), 7.49-7.56 (1H, m), 7.62-7.72 (1H, m) |
| 9 | 2 | ESI+: 314 |
| 10 | 3 | ESI+: 347 |
| 11 | 3 | ESI+: 363 |
| 12 | 3 | ESI+: 363 |
| 13 | 1 | ESI+: 295 |
| 14 | 2 | ESI+: 359 |
| 15 | 3 | ESI+: 313 |
| 16 | 2 | ESI+: 349 |
| 17 | 2 | ESI+: 375, 377 |
| 18 | 2 | ESI+: 347, 349 |
| 19 | 2 | ESI+: 331 |
| 20 | 2 | ESI+: 350 |
| 21 | 2 | ESI+: 343 |
| 22 | 2 | ESI+: 365, 367 |
| 23 | 2 | ESI+: 383; NMR-DMSO-$d_6$: 2.79-2.82 (2H, m), 3.80 (2H, brs), 4.30 (2H, brs), 6.60 (2H, s), 7.17 (1H, d, J = 8 Hz), 7.37 (2H, t, J = 8 Hz), 7.45 (1H, d, J = 8 Hz) |

TABLE 45

| Ex | Syn | Dat |
|---|---|---|
| 24 | 2 | ESI+: 363 |
| 25 | 2 | ESI+: 364, 366 |
| 26 | 2 | ESI+: 367; NMR-DMSO-$d_6$: 2.76 (2H, t, J = 6 Hz), 3.80 (2H, brs), 4.30 (2H, brs), 6.60 (2H, s), 7.13-7.25 (2H, m), 7.36 (2H, t, J = 8 Hz) |
| 27 | 2 | ESI+: 347, 349 |
| 28 | 2 | ESI+: 349; NMR-DMSO-$d_6$: 2.76 (2H, t, J = 6 Hz), 3.81 (2H, brs), 4.29 (2H, brs), 6.60 (2H, s), 7.15-7.20 (2H, m), 7.25 (2H, t, J = 8 Hz), 7.52-7.62 (1H, m) |
| 29 | 2 | ESI+: 377, 379 |
| 30 | 2 | ESI+: 384, 386 |
| 31 | 2 | ESI+: 348, 350 |
| 32 | 2 | ESI+: 365, 367 |
| 33 | 2 | ESI+: 331 |

TABLE 45-continued

| Ex | Syn | Dat |
|---|---|---|
| 34 | 2 | ESI+: 347, 349 |
| 35 | 2 | ESI+: 361 |
| 36 | 2 | ESI+: 332 |
| 37 | 2 | ESI+: 368 |
| 38 | 2 | ESI+: 348, 350 |
| 39 | 2 | ESI+: 395, 397 |
| 40 | 2 | ESI+: 349 |
| 41 | 2 | ESI+: 347 |
| 42 | 2 | ESI+: 361 |
| 43 | 2 | ESI+: 381, 383 |
| 44 | 2 | ESI+: 365, 367;<br>NMR-DMSO-$d_6$: 2.78-2.81 (2H, m), 3.80 (2H, brs), 4.32 (2H, brs), 6.60 (2H, s), 7.09 (1H, d, J = 8 Hz), 7.19-7.24 (1H, m), 7.37-7.42 (3H, m) |
| 45 | 3 | ESI+: 299 |

TABLE 46

| Ex | Syn | Dat |
|---|---|---|
| 46 | 1 | ESI+: 350;<br>NMR-DMSO-$d_6$: 2.92-2.98 (2H, m), 3.82-3.89 (2H, m), 4.53 (2H, s), 7.25 (1H, t, J = 9 Hz), 7.35 (1H, t, J = 6 Hz), 8.10-8.16 (1H, m), 8.62-8.66 (1H, m) |
| 47 | 3 | ESI+: 317 |
| 48 | 3 | ESI+: 367 |
| 49 | 3 | ESI+: 383;<br>NMR-DMSO-$d_6$: 3.13-3.37 (1H, m), 3.86 (1H, brs), 4.80-5.10 (2H, m), 5.79-5.94 (1H, m), 6.61 (2H, s), 7.20-7.56 (5H, m) |
| 50 | 2 | ESI+: 338 |
| 51 | 2 | ESI+: 350 |
| 52 | 2 | ESI+: 345 |
| 53 | 2 | ESI+: 345 |
| 54 | 5 | ESI+: 331 |
| 55 | 2 | ESI+: 347 |
| 56 | 2 | ESI+: 363<br>NMR-DMSO-$d_6$: 2.26 (3H, s), 2.73 (2H, t, J = 6 Hz), 3.78 (2H, brs), 4.28 (2H, brs), 6.57 (2H, s), 7.00 (1H, d, J = 8 Hz), 7.16 (1H, d, J = 8 Hz), 7.31 (2H, t, J = 8 Hz) |
| 57 | 2 | ESI+: 346 |
| 58 | 2 | ESI+: 366, 368 |
| 59 | 2 | ESI+: 366;<br>NMR-DMSO-$d_6$: 2.80-2.83 (2H, m), 3.80 (2H, brs), 4.45 (2H, brs), 6.60 (1H, s), 7.24 (1H, d, J = 8 Hz), 7.46 (1H, d, J = 8 Hz), 8.10-8.15 (1H, m), 8.66 (1H, d, J = 2 Hz) |
| 60 | 2 | ESI+: 346<br>NMR-DMSO-$d_6$: 2.26 (3H, s), 2.70 (2H, t, J = 6.0 Hz), 3.78 (2H, brs), 4.41 (2H, brs), 6.58 (1H, s), 7.06 (1H, d, J = 7.4 Hz), 7.15 (1H, d, J = 7.4 Hz), 8.07 (1H, dt, J = 2.4, 9.2 Hz), 8.62 (1H, d, J = 2.4 Hz) |
| 61 | 2 | ESI+: 366, 368;<br>NMR-DMSO-$d_6$: 2.81 (2H, brs), 3.81 (2H, brs), 4.32 (2H, brs), 6.60 (2H, s), 7.27 (1H, d, J = 8 Hz), 7.51 (1H, d, J = 8 Hz), 8.71 (2H, brs) |

TABLE 47

| Ex | Syn | Dat |
|---|---|---|
| 62 | 2 | ESI+: 382, 384<br>NMR-DMSO-$d_6$: 2.77 (2H, t, J = 5.6 Hz), 3.78 (2H, brs), 4.33 (2H, brs), 6.59 (2H, s), 7.15-7.20 (2H, m), 8.40 (1H, brs), 8.71 (1H, d, J = 2 Hz) |
| 63 | 2 | ESI+: 327 |
| 64 | 2 | ESI+: 331 |
| 65 | 2 | ESI+: 293 |
| 66 | 2 | ESI+: 375;<br>NMR-DMSO-$d_6$: 0.91 (2H, brs), 1.40-1.43 (2H, m), 3.57 (2H, brs), 4.37 (2H, brs), 6.60 (1H, s), 7.04-7.12 (2H, m), 7.26 (2H, t, J = 8 Hz), 7.52-7.60 (1H, m) |
| 67 | 2 | ESI+: 389 |
| 68 | 2 | ESI+: 283 |
| 69 | 2 | ESI+: 363;<br>NMR-DMSO-$d_6$: 1.18 (3H, d, J = 7 Hz), 3.10-3.22 (2H, m), 3.80-3.85 (1H, m), 4.42 (1H, brs), 4.77 (1H, brs), 6.60 (2H, s), 7.15-7.17 (2H, m), 7.22-7.29 (2H, m), 7.52-7.60 (1H, m) |
| 70 | 2 | ESI+: 295 |
| 71 | 2 | ESI+: 363 |
| 72 | 2 | ESI+: 377 |
| 73 | 2 | ESI+: 359 |
| 74 | 2 | ESI+: 393;<br>NMR-DMSO-$d_6$: 0.91 (2H, s), 1.40-1.42 (2H, m), 3.57 (2H, brs), 4.37 (2H, brs), 6.57 (2H, s), 7.04-7.13 (2H, m), 7.34-7.38 (2H, m) |
| 75 | 2 | ESI+: 361 |
| 76 | 2 | ESI+: 303;<br>NMR-DMSO-$d_6$: 0.56-0.60 (2H, m), 0.85 (2H, brs), 0.89-0.94 (2H, m), 1.32-1.34 (2H, m), 1.76-1.83 (1H, m), 3.53 (2H, brs), 4.89 (2H, brs), 6.59 (2H, s), 6.79-6.88 (2H, m) |

TABLE 48

| Ex | Syn | Dat |
|---|---|---|
| 77 | 4 | ESI+: 371;<br>NMR-DMSO-$d_6$: 0.61-0.68 (2H, m), 0.90-0.97 (2H, m), 1.89-1.97 (1H, m), 2.92 (2H, t, J = 5.9 Hz), 3.82 (2H, brs), 4.27 (2H, brs), 6.94-7.03 (2H, m), 7.19-7.26 (2H, m), 7.48-7.57 (1H, m) |
| 78 | 2 | ESI+: 393;<br>NMR-DMSO-$d_6$: 0.92 (2H, brs), 1.39-1.41 (2H, m), 3.55 (2H, brs), 4.41-4.49 (2H, m), 6.59 (2H, s), 7.03-7.08 (2H, m), 7.52-7.58 (1H, m), 7.66-7.72 (1H, m) |
| 79 | 2 | ESI+: 367;<br>NMR-DMSO-$d_6$: 2.74-2.77 (2H, m), 3.79 (2H, brs), 4.36 (2H, brs), 6.55 (2H, s), 7.13-7.15 (2H, m), 7.50-7.57 (1H, m), 7.65-7.72 (1H, m) |
| 80 | 2 | ESI+: 375;<br>NMR-DMSO-$d_6$: 0.92 (2H, s), 1.40 (2H, s), 3.56 (2H, brs), 4.37-4.40 (2H, m), 6.60 (2H, s), 7.04-7.08 (2H, m), 7.18-7.23 (1H, m), 7.36-7.42 (2H, m) |
| 81 | 2 | ESI+: 332<br>NMR-DMSO-$d_6$: 2.85 (2H, t, J = 5.8 Hz), 3.75 (2H, brs), 4.41 (2H, brs), 6.59 (2H, s), 7.15-7.20 (1H, m), 7.26-7.30 (2H, m), 8.06-8.13 (1H, m), 8.64 (1H, d, J = 2.4 Hz) |
| 82 | 2 | ESI+: 358 |
| 83 | 2 | ESI+: 389 |
| 84 | 2 | ESI+: 395 |
| 85 | 2 | ESI+: 377 |
| 86 | 2 | ESI+: 357;<br>NMR-DMSO-$d_6$: 0.91 (2H, s), 1.40 (2H, s), 3.56 (2H, brs), 4.36-4.47 (2H, m), 6.61 (2H, s), 7.02-7.07 (2H, m), 7.29-7.35 (3H, m), 7.46-7.52 (1H, m) |
| 87 | 2 | ESI+: 327 |

TEST EXAMPLE

The pharmacological activity of the compound of formula (I) was confirmed by the following tests.

Test Example 1

Obtaining HEK293 Cells Forced to Express Human 5-HT$_{5A}$ Receptor

An open reading frame (ORF; protein coding region) of human 5-HT$_{5A}$ receptor (Genbank AF498985) was cloned from a human hippocampus cDNA library and then inserted into a pCR2.1 vector (Invitrogen), and *E. coli* carrying the plasmid was cultured in a large scale. Thereafter, a full-length cDNA sequence of the human 5-HT$_{5A}$ receptor was analyzed and recombined into pcDNA3.1 vector (Invitrogen) as an expression vector, followed by a large scale culturing. The HEK293 cells (ATCC) as a human embryonic kidney-derived cell line were seeded, and the expression plasmid (1 μg) obtained as above was added thereto together with LIPO-FECTAMINE 2000 (Invitrogen; 2 μl) to introduce genes into the HEK293 cells. Subsequently, expression cells were screened using Geneticin (G418 sulfate 500 μg/ml; KANTO KAGAKU) as a drug resistance marker. The recombinant cells expressing the genes prepared in this manner were cultured for 3 days in Dulbecco's Modified Eagle Medium (D-MEM, Sigma) supplemented with 10% fetal calf serum (FCS), 1% penicillin/streptomycin (Pc./Sm, Invitrogen), and 500 μg/ml G418. The above experimental procedure was performed according to a genetic engineering experiment manual of a known method (Sambrook, J. et al, "Molecular Cloning-A Laboratory manual", Cold Spring Harbor Laboratory, NY, 1989) or the like, or the instruction attached to the reagents.

Test Example 2

Human 5-HT$_{5A}$ Receptor Binding Inhibition Test (1) Preparation of Membrane from HEK293 Cells Forced to Express Human 5-HT$_{5A}$ Receptor The HEK293 cells forced to express the human 5-HT$_{5A}$ receptor were cultured in a F500 plate and collected by being scarped with a scraper. After centrifugation, the sediment was collected, and an incubation buffer (50 mM Tris(HCl), pH 7.4, 10 mM MgSO$_4$, 0.5 mM ethylenediaminetetraacetic acid (EDTA)) was added thereto. After homogenization, centrifugation was performed again, and the sediment was thoroughly suspended in the incubation buffer added thereto. After this procedure was repeated, the protein concentration was measured, thereby completing membrane preparation.

(2) Human 5-HT$_{5A}$ Receptor Binding Inhibition Test

A test compound and 150 μM of a DMSO solution of 5-carboxamide tryptamine (5-CT) were added to a 96-well plate at 2 μl/well and suspended in the incubation buffer, and the HEK293 cells forced to express the human 5-HT$_{5A}$ receptor that were prepared at a concentration of 200 μg/ml were added thereto at 100 μl/well. The cells were incubated for 15 minutes at room temperature, and then a [$^3$H]5-CT solution (3 nM [$^3$H]5-CT, incubation buffer) was added thereto at 100 μl/well.

100 μl of the cell solution was separately dispensed into a liquid scintillation vial, and 2 ml of Aquasol II (registered trademark) was added thereto, followed by stirring. Thereafter, the radioactivity thereof was measured using a liquid scintillation counter. The cells were incubated for 60 minutes at 37° C. The reaction mixture was aspirated into a 96-well GF/C filter plate having undergone pretreatment with 0.2% polyethyleneimine, and washed 6 times with an ice-cold 50 mM Tris (pH 7.4) buffer. Thereafter, the GF/C filter plate was dried.

MicroScint™-PS (registered trademark) was added to the plate at 40 μl/well, and the radioactivity remaining on the GF/C filter plate was measured using TopCount.

In each test example, regarding the [$^3$H]5-CT binding inhibitory activity resulting from the test compound, the radioactivity at the time when only DMSO was added was regarded as 0%, and the radioactivity at the time when 1.5 μM 5-CT was added was regarded as 100% inhibition, thereby calculating an IC$_{50}$ value. In addition, from a Kd value of [$^3$H]5-CT obtained from Scatchard analysis, a Ki value was calculated by the following formula.

$$Ki=IC_{50}/(1+\text{concentration of ligand added}/Kd(4.95 \text{ nM}))$$

Ki values of several example compounds are shown in the following table. In the table, Ex represents an Example compound number.

TABLE 49

| Test compound | Ki [nM] |
| --- | --- |
| Ex 4 | 4.3 |
| Ex 8 | 3.6 |
| Ex 23 | 1.1 |
| Ex 26 | 0.68 |
| Ex 28 | 1.1 |
| Ex 44 | 2.7 |
| Ex 46 | 6.9 |
| Ex 49 | 6.6 |
| Ex 60 | 3.9 |
| Ex 61 | 2.5 |
| Ex 62 | 1.9 |
| Ex 66 | 0.75 |
| Ex 69 | 1.6 |
| Ex 74 | 0.88 |
| Ex 78 | 1.3 |
| Ex 76 | 2.7 |
| Ex 79 | 3.7 |
| Ex 80 | 0.85 |
| Ex 81 | 4.2 |
| Ex 86 | 0.95 |

From the above results, it was confirmed that the compound of formula (I) has affinity to the 5-HT$_{5A}$ receptor.

Test Example 3

Evaluation of Various Agents Against Drugs (Methamphetamine and MK-801) Increasing Level of Physical Activity of Mouse (Physical Activity Level Measurement Using Infrared Rays Emitted)

The improvement effect of the compound of formula (I) on schizophrenia was evaluated by the measurement of the level of physical activity reduced by the administration of the compound, in a model having symptoms induced by methamphetamine (hereinafter, abbreviated to MAP) and MK-801.

(1) Animal

Species: male ICR mouse (2) Procedure of Operation

The animals were taken out of a breeding cage, and the test compound was orally administered to the animal. Thereafter, the animals were put in the breeding cage. 30 minutes later, the animals were put in a cage for measurement, and the level of physical activity of the animals administered only with the test compound was measured. Another 30 to 90 minutes later, the animals were taken out, and drugs (MAP; 1.5 mg/kg or MK-801; 0.3 mg/kg dissolved in physiological saline) increasing the level of physical activity were respectively administered to the animals subcutaneously or intraperitoneally. The level of physical activity for a certain period of time (60 minutes) was measured using an instrument measuring a level of physical activity (CompACT AMS, MUROMACHI KIKAI CO., LTD.) by an infrared sensor.

(3) Analysis

For the normal mouse (mouse administered with physiological saline) and the mouse administered with the medication increasing the level of physical activity, Student's T test was performed in the respective intervals to judge the effect. For the group administered with the test compound, Dunnett's T test was performed for the comparison with a vehicle group, whereby the effect of the compound was tested. When there was a significant difference (P<0.05), the compound was judged to be effective.

When several compounds represented by the formula (I) were used as test compounds, it was confirmed that the increase in the level of physical activity of the mice was inhibited. For example, the compounds of Examples 23, 26, 28, 46, 60, 62, 76, and 78 significantly suppressed the hyperactivity induced by MK-801, at a dose of 0.03 mg/kg, 0.03 mg/kg, 0.03 mg/kg, 0.03 mg/kg, 0.03 mg/kg, 0.01 mg/kg, 0.1 mg/kg, and 0.1 mg/kg respectively. Moreover, the compounds of Examples 26 and 28 significantly inhibited the hyperactivity induced by MAP, at a dose of 0.03 mg/kg respectively. From these results, it was confirmed that the compound of formula (I) has an improvement effect on the increase in the level of physical activity (hyperactivity) which is a symptom of schizophrenia.

Test Example 4

Improvement Effect on Scopolamine- or MK-801-Induced Spontaneous Alternation Behavior in Mouse The improvement effect of the compound of formula (I) on dementia and the cognitive disease of schizophrenia was evaluated by the known test method described above by using a short-term learning disability model.

(1) Animal

Species: male ddy mouse (2) Method of Measurement 10 to 30 minutes after the test compound was orally administered, scopolamine at 0.5 mg/kg or MK-801 (physiological saline for a normal group) at 0.15 mg/kg was intraperitoneally administered, and the test was performed 20 minutes after the administration. In addition, for a normal group (group administered with physiological saline) and a control group (group administered with scopolamine at 0.5 mg/kg or MK-801 at 0.15 mg/kg), a vehicle was orally administered when the test compound was administered.

The mouse was put into one end of an arm of a maze (Y-maze) having arms of the same length that extended in three directions. The mouse was allowed to freely explore for 8 minutes, and the number of entries into the arm for the 8 minutes was counted. Moreover, a case where the mouse consecutively entered three different arms was regarded as spontaneous alternation behavior, and a ratio of the number of times of such a behavior to the total entry number was regarded as alternation rate and calculated by the following formula.

Alternation rate(%)=number of times of spontaneous alternation behavior/(total entry number−2)×100

(3) Data Analysis

When a significant difference (Student's T test) was observed between the normal group and the control group in the alternation rate (%), the learning disability was considered to be induced by the administration of scopolamine or MK-801. By performing Dunnette's test for comparing the test compound-administered groups with the control group, whether or not the test compound has an action causing learning disability was determined. In each test, $p<0.10$ was regarded as a trend, and $p<0.05$ was regarded as a significant difference.

The result of this test showed that the compound of formula (I) inhibits the scopolamine- and MK-801-induced spontaneous alternation behavior of the mouse. For example, the compounds of Examples 23, 26, 28, 46, 62, and 78 significantly inhibited the scopolamine-induced spontaneous alternation behavior, at a dose of 0.003 mg/kg, 0.03 mg/kg, 0.003 mg/kg, 0.003 mg/kg, 0.003 mg/kg, and 0.03 mg/kg respectively.

When several compounds of formula (I) were used as test compounds, it was confirmed that these compounds are effective for dementia and cognitive disorder of schizophrenia.

Test Example 5

Improvement Effect on PCP-Induced Disruption of Prepulse Inhibition (PPI) in Rat Given a sonic stimulus, a human being shows a startle response. However, if a sonic stimulus weaker than the above stimulus is given in advance to a healthy individual, the startle response is inhibited. Such an inhibitory function is depressed in common in patients with schizophrenia. It is known that when phencyclidine (PCP) is administered to a rat, symptoms that are similar to schizophrenia of human being are induced. By using such a model, the improvement effect of the compound of formula (I) on the information processing disorder included in cognitive disorder of schizophrenia was evaluated.

The improvement effect of the compound of formula (I) on schizophrenia was evaluated using a PCP-induced prepulse inhibition disruption model known as a pathological model. Specifically, the evaluation was performed according to the method disclosed in Neuropsychopharmacology, 1989; 2: 299-308, Mansbach, R. S, and Geyer, M. A. and Brain Research, 1998; 781: 227-235.

When several compounds represented by the formula (I) were used as test compounds, it was confirmed that these compounds are also effective for the information processing disorder included in cognitive disorder of schizophrenia.

Test Example 6

Evaluation of Medication in Water-Maze Learning Disability of Aged Rat

The improvement effect of the compound of formula (I) on dementia was evaluated using a water-maze learning disability model known as a pathological model. Specifically, the evaluation was performed according to the method disclosed in J Pharmacol Exp Ther, 1996; 279: 1157-73, Yamazaki M. et al.

When several compounds represented by the formula (I) were used as test compounds, it was confirmed that these compounds are effective for dementia.

Test Example 7

Evaluation of Medication in Forced Swimming Test of DBA/2 Mouse

The improvement effect of the compound of formula (I) on depression can be evaluated by a forced swimming test known as an evaluation model. Specifically, the evaluation is performed according to the method disclosed in Behav Brain Res. 2005; 156 (1): 153-162, Ducottet C. et al.

From the test results of test examples 1 to 7, it was confirmed that the compound of formula (I) is useful as an agent for treating or preventing $5\text{-}HT_{5A}$-related diseases, particularly, dementia, schizophrenia (including symptoms such as positive symptoms, negative symptoms, cognitive disorder, and mood disorder), bipolar disorder, attention deficit hyperactivity disorder, and mood disorder (anxiety disorder and depressive disorder).

Regarding the compound of formula (I), a phototoxic effect was evaluated according to the following test examples.

Test Example 8

Test for Evaluating Phototoxic Effect

[Day 1]: Cell Culture (96-Well Plate)

1) BALB/3T3 is peeled from a culture flask, and the cell number is counted.

2) The cell concentration is adjusted to $0.7 \times 10^5$ cells/ml, and the cells are seeded into a 96-well plate at 100 μl/well. PBS is added in an amount of 100 μl to a line of wells in both ends where the cells are not seeded.

3) The cells are cultured in a $CO_2$ incubator for 1 day.

[Day 2]: Addition of Compound and UV Irradiation (Non-Irradiation)

1) The weight of a test compound is at least 0.8 mg.

2) DMSO-containing EBSS, in which the DMSO concentration is the same as that in the solution of test compound, is prepared in a necessary amount.

3) The DMSO-containing EBSS is put in an amount of 600 μL in tubes (seven tubes for one compound) so as to make preparations for dilution.

4) DMSO is added to a test compound, and the EBSS is further added thereto and dissolved. Ultrasonic waves, heating.

5) The compound solution of the highest concentration is transferred to the adjacent tube by 300 μL. This operation is repeated to prepare solutions having serial dilution concentration.

6) The 96-well plate is put upside down on a paper towel to discard the culture fluid.

7) A multi-pipet is used to aspirate the cells without damaging the cells.

8) The culture fluid of another pair of plates to which the same compound will be added is also discarded in the same manner.

9) The DMSO-containing EBSS is dispensed at 100 μL/well into two lines (4 lines in total) at both ends.

10) For each compound, compound solutions of 8-serial dilutions are dispensed at 100 μL/well.

11) The plates are allowed to stand still in a dark place (in a drawer of a lab bench) for 60 minutes.

12) Thereafter, the plates are irradiated with UV for 70 minutes (1200 μW/cm$^2$). The plate not irradiated is put in an empty box.

13) The plates are put upside down on a paper towel to discard the compound solution. The residual solution is aspirated into the pipet.

14) Culture fluid DMEM for culture is added at 100 μl/well.

15) Culturing is performed in a $CO_2$ incubator.

[Day 3]: Neutral Red Incorporation Test

1) Neutral red (NR) is prepared in an amount of 50 μg/ml

2) The plate is put upside down on a paper towel to discard the culture fluid. The residual culture fluid is not aspirated in the pipet.

3) The NR solution is dispensed at 100 μL/well.

4) Culturing is performed for 3 hours in a $CO_2$ incubator.

5) The plate is put upside down on a paper towel to discard the NR solution. The residual solution is not aspirated into the Pipetman.

6) EBSS is dispensed at 150 μl/well.

7) The plate is put upside down again on a paper towel to discard EBSS. The residual EBSS is aspirated into the Pipetman.

8) The NR eluent is dispensed at 150 μl/well.

9) The plate is shaken with a shaker for about 10 minutes.

10) An absorbance at 540 nm is measured using a microplate reader.

According to the above test example 8, several compounds of formula (I) were evaluated. As a result, it was confirmed that MPE of Examples 23, 26, and 28 is 0.00, which showed that these compounds do not have phototoxicity. Herein, MPE refers to a value showing Mean Photo Effect. MPE can be calculated according to Equation 2 of the following document, for example.

ATLA (2002), 30, 415-432

A preparation containing one or two or more kinds of the compound of formula (I) or a salt thereof as active ingredients can be prepared using a carrier, an excipient, and the like for medications that are generally used in the related art, by means of the method used generally.

The preparation may be administered in any forms such as oral administration by using a tablet, a pill, a capsule, granules, powder, or liquid, and parenteral administration by using a preparation for injection such as intra-articular injection, intravenous injection, and intramuscular injection, a suppository, an eye drop, an eye ointment, a transdermal liquid, an ointment, a transdermal patch, a transmucosal liquid, a transmucosal patch, or an inhalation.

As a solid composition according to the present invention for oral administration, a tablet, powder, granules, and the like are used. In such a solid composition, one or two or more kinds of active ingredients are mixed with at least one inactive excipient, for example, lactic acid, mannitol, glucose, hydroxypropyl cellulose, microcrystalline cellulose, starch, polyvinyl pyrrolidone, and/or magnesium aluminometasilicate. The composition may contain inactive additives, for example, a lubricant such as magnesium stearate, a disintegrating agent such as sodium carboxymethyl starch, a stabilizer, and a solubilizing agent, according to the common method. The tablet or pill may optionally be coated with sugar or with a film of a gastric or enteric substance.

A liquid composition for oral administration includes pharmaceutically acceptable emulsion, liquid, suspension, syrup, elixir, and the like, and contains a generally used inert diluent, for example, purified water or ethanol. The liquid composition may contain an auxiliary agent such as a solubilizer, a moisturizer, or a suspending agent, as well as a sweetener, a flavoring agent, an aromatic, and a preservative, in addition to the inactive diluent.

The injection for parenteral administration includes sterile aqueous or non-aqueous liquid, suspension, and emulsion. Examples of the aqueous solvent include distilled water for injection and physiological saline. Examples of the non-aqueous solvent include propylene glycol, polyethylene glycol, plant oil such as olive oil, alcohols such as ethanol, Polysorbate 80 (pharmacopoeial name), and the like. The above composition may further contain a tonicity agent, a preservative, a moisturizer, an emulsifier, a dispersant, a stabilizer, and a solubilizing agent. These are sterilized by, for example, being filtered through a bacteria retentive filter, compounded with a bactericide, or irradiation. It is also possible to use these by preparing a sterile solid composition and then dissolving or suspending these in sterile water or a sterile solvent for injection before use.

Examples of agents for external use include an ointment, a plaster, a cream, a jelly, a cataplasm, a spray, a lotion, eye drops, an eye ointment, and the like. The agent for external use contains generally used base materials of ointments and lotions, an aqueous or non-aqueous liquid formulation, a suspension, an emulsion, and the like. Examples of the base materials of the ointment or lotion include polyethylene glycol, propylene glycol, white vaseline, white bees wax, polyoxyethylene hydrogenated castor oil, glycerin monostearate, stearyl alcohol, cetyl alcohol, lauromacrogol, sorbitan sesquioleate, and the like.

Transmucosal agents such as an inhalation agent and transnasal agent are used in the form of a liquid or a semisolid, and can be prepared according to methods known in the related art. For example, a known excipient, a pH adjustor, a preservative, a surfactant, a lubricant, a stabilizer, a thickener or the like may be appropriately added thereto. For administration, appropriate devices for inhalation or insufflation can be used. For example, by using a known device such as a metered dose inhaler or an atomizer, the compound can be administered alone or administered as powder of a formulated mixture or as a solution or suspension which is a combination of the compound with a pharmaceutically acceptable carrier. A dry powder inhaler and the like may be for single administration or multiple administration, and dry powder or powder-containing capsules can be used. Alternatively, the device can be in the form of a pressurized aerosol spray using an appropriate ejection agent, for example, suitable gas such as chlorofluoroalkane, hydrofluoroalkane, or carbon dioxide.

Generally, in the case of oral administration, an appropriate daily dose is about 0.0001 mg/kg to 100 mg/kg in terms of body weight, preferably 0.0001 mg/kg to 10 mg/kg, and more preferably 0.0001 mg/kg to 1 mg/kg, which is administered once or two to four times in separate doses. In the case of intravenous administration, an appropriate daily dose is about 0.00001 mg/kg to 1 mg/kg in terms of body weight, which is administered once or plural times in separate doses. In addition, the agent for external use or the transmucosal agent is administered once a day or plural times a day in separate doses, in a dose of about 0.0001 mg/kg to 10 mg/kg in terms of body weight. The dose is appropriately determined case by case in consideration of the symptoms, age, sex, and the like. The content of active ingredients in the preparation is 0.0001% to 50% and more preferably 0.001% to 50%.

The compound represented by the formula (I) can be used concurrently with an agent for treating or preventing various diseases considered to be diseases for which the compound of the formula (I) is effective. In concurrent use, the compound and the agent may be administered simultaneously, administered sequentially one by one, or administered at a desired time interval. The preparation for simultaneous administration may be a combination drug or individual preparations.

INDUSTRIAL APPLICABILITY

The compound represented by the formula (I) has such advantages that it has a potent $5\text{-HT}_{5A}$ receptor regulating action and excellent pharmacological action based on the regulating action. The pharmaceutical composition of the present invention is useful for treating or preventing $5\text{-HT}_{5A}$ receptor-related diseases, particularly, dementia, schizophrenia, bipolar disorder, and attention deficit hyperactivity disorder.

The invention claimed is:
1. A compound represented by formula (I) or a pharmaceutically acceptable salt thereof,

[Chem. 11]

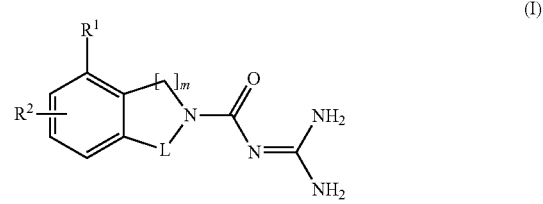

(I)

wherein:
$R^1$ is chosen from H, —O-(lower alkyl), —O-(halogeno-lower alkyl), aryl, heteroaryl, cycloalkyl, and cycloalkenyl, wherein aryl, heteroaryl, cycloalkyl, and cycloalkenyl may be unsubstituted or respectively substituted with substituent(s) selected from $G^1$,
$G^1$ is chosen from halogen, —CN, —OH, —O-(lower alkyl), —O-(halogeno-lower alkyl), lower alkyl, halogeno-lower alkyl, -(lower alkylene)-OH, -(lower alkylene)-O-(lower alkyl), and cycloalkyl,
$R^2$ is chosen from H, lower alkyl, halogeno-lower alkyl, halogen, —CN, —OH, —O-(lower alkyl), —O-(halogeno-lower alkyl), -(lower alkylene)-OH, -(lower alkylene)-O-(lower alkyl), and cycloalkyl,
L: —C($R^3$)($R^4$)—(CH$_2$)$_n$—,
m: 1 or 2,
n: 0, 1, or 2,
$R^3$ and $R^4$ may be the same as or different from each other and respectively chosen from H, lower alkyl, halogen, —OH, and —O-(lower alkyl); alternatively, $R^3$ and $R^4$ may be combined with each other to form —$R^3$—$R^4$—, and —$R^3$—$R^4$— may form cycloalkylene together with the carbon atom binding thereto, as a lower alkylene having 2 or more carbon atoms.
2. The compound according to claim 1 or a pharmaceutically acceptable salt thereof,
wherein $R^1$ is chosen from phenyl, pyridyl, and cycloalkyl which may be respectively substituted with group(s) selected from $G^1$, $R^2$ is chosen from halogen, m represent 1, n represents 1, and both $R^3$ and $R^4$ represent H.
3. The compound according to claim 1 or a pharmaceutically acceptable salt thereof,
wherein $R^1$ represents phenyl which may be substituted with group(s) chosen from halogen and —O-(lower alkyl), $R^2$ is chosen from H, F, Cl, and methyl, m represents 1, n represents 1, and both $R^3$ and $R^4$ represent H.
4. The compound according to claim 1 or a pharmaceutically acceptable salt thereof,
wherein $R^1$ represents pyridyl which may be substituted with group(s) chosen from halogen and —O-(lower alkyl), $R^2$ is chosen from H, F, Cl, and methyl, m represents 1, n represents 1, and both $R^3$ and $R^4$ represent H.

5. The compound according to claim 1 or a pharmaceutically acceptable salt thereof,
wherein $R^1$ represents phenyl which may be substituted with group(s) chosen from halogen and —O-(lower alkyl), $R^2$ is chosen from H, F, Cl, and methyl, m represents 1, n represents 1, and $R^3$ and $R^4$ form cyclopropane-1,1-diyl or cyclobutane-1,1-diyl together with the carbon atom binding thereto, as ethylene or trimethylene.

6. A compound selected from the following group of compounds, or a pharmaceutically acceptable salt thereof:
N-(diaminomethylene)-5-fluoro-8-(2,4,6-trifluorophenyl)-3,4-dihydroisoquinoline-2(1H)-carboxamide,
N-(diaminomethylene)-8-(2,6-difluorophenyl)-5-fluoro-3,4-dihydroisoquinoline-2(1H)-carboxamide,
N-(diaminomethylene)-8-(3,5-difluoropyridin-2-yl)-5-fluoro-3,4-dihydroisoquinoline-2(1H)-carboxamide,
N-(diaminomethylene)-8-(3,5-difluoropyridin-2-yl)-5-methyl-3,4-dihydroisoquinoline-2(1H)-carboxamide,
N-(diaminomethylene)-8-(3,5-dichloropyridin-2-yl)-5-fluoro-3,4-dihydroisoquinoline-2(1H)-carboxamide,
N-(diaminomethylene)-5'-fluoro-8'-(2,4,5-trifluorophenyl)-1'H-spiro[cyclopropane-1,4'-isoquinoline]-2'(3'H)-carboxamide,
5-chloro-N-(diaminomethylene)-8-(2,4,6-trifluorophenyl)-3,4-dihydroisoquinoline-2(1H)-carboxamide,
8'-cyclopropyl-N-(diaminomethylene)-5'-fluoro-1'H-spiro[cyclopropane-1,4'-isoquinoline]-2'(3'H)-carboxamide,
N-(diaminomethylene)-5-fluoro-8-(2,4,5-trifluorophenyl)-3,4-dihydroisoquinoline-2(1H)-carboxamide,
N-(diaminomethylene)-8'-(2,6-difluorophenyl)-5'-fluoro-1'H-spiro[cyclopropane-1,4'-isoquinoline]-2'(3'H)-carboxamide,
N-(diaminomethylene)-5'-fluoro-8'-(2,4,6-trifluorophenyl)-1'H-spiro[cyclopropane-1,4'-isoquinoline]-2'(3'H)-carboxamide,
N-(diaminomethylene)-8'-(2,4-difluorophenyl)-5'-fluoro-1'H-spiro[cyclopropane-1,4'-isoquinoline]-2'(3'H)-carboxamide, and
N-(diaminomethylene)-5'-fluoro-8'-(2-fluorophenyl)-1'H-spiro[cyclopropane-1,4'-isoquinoline]-2'(3'H)-carboxamide.

7. A pharmaceutical composition comprising the compound according to claim 1 or a pharmaceutically acceptable salt thereof; and a pharmaceutically acceptable excipient.

8. The pharmaceutical composition according to claim 7, which is a $5\text{-HT}_{5A}$ receptor regulator.

9. The pharmaceutical composition according to claim 8, which is for treating dementia, schizophrenia, bipolar disorder, attention deficit hyperactivity disorder, or mood disorder.

10. The compound according to claim 1 or a pharmaceutically acceptable salt thereof for treating dementia, schizophrenia, bipolar disorder, attention deficit hyperactivity disorder, or mood disorder.

11. A method for treating dementia, schizophrenia, bipolar disorder, attention deficit hyperactivity disorder, or mood disorder, comprising administering a therapeutically effective amount of the compound according to claim 1 or a pharmaceutically acceptable salt thereof to a subject.

12. The compound of claim 1, wherein said compound is N-(diaminomethylene)-5-fluoro-8-(2,4,6-trifluorophenyl)-3,4-dihydroisoquinoline-2(1H)-carboxamide, or a pharmaceutically acceptable salt thereof.

13. The compound of claim 1, wherein said compound is N-(diaminomethylene)-8-(2,6-difluorophenyl)-5-fluoro-3,4-dihydroisoquinoline-2(1H)-carboxamide, or a pharmaceutically acceptable salt thereof.

14. The method of claim 11, wherein said compound is N-(diaminomethylene)-5-fluoro-8-(2,4,6-trifluorophenyl)-3,4-dihydroisoquinoline-2(1H)-carboxamide, or a pharmaceutically acceptable salt thereof.

15. The method of claim 11, wherein said compound is N-(diaminomethylene)-8-(2,6-difluorophenyl)-5-fluoro-3,4-dihydroisoquinoline-2(1H)-carboxamide, or a pharmaceutically acceptable salt thereof.

* * * * *

UNITED STATES PATENT AND TRADEMARK OFFICE
CERTIFICATE OF CORRECTION

PATENT NO.          : 8,962,612 B2
APPLICATION NO.     : 13/956924
DATED               : February 24, 2015
INVENTOR(S)         : Wataru Hamaguchi et al.

It is certified that error appears in the above-identified patent and that said Letters Patent is hereby corrected as shown below:

On the Title Page, Item (71), in the "Applicant", line 1, "Inc," should read --Inc.,--.

Claims

In claim 1, column 108, line 17, above the structure for formula (I), delete "[Chem. 11]".

In claim 2, column 108, lines 56-57, "m represent 1," should read --m represents 1,--.

Signed and Sealed this
Twelfth Day of July, 2016

Michelle K. Lee
*Director of the United States Patent and Trademark Office*